US008163290B2

(12) United States Patent
Tsuji et al.

(10) Patent No.: US 8,163,290 B2
(45) Date of Patent: *Apr. 24, 2012

(54) GLYCOLIPIDS AND ANALOGUES THEREOF AS ANTIGENS FOR NKT CELLS

(75) Inventors: Moriya Tsuji, New York, NY (US); David D. Ho, New York, NY (US); Chi-Huey Wong, Rancho Santa Fe, CA (US); Douglass Wu, San Diego, CA (US); Masakazu Fujio, San Diego, CA (US); Xiangming Li, Elmhurst, NY (US)

(73) Assignees: The Rockefeller University, New York, NY (US); The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,996

(22) Filed: Dec. 2, 2010

(65) Prior Publication Data
US 2011/0086053 A1 Apr. 14, 2011

Related U.S. Application Data

(63) Continuation of application No. 11/735,313, filed on Apr. 13, 2007, now Pat. No. 7,923,013, which is a continuation-in-part of application No. 11/317,900, filed on Dec. 27, 2005, now Pat. No. 7,534,434.

(60) Provisional application No. 60/639,408, filed on Dec. 28, 2004.

(51) Int. Cl.
*A61K 39/00* (2006.01)
(52) U.S. Cl. .................................... 424/184.1; 536/17.9
(58) Field of Classification Search ........................ None
See application file for complete search history.

(56) References Cited

U.S. PATENT DOCUMENTS

| 5,405,772 | A | 4/1995 | Ponting |
| 5,663,151 | A | 9/1997 | Martel et al. |
| 5,767,092 | A | 6/1998 | Koezuka et al. |
| 5,849,716 | A | 12/1998 | Akimoto et al. |
| 5,936,076 | A | 8/1999 | Higa et al. |
| 6,417,167 | B1 | 7/2002 | Maruyama et al. |
| 2007/0238871 | A1 | 10/2007 | Tsuji et al. |

FOREIGN PATENT DOCUMENTS

| EP | 0988860 A1 | 3/2000 |
| EP | 1437358 A1 | 7/2004 |
| EP | 1619199 A1 | 1/2006 |
| WO | WO 9320185 A1 | 10/1993 |
| WO | WO 9500632 A1 | 1/1995 |
| WO | WO 9506112 A1 | 3/1995 |
| WO | 2004/072091 A1 | 8/2004 |
| WO | WO2006/026389 A2 | 3/2006 |
| WO | WO2006/071848 A2 | 7/2006 |
| WO | WO2007/035717 A2 | 3/2007 |

OTHER PUBLICATIONS

Porcelli, S. A. & Modlin, R. L. Annu, "The CD1 System: Antigen-Presenting Molecules for T cell Recognition of Lipids and Glycolipids," *Annu. Rev. Immunol.* 17:297-329 (1999).
Green and P.G.M. Wits, "Protection for the Amino Group," *Protective Groups in Organic Synthesis*, 3rd Edition:494-653 (1999).
Caux et al., "GM-CSF and TNF-a Cooperate in the Generation of Dendritic Langerhans Cells," *Nature 360*, Palgrave Macmilland Ltd, pp. 258-261 (1992).
Romani et al, "Proliferating Dendritic Cell Progenitors in Human Blood," *Journal of Experimental Medicine*, vol. 180, Rockefeller University Press, pp. 83-93 (1994).
Bender et al., "Improved Methods for the Generation of Dendritic Cells From Nonproliferating Progenitors in Human Blood," *Journal of Immunological Methods*, 196(2):121-135, Elsevier Science B.V. (1996).
O'Doherty et al., "Human Blood Contains Two Subsets of Dendritic Cells, One Immunologically Mature and the Other Immature," *Immunology*, 82(3):487-493 (1994).
O'Doherty et al., "Dendritic Cells Freshly Isolated From Human Blood Express CD4 and Mature Into Typical Immunostimulatory Dendritic Cells After Culture in Monocyte-Conditioned Medium," *Journal of Experimental Medicine*, 178:1067-1076, Rockefeller University Press (1993).
Xing, G.W., et al., "Synthesis and human NKT cell stimulating properties of 3-0-Sulfo-a/b-galactosylceramides", *Bioorg. Med. Chem*, 15;13(8):2907-2916 (2005).
Hsu et al., "Vaccination of Patients with B-Cell Lymphoma Using Autologous Antigen-Pulsed Dendritic Cells,"*Nature Medicine*, 2:52-58 (1996).
Bonifaz et al., "Efficient Targeting of Protein Antigen to the Dendritic Cell Receptor DEC-205 in the Steady State Leads to Antigen Presentation on Major Histocompatibiilty Complex Class I Products and Peripheral CD8+ T Cell Tolerance," *Journal of Experimental Medicine*, 196(12):1627-1638 (2002).
Manavalan et al., "High Expression of ILT3 and ILT4 is a general feature of tolerogenic dendritic cells", *Transplant Immunology*, 11:245-258 (2003).
Kawahara et al., "Occurrence of an a-galacturonosyl-ceramide in the dioxin-degrading bacterium Sphingomonas wittichii," *FEMS Microbiology Letters*, 214(2):289-294 (2002).
Kumar et al., "Cutting Edge: CD1d Deficiency Impairs Murine Host Defense Against the Spirochete, Borrelia burgdorferi," *The Journal of Immunology*, 165:4797-4801 (2000).
Ben-Menachem et al., "A Newly Discovered Cholesteryl Galactoside from Borrelia Burgdorferi," *Microbiology*, 100(13):7913-7918 (2003).
Figueroa-Perez, S. et al., "Total synthesis of a-galactosyl cerebroside", *Carbohydrate Research*, 328:95-102 (2000).
Plettenburg, O. et al., "Synthesis of a-Galactosyl Ceramide, a Potent Immunostimulatory Agent", *J. Org. Chem.*, 67:4559-4564 (2002).
Compostella, F. et al. "CD1a-binding glycosphingolipids stimulating human autoreactive T-cells; synthesis of a family of sulfatides differing in the acyl chain moiety", *Tetrahedron*. 58:8703-8708 (2002).

(Continued)

*Primary Examiner* — Elli Peselev
(74) *Attorney, Agent, or Firm* — Heslin Rothenberg Farley & Mesiti P.C.; Andrew K. Gonsalves

(57) ABSTRACT

This invention relates to immunogenic compounds which serve as ligands for NKT (natural killer T) cells and to methods of use thereof in modulating immune responses.

19 Claims, 39 Drawing Sheets

OTHER PUBLICATIONS

Williams, L. et al. "Grignard Reactions to Chiral Oxazolidine Aldehydes", *Tetrahedron*, 52:11673-11694 (1996).

Sidobre et al., "The T Cell Antigen Receptor Expressed by Va14i NKT Cells has a Unique Mode of Glycosphingolipid Antigen Recognition," *PNAS*, Aug. 17, 101(33):12254-12259 (2004).

Zeng et al., "Crystal Structure of Mouse CD1: An MHC-Like Fold with a Large Hydrophobic Binding Groove", *Science*, 277:339-345 (1997).

Morris, G.M. et al., "Automated Docking Using a Lamarckian Genetic Algorithm and an Empirical Binding Free Energey Function," *Journal of Computational Chemistry*, John Wiley & Sons, Inc., 19(14):1639-1662 (1998).

Goff, R.D., et al., "Effects of Lipid Chain Lengths in a-Galactosylceramides on Cytokine Release by Natural Killer T Cells", *Journal Am. Chem. Soc.*, 126:13602-13603 (2004).

Shirota et al., "Phytosphingosines—A Facile Synthesis and Spectroscopic Protocol for Configurational Assingment", *Tetrahedron*, 55:13643-13658 (1999).

Elewaut D., et al., "The Adaptor Protein AP-3 is Require for CD1d-Mediated Antigen Presentation of Glycosphingolipids and Development of Va14i NKT Cells", *Journal of Experimental Medicine*, 198:1133-1146 (2003).

Wu, D. et al., "Bacterial Glycolipids and Analogs as Antigens for CD1d-Restricted NKT Cells," *PNAS*, 102(5):1351-1356 (2005).

Deng, S.Y., et al., "Highly Efficient Glycosylation of Sapogenins", *J. Org. Chem.*, 64:7265-7266 (1999).

Koch, M., et al., "The crystal structure of human CD1d with and without a-galactosylceramide", *Nat. Immunol.*, 6:819-826 (2005).

International Search Report and Written Opinion from PCT/US2005/047017 mailed Jul. 25, 2006.

Zajonc, D. et al. "Structure and Function of a Potent Agonist for the Semi-Invariant NKT Cell Receptor", *Nat. Immunol.*, 6(8): 810-818 (2005).

Kinjo, Y. et al. "Recognition of bacterial glycosphingolipids by natural killer T cells", *Nature*, 434:520-525 (2005).

Fujio, M. et al. "Structure-Based Discovery of Glycolipids for Cdld-Mediated NKT Cell Activation: Tuning the Adjuvant versus Immunosuppression Activity". *J. Am. Chem. Soc.*, 128:9022-9023 (2006).

Toba et al. "Minimum structure requirement of immunomodulatory glycolipids for predominant Th2 cytokine induction and the discovery of non-linear phytosphingosine analogs," *Biorganic& Medicinal Chemistry Letters*, Oxford, GB, 17(10):2781-2784 (2007).

International Search Report and Written Opinion from PCT/US2008/060061 mailed on Sep. 8, 2008.

Supplementary European Search Report issued in EP 05857215.7, mailed Jul. 4, 2011.

Natori et al., "Agelasphins, Novel Antitumor and Immunostimulatory Cerebrosides from the Marine Sponge *Agelas Mauritianus*," *Tetrahedron* 50:2771-2784 (1994).

H.M. Flowers, "Substituted Cerebrosides," *Carbohydrate Research*, 2:188-196 (1966).

Kobayashi et al., "Enhancing Effects of α-, β-Monoglycosylceramides on Natural Killer Cell Activity," *Bioorganic & Medicinal Chemistry*, 4(4):615-619 (1996).

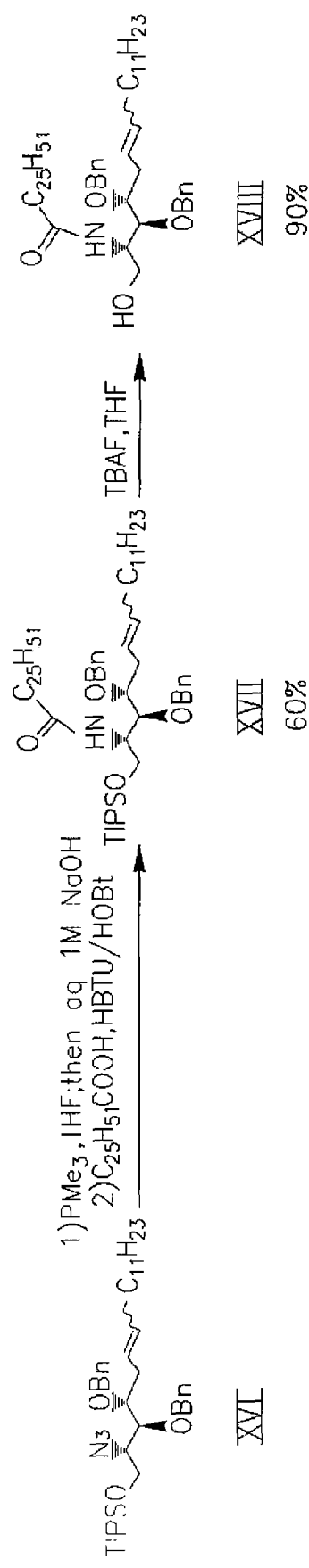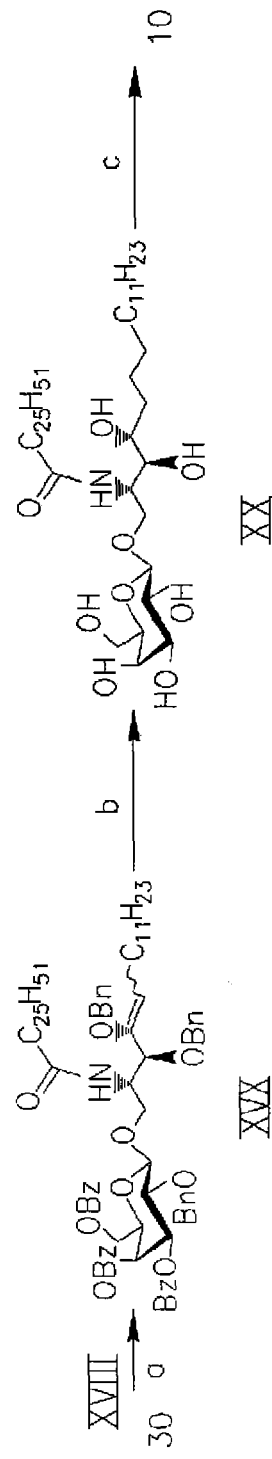
FIG. 4A
FIG. 4B

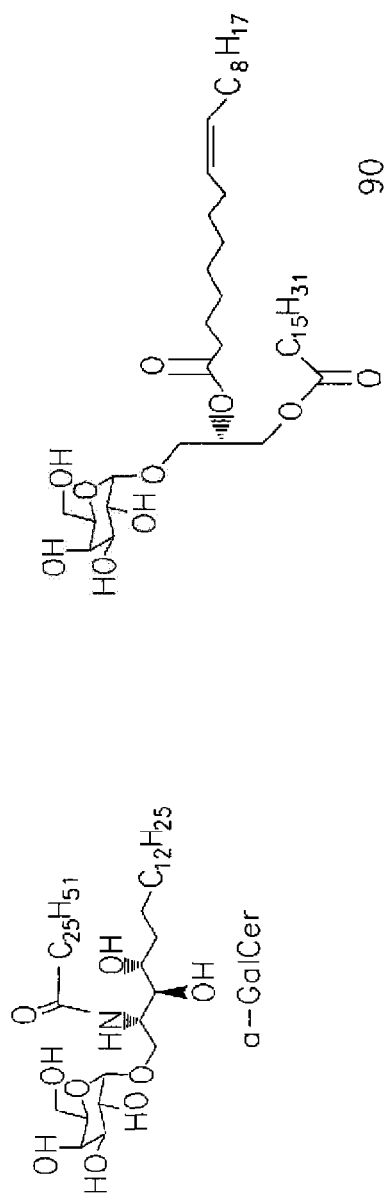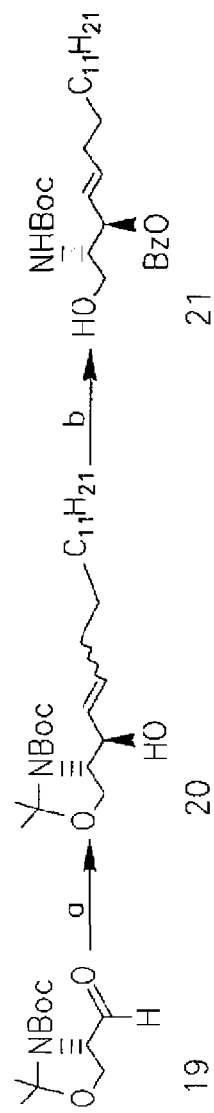
FIG. 5C
FIG. 6

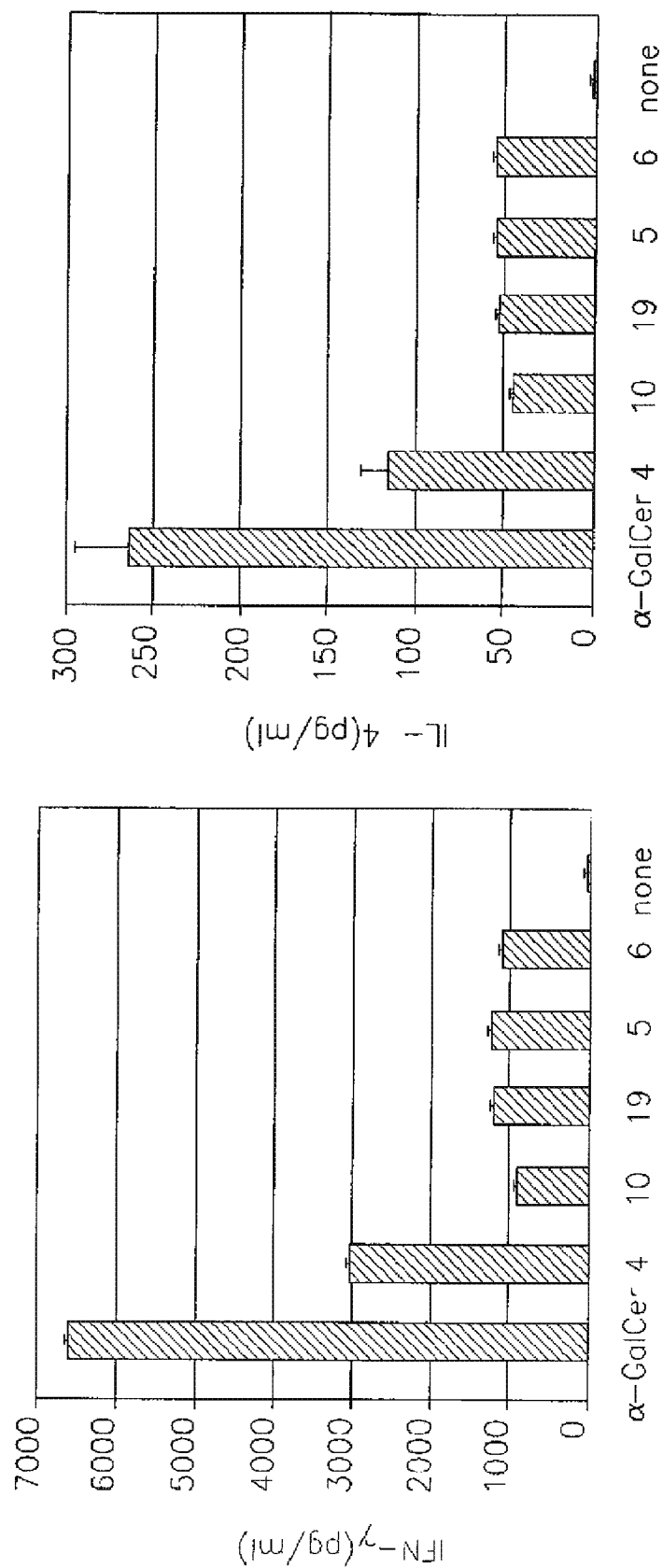

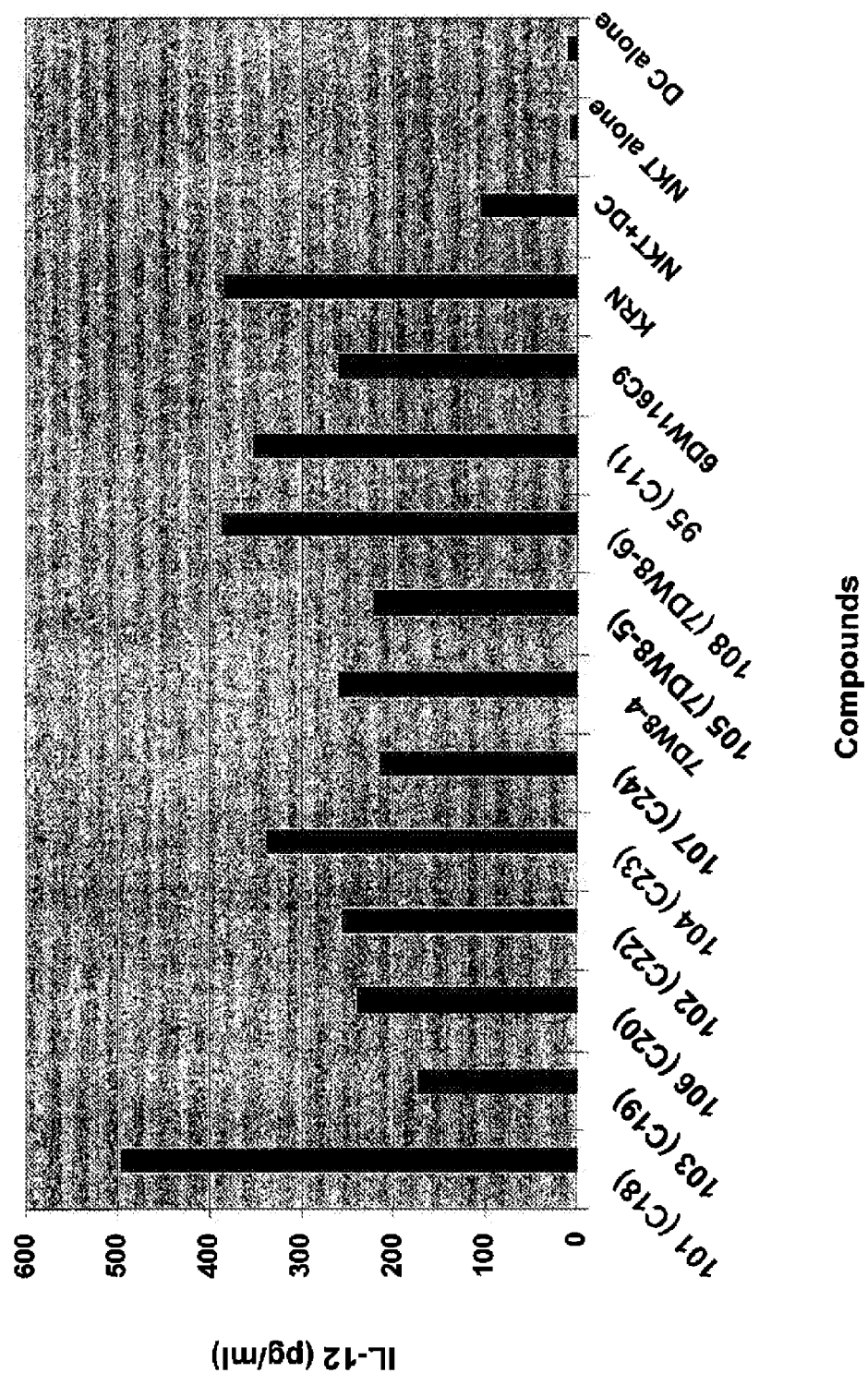

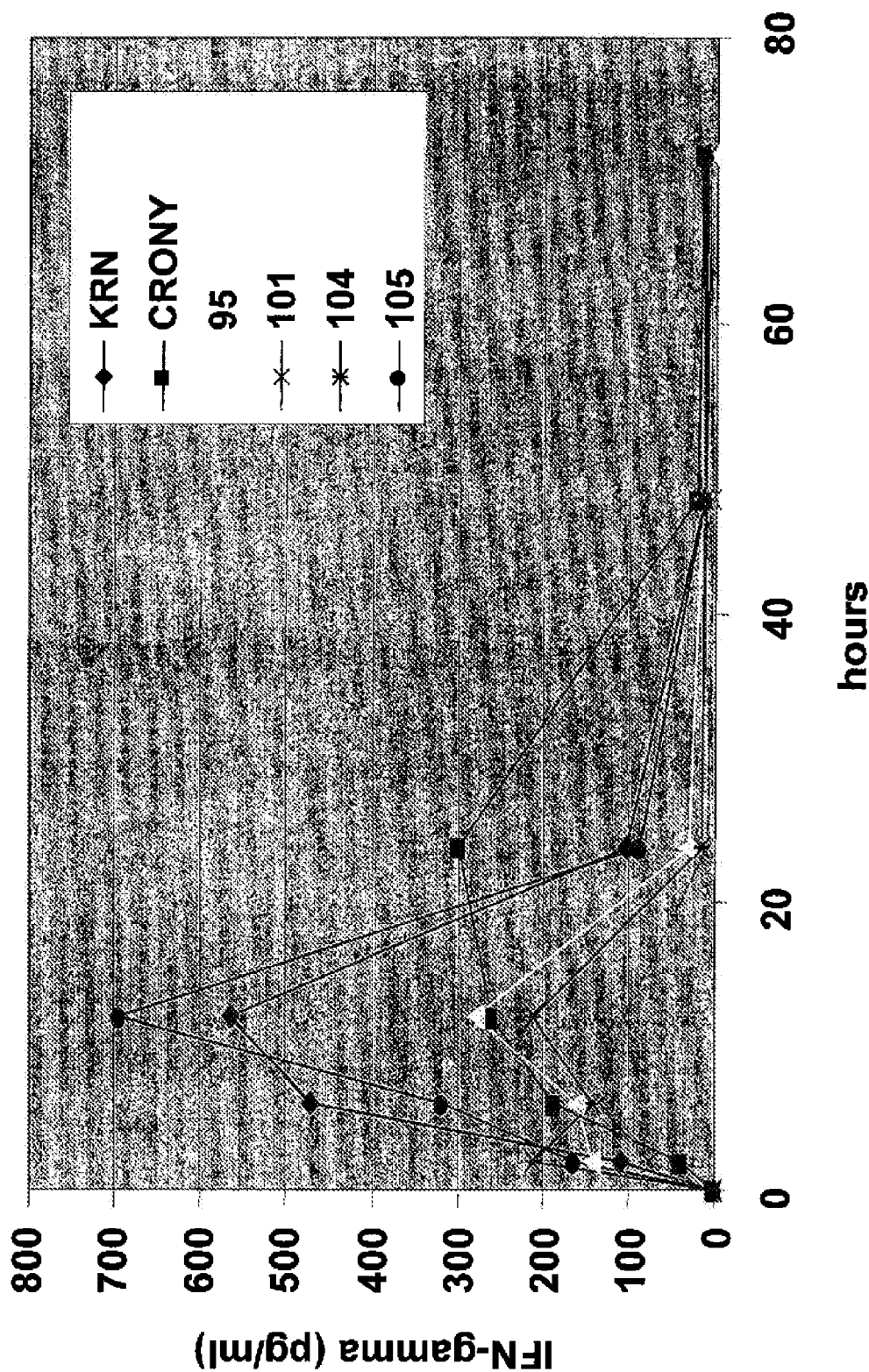

GLYCOLIPIDS AND ANALOGUES THEREOF AS ANTIGENS FOR NKT CELLS

CROSS-REFERENCE TO RELATED APPLICATIONS

This Application is a continuation of U.S. patent application Ser. No. 11/735,313, filed Apr. 13, 2007, currently pending, which is a continuation-in-part of U.S. patent application Ser. No. 11/317,900, filed Dec. 27, 2005, now U.S. Pat. No. 7,534,434, issued May 19, 2009, which claims the benefit of U.S. Provisional Patent Application Ser. No. 60/639,408, filed Dec. 28, 2004, each of which is incorporated by reference herein in its entirety.

STATEMENT OF FEDERALLY SPONSORED RESEARCH

This invention was made in whole or in part with government support under grant number GM44154, awarded by the National Institute of Health. The government may have certain rights in the invention.

FIELD OF THE INVENTION

This invention relates to immunogenic compounds that serve as ligands for natural killer T (NK T) cells and to methods of use thereof in modulating immune responses.

BACKGROUND OF THE INVENTION

CD1 molecules are a family of highly conserved antigen presenting proteins that are similar in function to classical MHC molecules. While classical MHC molecules present peptides, CD1 proteins bind and display a variety of lipids and glycolipids to T lymphocytes. The five known isoforms are classified into two groups, group I (CD1a, CD1b, CD1c, and CD1e in humans) and group II (CD1d in humans and mice) based on similarities between nucleotide and amino acid sequences.

A great diversity of lipids and glycolipids has been shown to bind specifically to each of the four isoforms. The first crystal structure of murine (m) CD1d revealed that it adopts a folded conformation closely related to major histocompatibility complex (MHC) class I proteins. It further revealed that mCD1d could accommodate long lipid tails in two hydrophobic pockets, designated A' and F', located in the binding groove. Two additional structures of hCD1b and hCD1a confirmed this model by demonstrating that CD1, when loaded with antigenic glycolipids, binds the lipid portion in a hydrophobic groove while making available the hydrophilic sugar moiety to make contact with the T-cell receptor.

Mammalian and mycobacterial lipids are known to be presented by human CD1a, CD1b, CD1c and CD1d [Porcelli, S. A. & Modlin, R. L. (1999) *Annu. Rev. Immunol.* 17, 297-329]. α-Galactosylceramide (α-GalCer), a lipid found in the marine sponge *Agelas mauritianus*, has been, to date, the most extensively studied ligand for CD1d. α-GalCer, when bound to CD1d, stimulates rapid Th1 and Th2 cytokine production by Vα14i natural killer T (Vα14i NKT) cells in mice and the human homologue Vα24i NKT cells. However, its physiological significance in mammals remains unclear as it is enigmatic why an α-galactosyl ceramide of marine origin is such a potent agonist. Other known ligands, such as a bacterial phospholipid ($PIM_4$), a tumor derived ganglioside GD3, a C-linked analog of α-GalCer, α-GalCer analogues with different lipid chain lengths and a phosphoethanolamine, found in human tumor extracts, stimulate only relatively small populations of CD1d-restricted NKT cells.

Natural Killer (NK) cells typically comprise approximately 10 to 15% of the mononuclear cell fraction in normal peripheral blood. Historically, NK cells were first identified by their ability to lyse certain tumor cells without prior immunization or activation. NK cells also serve a critical role in cytokine production, which are thought to be involved in controlling cancer, infection and fetal implantation.

In view of the above, it would be desirable to elucidate additional glycolipid compounds and/or analogues of known glycolipids, such as α-GalCer, that enhance cell mediated immune responses and that are useful for the development of glycolipid-containing adjuvants and vaccines and for any immunotherapy designed to stimulate NKT cells.

SUMMARY OF THE INVENTION

The present invention is based in part on the discovery of novel glycolipid analogues that enhance cell mediated immune responses and that are useful for developing vaccines for treating a variety of diseases and disorders requiring immunotherapy and stimulation of NK T cells.

This invention provides, in one embodiment, a compound represented by the structure of formula 1:

(1)

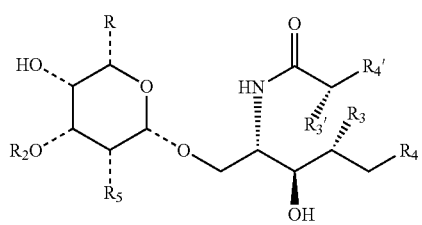

wherein, $R=COOR_1$ or $CH_2OR_1$;
$R_1$=H or an alkyl group;
$R_2$=H or $SO_3^-$;
$R_3$=H or OH;
$R_3'$=H or OH;
$R_4$ and $R_4'$ are independently chosen from
(a) H,
(b) alkyl;
(c) alkenyl; and
(d) oxaalkyl;
$R_5$=OH, acetamido or a halogen atom;
or a pharmaceutically acceptable salt thereof,
wherein if $R=CH_2OR_1$, $R_2$=H, $R_3$ is OH and $R_3'$ is H, then one of the following is true:
(i) $R_5$=acetamido, halogen atom or OH in an axial position;
(ii) $R_4$=H, or unsaturated or saturated alkyl chain having 9 carbon atoms or fewer; or
(iii) $R_4'$=H, or unsaturated or saturated alkyl chain having 20 carbon atoms or fewer.

In another embodiment, this invention provides a compound represented by the structure of formula 2:

(2)

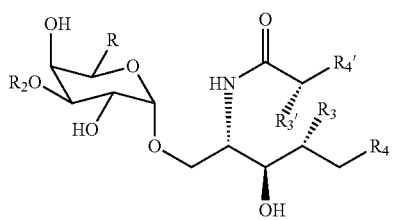

wherein $R=COOR_1$ or $CH_2OR_1$;
$R_1$=H or an alkyl group;
$R_2$=H or $SO_3^-$;

$R_3$=H or OH;
$R_3'$=H or OH; and
$R_4$=H, unsaturated or saturated, alkyl group; and
$R_4'$=H, unsaturated or saturated, alkyl group;
or a pharmaceutically acceptable salt thereof,
wherein if R=$CH_2OR_1$, $R_2$=H, $R_3$ is OH and $R_3'$ is H, then $R_4$=H, unsaturated or saturated, alkyl chain having 9 carbon atoms or fewer, or $R_4'$=H, unsaturated or saturated, alkyl chain having 20 carbon atoms or fewer.

In another embodiment, this invention provides a compound represented by the structure of formula 3:

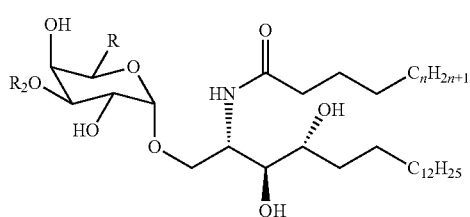

(3)

wherein, R=$COOR_1$ or $CH_2OR_1$;
$R_1$=H or an alkyl group;
$R_2$=$SO_3^-$; and
n=integer;
or a pharmaceutically acceptable salt thereof.

In another embodiment, this invention provides a compound represented by the structure of formula 4:

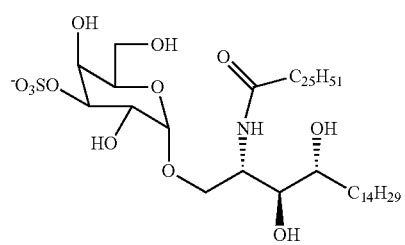

(4)

or a pharmaceutically acceptable salt thereof.
In another embodiment, the salt may be, inter alia, a sodium salt.

In another embodiment, this invention provides a compound represented by the structure of formula 5:

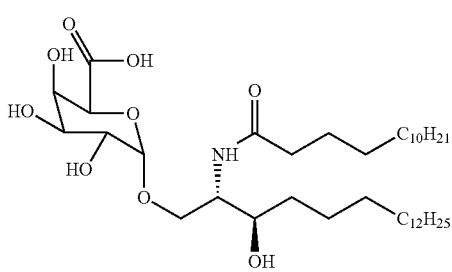

(5)

In another embodiment, this invention provides a compound represented by the structure of formula 6:

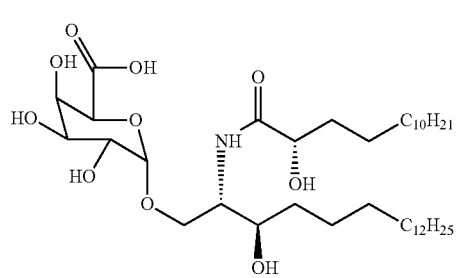

(6)

In another embodiment, this invention provides a compound represented by the structure of formula 7:

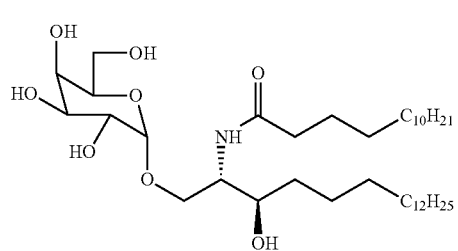

(7)

In another embodiment, this invention provides a compound represented by the structure of formula 8:

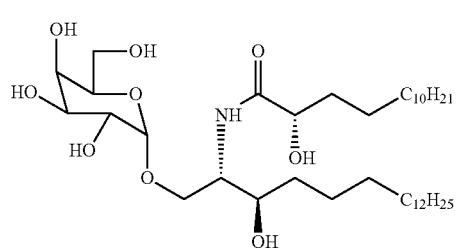

(8)

In one embodiment, this invention provides a compound represented by the structure of formula 9:

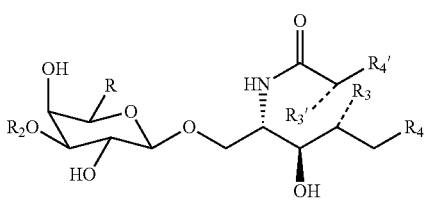

(9)

wherein, R=$COOR_1$ or $CH_2OR_1$
$R_1$=H or an alkyl group;
$R_2$=H or $SO_3^-$;
$R_3$=OH;
$R_3'$=H or OH; and
$R_4$=H, unsaturated or saturated, alkyl group; and
$R_4'$=H, unsaturated or saturated, alkyl group;
or a pharmaceutically acceptable salt thereof, wherein if R=CH₂OR₁, R₂=H, R₃ is OH and R₃' is H, then R₄=H, unsaturated or saturated, alkyl chain having 9 carbon atoms or fewer, or R₄'=H, unsaturated or saturated, alkyl chain having 20 carbon atoms or fewer.

In another embodiment, this invention provides a compound represented by the structure of formula 10:

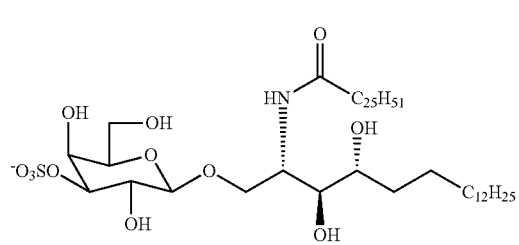

(10)

or a pharmaceutically acceptable salt thereof. In another embodiment, the salt may be, inter alia, a sodium salt.

This invention provides, in one embodiment, a compound represented by the structure of formula 11:

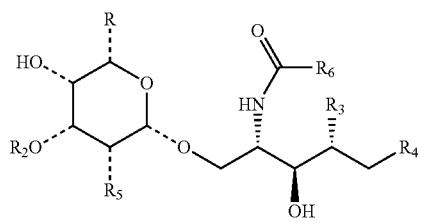

(11)

wherein, R=COOR₁ or CH₂OR₁;
  R₁=H or an alkyl group;
  R₂=H or SO₃⁻;
  R₃=H or OH;
  R₄=H, unsaturated or saturated, alkyl group;
  R₅=OH, acetamido or a halogen atom; and
  R₆=X-A
  A=
  dialkyl phenyl;

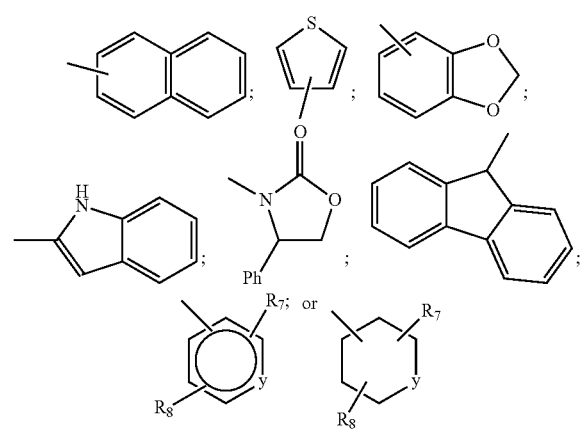

X=alkyl, alkenyl, alkoxy, thioalkoxy, substituted furan, or unsubstituted furan;
Y=N or C R7=halogen, H, phenyl, alkyl, alkoxy, nitro or CF3; and
R8=methyl or H;
or a pharmaceutically acceptable salt thereof.

In another embodiment, this invention provides a compound represented by the structure of formula 12:

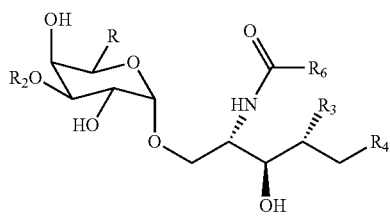

(12)

or a pharmaceutically acceptable salt thereof.

In another embodiment, this invention provides a compound represented by the structure of formula 13:

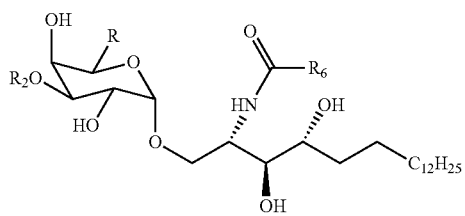

(13)

or a pharmaceutically acceptable salt thereof.

In another embodiment, this invention provides a compound represented by the structure of formula 14:

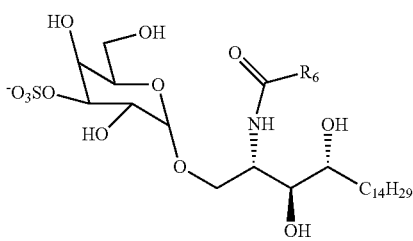

(14)

or a pharmaceutically acceptable salt thereof.

In another embodiment, the salt may be, inter alia, a sodium salt.

In another embodiment, this invention provides a compound represented by the structure of formula 15:

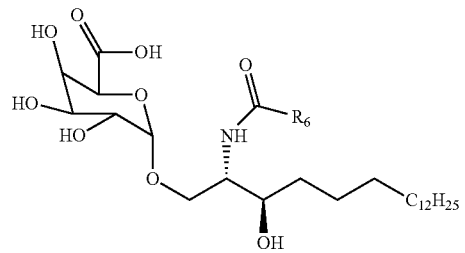

(15)

In another embodiment, this invention provides a compound represented by the structure of formula 16:

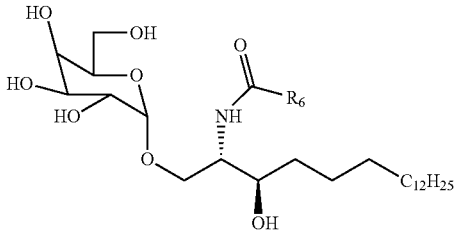

(16)

In still another embodiment, this invention provides a compound represented by the structure of formula 17:

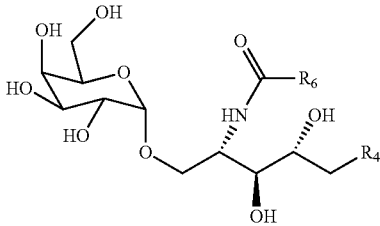

(17)

wherein
$R_4$ and $R_6$ are independently selected from:
(a) alkyl,
(b) alkenyl,
(c) alkyl terminating in aryl, substituted aryl, heteroaryl or substituted heteroaryl; and
(d) alkenyl terminating in aryl, substituted aryl, heteroaryl or substituted heteroaryl.
In certain embodiments of compounds of formula 17, $R_6$ is

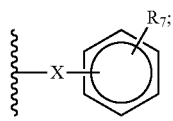

X is an alkyl chain; and
$R_7$ is chosen from halogen, H, phenyl, alkyl, alkoxy, nitro, and $CF_3$.
In other embodiments of compounds of formula 17, $R_4$ is

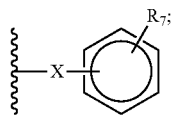

X is an alkyl chain; and
$R_7$ is chosen from halogen, H, phenyl, alkyl, alkoxy, nitro, and $CF_3$.
In one embodiment, any one of the compounds of the invention may be a ligand for an NKT (natural killer T) cell. In another embodiment, the ligand may be in a complex with a CD1 molecule. In another embodiment, the CD1 molecule is a CD1d molecule. In another embodiment, the ligand stimulates NKT cells, which express a CD161+NK marker as well as an invariant T cell antigen receptor (TCR) on the surface thereof.

In another embodiment, the invention provides a composition or vaccine including, inter alia, any one of the compounds of the invention. In another embodiment, the composition or vaccine may include, inter alia, at least one cell population. In another embodiment, the cell population may include, inter alia, NKT cells, antigen presenting cells, or a combination thereof.

In another embodiment, the invention provides a method for stimulating NKT cells, the method includes, inter alia, contacting an NKT cell with any one of the compounds of the invention.

In another embodiment, the invention provides a cell population obtained by any one of the methods of the invention.

In another embodiment, the invention provides a method for stimulating, inhibiting, suppressing or modulating an immune response in a subject, the method includes, inter alia, the step of contacting an NKT cell in the subject with any one of the compounds of the invention.

In another embodiment, the compound according to the invention may be in a complex with a CD1 molecule. In another embodiment, the CD1 molecule may be CD1d. In another embodiment, the complex may be displayed on a dendritic cell. In another embodiment, the complex may be displayed on any antigen presenting cell.

In one embodiment of the invention, the NKT cells secrete a cytokine. In another embodiment the NKT cell may be a Vα24iNKT cell in humans. In another embodiment the NKT cell may be a Vα14i NKT cell in mice.

In one embodiment of the invention, the subject may be immunocompromised. In another embodiment, the subject is infected. In another embodiment, the subject is infected with HIV. In another embodiment, the subject is infected with mycobacteria. In another embodiment, the subject is infected with malaria. In another embodiment, the subject is infected with HIV, mycobacteria, or malaria.

In one embodiment of the invention, the subject is afflicted with cancer. In one embodiment of the invention, the subject is at an elevated risk for cancer. In one embodiment of the invention, the subject has precancerous precursors.

In one embodiment of the invention, the immune response is biased toward Th1 or Th2. In another embodiment, the subject suffers from, or is at an elevated risk for an autoimmune disease. In another embodiment, the biasing of the immune response results in the suppression, inhibition or abrogation of the autoimmune disease. In another embodiment, the subject has an inappropriate or undesirable immune response. In another embodiment, the response is inflammatory. In another embodiment, the inappropriate or undesirable response exacerbates an infection, disease or symptom in the subject.

In another embodiment, the invention provides an adjuvant including, inter alia, any one of the compounds according to the invention.

In another embodiment, the invention provides a method of enhancing immunogenicity of a compound, composition, or vaccine in a subject, the method includes, inter alia, administering to the subject a compound, composition or vaccine further comprising an adjuvant of according to the invention, wherein the adjuvant enhances the immunogenicity of the compound, composition or vaccine.

In another embodiment, the invention provides a method of stimulating or enhancing cytokine production in a subject, the method includes, inter alia, administering to the subject any one of the compounds of the invention, whereby an NKT cell in the subject secretes a cytokine following contact with the compound. In another embodiment, the cytokine may be interferon-γ or Interleukin-4.

Furthermore, in one embodiment, the invention provides a process for the preparation of a compound represented by the structure of formula (4)

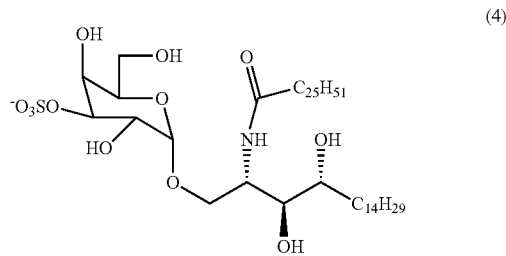

or a pharmaceutically salt thereof, the process includes, inter alia, the step of:
removing the benzyldiene protecting group and hydrogenating of the compound represented by the structure of formula (4a),

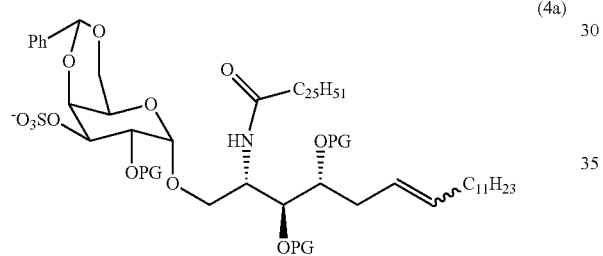

or a salt thereof, wherein PG is a hydroxy protecting group. In another embodiment, the hydroxy protecting group may be benzyl.

In one embodiment of the invention, the compound of formula (4a) may be obtained by a process that includes, inter alia, the step of:
conducting a selective sulfation of the 3″ OH of the galactose moiety of the compound represented by the structure of formula (4b):

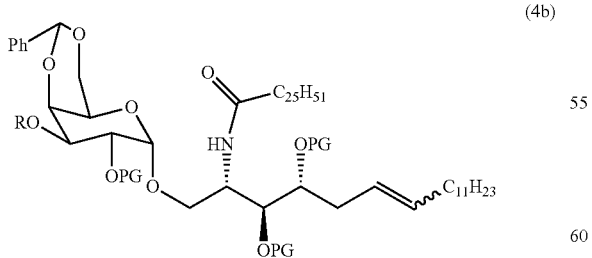

wherein PG is a hydroxy protecting group and R is H. In another embodiment, the hydroxy protecting group may be benzyl.

In one embodiment of the invention, the compound of formula (4b) wherein R is H, may be obtained by a process including, inter alia, the step of removing the levulinyl protecting group of a compound of formula (4b) wherein R is levulinyl, thereby obtaining a compound of formula (4b) wherein R is H.

In one embodiment of the invention, the compound of formula (4b) wherein R is levulinyl may be obtained by a process including, inter alia, the step of:
reacting a compound represented by the structure of formula (4c):

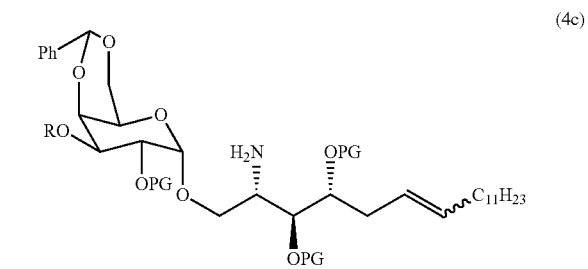

wherein R is H or levulinyl with hexacosanoic acid, thereby obtaining the compound of formula (4b) wherein R is levulinyl.

In one embodiment of the invention, the compound of formula (4c), wherein R is H or levulinyl, may be obtained by a process including, inter alia, the step of:
reducing the azide group of a compound represented by the structure of formula (4d):

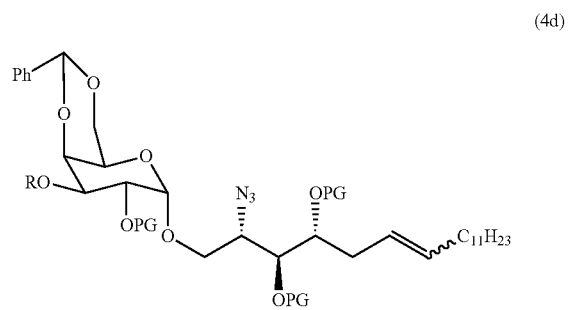

wherein R is levulinyl, thereby obtaining a compound of formula (4c) wherein R is H or levulinyl.

In one embodiment of the invention, the compound of formula (4d) wherein R is levulinyl, may be obtained by a process including, inter alia, the step of:
reacting a compound represented by the structure of formula (4e)

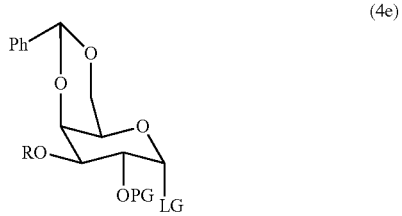

wherein PG is a hydroxy protecting group, LG is a leaving group and R is levulinyl, with a compound represented by the structure of formula (4f)

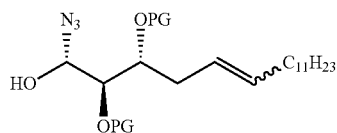
(4f)

wherein PG is a hydroxy protecting group,
to form an alpha glycosidic bond, thereby obtaining the compound of formula (4d) wherein R is levulinyl. In another embodiment, the leaving group may be, inter alia,

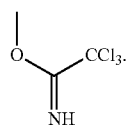

In one embodiment, the invention provides a process for the preparation of a compound represented by the structure of formula (10)

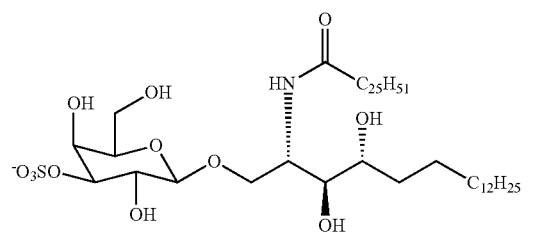
(10)

or a pharmaceutically salt thereof, including, inter alia, the step of:
conducting a selective sulfation of the 3" OH of the galactose moiety of the compound represented by the structure of formula (10a):

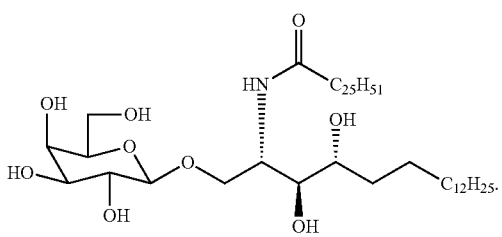
(10a)

In another embodiment, the sulfation may be conducted in the presence of $Bu_2SnO$.

In one embodiment of the invention, the compound of formula (10a) may be obtained by the process including, inter alia, the step of:
removing the hydroxy protecting groups and hydrogenating the compound represented by the structure of formula (10b):

(10b)

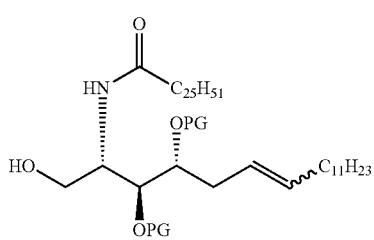

wherein PG and $PG_1$ are hydroxy protecting groups, thereby obtaining the compound of formula (10a). In another embodiment, the PG may be, inter alia, benzyl. In another embodiment, the PG1 may be, inter alia, benzoyl. In one embodiment of the invention, the compound of formula (10b) may be obtained by a process including, inter alia, the step of:
reacting a compound represented by the structure of formula (10c):

(10c)

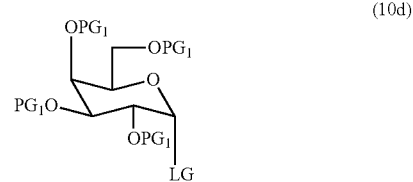

wherein PG is a hydroxy protecting group,
with a compound represented by the structure of formula (10d):

(10d)

wherein $PG_1$ is a hydroxy protecting group and LG is a leaving group, thereby obtaining the compound of formula (10b). In another embodiment, the leaving group may be, inter alia,

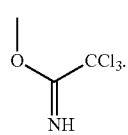

In one embodiment of the invention, the compound of formula (10c) may be obtained by a process including, inter alia, the steps of:
reducing the azide of a compound represented by the structure of formula (10e):

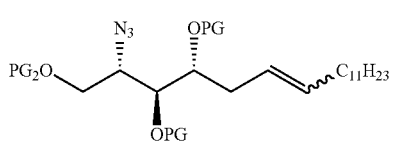
(10e)

wherein PG and PG$_2$ are hydroxy protecting groups;
reacting the resulting amine with hexacosanoic acid; and removing the hydroxy protecting group PG$_2$, thereby obtaining the compound of formula (10c). In another embodiment, the PG$_2$ may be, inter alia, TIPS.

In one embodiment, the invention provides a process for the preparation of a compound represented by the structure of formula (18):

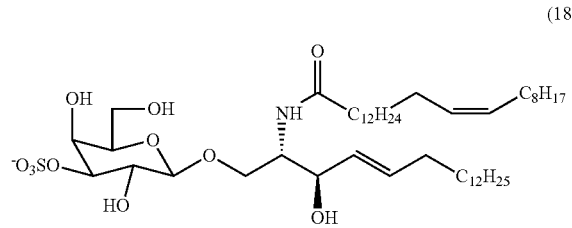
(18)

or a pharmaceutically salt thereof, including, inter alia, the step of:
conducting a selective sulfation of the 3" OH of the galactose moiety of the compound represented by the structure of formula (18a):

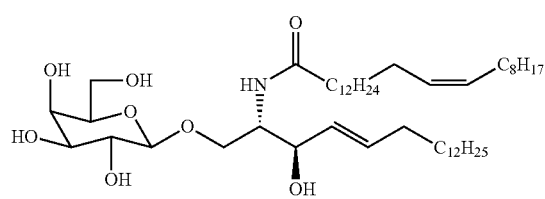
(18a)

thereby obtaining the a compound represented by the structure of formula (18). In another embodiment, the sulfation may be conducted in the presence of Bu$_2$SnO.

In one embodiment of the invention, the compound of formula (18a) may be obtained by the process including, inter alia, the step of:
removing the hydroxy protecting groups of the compound represented by the structure of formula (18b):

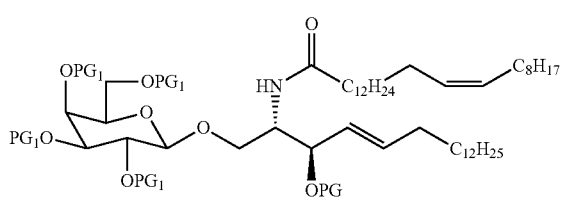
(18b)

wherein PG and PG$_1$ are hydroxy protecting groups, thereby obtaining the compound of formula (18a). In another embodiment, PG may be, inter alia, benzoyl. In another embodiment, PG$_1$ may be, inter alia, benzoyl. In one embodiment of the invention, the compound of formula (18b) may be obtained by a process including, inter alia, the step of:
deprotecting the amine of a compound represented by the structure of formula (18c):

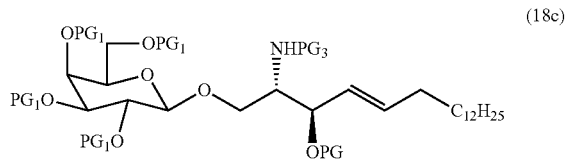
(18c)

wherein PG and PG$_1$ are hydroxy protecting groups, and PG$_3$ is an amino protecting group,
and reacting with nervonic acid, thereby obtaining the compound of formula (18b). In another embodiment, the amino protecting group may be, inter alia, tBoc.

Furthermore, in one embodiment, the invention provides a process for the preparation of a compound represented by the structure of formula (13)

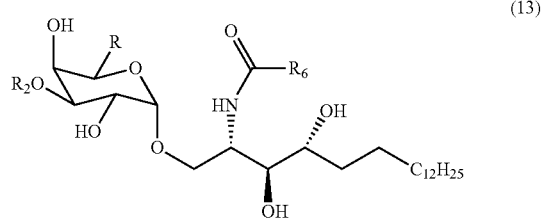
(13)

or a pharmaceutically salt thereof, wherein R is CH$_2$OH and R$_2$ is H, the process including, inter alia, the step of:
removing the benzyldiol protecting group and hydrogenating of the compound represented by the structure of formula (13a),

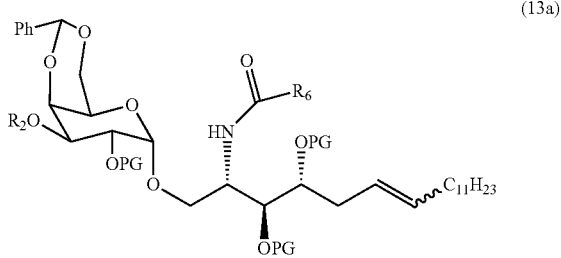
(13a)

or a salt thereof, wherein PG is a hydroxy protecting group, R$_2$ is H. In another embodiment, the hydroxy protecting group may be benzyl.

In one embodiment of the invention, the compound of formula (13a) wherein R$_2$O is SO$_3^-$, may be obtained by a process including, inter alia, the step of conducting a selective sulfation of the 3" OH of the galactose moiety of the compound represented by the structure of formula (13a).

In one embodiment of the invention, the compound of formula (13a) wherein R$_2$ is H, may be obtained by a process including, inter alia, the step of removing the levulinyl protecting group of a compound of formula (13b) wherein R$_2$ is levulinyl, thereby obtaining a compound of formula (13a) wherein R$_2$ is H.

In one embodiment of the invention, the compound of formula (13b) wherein R$_2$ is levulinyl may be obtained by a process including, inter alia, the step of:

reacting a compound represented by the structure of formula (13c):

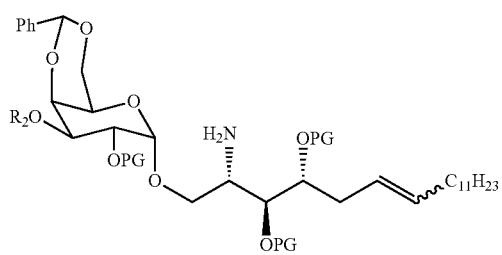
(13c)

wherein R$_2$ is levulinyl with an acid form of R$_6$, thereby obtaining the compound of formula (13b) wherein R$_2$ is levulinyl.

In one embodiment of the invention, the compound of formula (13c), wherein R$_2$ is levulinyl, may be obtained by a process including, inter alia, the step of:

reducing the azide group of a compound represented by the structure of formula (13d):

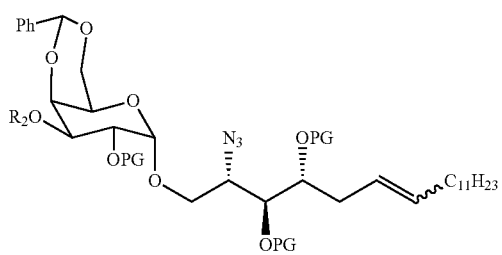
(13d)

wherein R$_2$ is levulinyl, thereby obtaining a compound of formula (13c).

In one embodiment of the invention, the compound of formula (13d) wherein R$_2$ is levulinyl, may be obtained by a process including, inter alia, the step of:

reacting a compound represented by the structure of formula (13e)

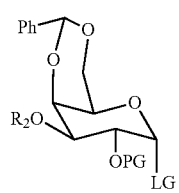
(13e)

wherein PG is a hydroxy protecting group, LG is a leaving group and R$_2$ is levulinyl, with a compound represented by the structure of formula (13f)

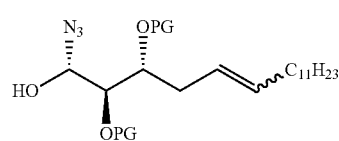
(13f)

wherein PG is a hydroxy protecting group, to form an alpha glycosidic bond, thereby obtaining the compound of formula (13d) wherein R$_2$ is levulinyl. In another embodiment, the leaving group may be, inter alia,

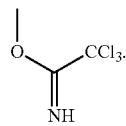

In one embodiment, the invention provides a process for the preparation of a compound represented by the structure of formula (14)

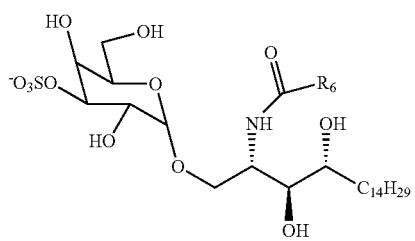
(14)

or a pharmaceutically salt thereof, including, inter alia, the step of:

conducting a selective sulfation of the 3" OH of the galactose moiety of the compound represented by the structure of formula (13):

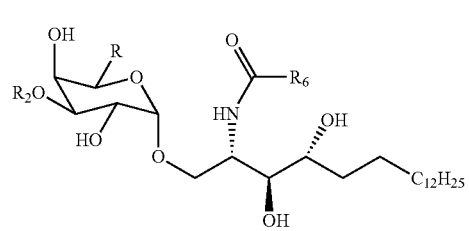
(13)

Wherein R$_2$ is H and R is CH$_2$OH.

In another embodiment, the sulfation may be conducted in the presence of Bu$_2$SnO.

In one embodiment of the invention, the compound of formula (13) may be obtained by the process including, inter alia, the step of:

removing the hydroxy protecting groups and hydrogenating the compound represented by the structure of formula (13g):

(13g)

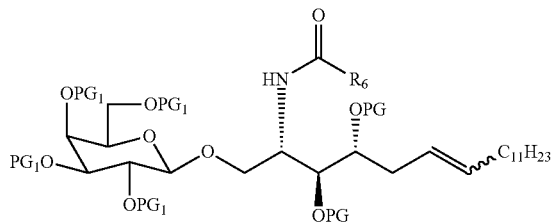

wherein PG and PG$_1$ are hydroxy protecting groups, thereby obtaining the compound of formula (13), wherein R$_2$ is H and R is CH$_2$OH. In another embodiment, the PG may be, inter alia, benzyl. In another embodiment, the PG1 may be, inter alia, benzoyl. In one embodiment of the invention, the compound of formula (13g) may be obtained by a process including, inter alia, the step of:

reacting a compound represented by the structure of formula (13h):

(13h)

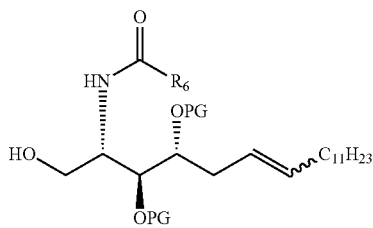

wherein PG is a hydroxy protecting group, with a compound represented by the structure of formula (13i):

(13i)

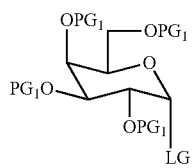

wherein PG$_1$ is a hydroxy protecting group and LG is a leaving group, thereby obtaining the compound of formula (13g). In another embodiment, the leaving group may be, inter alia,

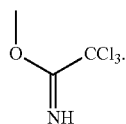

In one embodiment of the invention, the compound of formula (13h) may be obtained by a process comprising the steps of:

reducing the azide of a compound represented by the structure of formula (13j):

(13j)

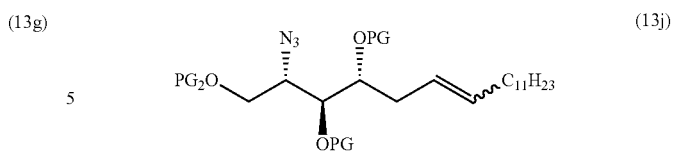

wherein PG and PG$_2$ are hydroxy protecting groups;

reacting the resulting amine with an acid form of R$_6$; and removing the hydroxy protecting group PG$_2$, thereby obtaining the compound of formula (13h). In another embodiment, the PG$_2$ may be, inter alia, TIPS.

In one embodiment of the invention, the compound of formula (13g) may be obtained by a process including, inter alia, the step of:

deprotecting the amine of a compound represented by the structure of formula (13k):

(13k)

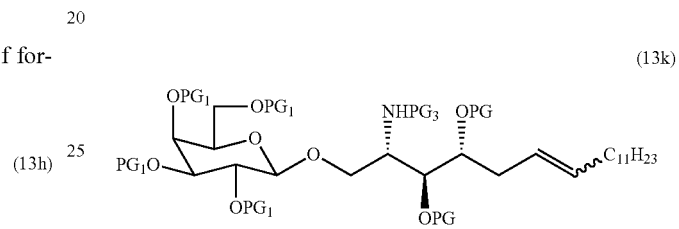

wherein PG and PG$_1$ are hydroxy protecting groups, and PG$_3$ is an amino protecting group, and reacting with an acid form of R$_6$, thereby obtaining the compound of formula (13g). In another embodiment, the amino protecting group may be, inter alia, tBoc.

In one embodiment of the invention, an "alkyl" group refers to a saturated aliphatic hydrocarbon, including straight-chain, branched-chain and cyclic alkyl groups. In one embodiment, the alkyl group has 1-30 carbons. In another embodiment, the alkyl group has 1-25 carbons. In another embodiment, the alkyl group has 1-20 carbons. In another embodiment, the alkyl group has 1-10 carbons. In another embodiment, the alkyl group has 1-5 carbons. In another embodiment, the alkyl group has 10-25 carbons. In another embodiment, the alkyl group has 15-25 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

The term alkyl as used throughout the specification and claims includes both "unsubstituted alkyls" and/or "substituted alkyls", the latter of which may refer to alkyl moieties having substituents replacing a hydrogen on one or more carbons of the hydrocarbon backbone. Such substituents may include, for example, a halogen, a hydroxyl, an alkoxyl, a silyloxy, a carbonyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain may themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —CF$_3$, and —CN. Of course other substituents may be applied. In another embodiment, cycloalkyls may be further substituted with alkyls, alkenyls, alkoxys, thioalkyls, aminoalkyls, carbonyl-substituted alkyls, $CF_3$, and CN. Of course other substituents may be applied. In certain embodiments, the alkyl will be otherwise unsubstituted but will terminate in aryl, substituted aryl, heteroaryl or substituted heteroaryl. The term "unsaturated alkyl" will appear herein interchangeably with the term "alkenyl"; both refer to the same thing. Thus the residue $-CH=CH(CH_2)_{10}CH_3$ can be called either "unsaturated alkyl" or "alkenyl".

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Lower-alkoxy refers to groups containing one to four carbons. Methoxy is preferred. For the purpose of this application, alkoxy and lower alkoxy include methylenedioxy and ethylenedioxy.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

The term "halogen" means fluorine, chlorine, bromine or iodine.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The abbreviations Me, Et, Ph, Tf, Ts and Ms represent methyl, ethyl, phenyl, trifluoromethanesulfonyl, toluensulfonyl and methanesulfonyl respectively. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations" is incorporated herein by reference.

As used herein, and as would be understood by the person of skill in the art, the recitation of "a compound" is intended to include salts, solvates and inclusion complexes of that compound. For example, the sulfonate ($SO_3^-$) residue will often appear in formulae herein. As will be understood by the person of skill in the art, there is an implication of a counterion, which can be $H^+$ (i.e. the acid form) or any cation discussed below. Cations of alkali metals and alkaline earth metals, as well as ammonium cations, are common. Similarly the carboxylate may be written COOH, but the salt form $COO^-M^+$ is included within the scope of the invention.

Unless chirality is specifically indicated, claims to a compound include any stereoisomeric form, or a mixture of any such forms of that compound in any ratio. The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds contain an acidic function (e.g. a carboxylic acid or sulfonic acid residue, suitable pharmaceutically acceptable base addition salts for the compounds of the present invention include metallic salts made from aluminum, calcium, lithium, magnesium, potassium, sodium and zinc, or organic salts made from lysine, N,N'-dibenzylethylenediamine, chloroprocaine, choline, diethanolamine, ethylenediamine, meglumine (N-methylglucamine) and procaine.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

According to embodiments of the invention, the phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. Of course other appropriate protecting groups may be used.

In one embodiment of the invention, the protecting group may be, inter alia, a hydroxy protecting group. In one embodiment of the invention, the hydroxy protecting group may be, inter alia, an alkyl, aryl, aralkyl, silyl or acyl radical. In another embodiment, the protecting group may be, inter alia, trimethylsilyl, triethylsilyl, tert-butyldimethylsilyl (TBS), triisopropylsilyl (TIPS), or tert-butyldiphenylsilyl. Of course, any other appropriate protecting group may be used. In one embodiment, the aralkyl may be unsubstituted or substituted. In another embodiment, the aralkyl may be, inter alia, arylmethyl. In another embodiment, the protecting group may be, inter alia, benzyl. In another embodiment, the protecting group may be, inter alia, methoxybenzyl. In another embodiment, the methoxybenzyl may be, inter alia, para-methoxybenzyl.

In one embodiment of the invention, the amino protective group may be any of amino protective group (see for example "Protection for the amino group" in T. W. Green & P. G. M. Wuts, Protective groups in organic synthesis, 3rd Ed., 1999, 494-653).

In one embodiment of the invention, the protecting group may be, inter alia, an amino protecting group. In one embodiment of the invention, the amino protecting group may be, inter alia, carbamate, an amide or an N-sulfonylamide. In another embodiment, the amino protecting group may be, inter alia, benzyloxycarbonyl (Cbz), 9-fluorenylmethyloxycarbonyl (Fmoc), t-butyloxycarbonyl, (tBoc), biphenylisopropyloxycarbonyl, t-amyloxycarbonyl, isobornyloxycarbonyl, alpha-dimethyl-3,5-dimethoxybenzyloxycarbonyl or 2-cyano-t-butyloxycarbonyl. In another embodiment, the amino protecting group (PG) may be, inter alia, benzyloxycarbonyl (Cbz).

Furthermore, in one embodiment, the invention provides a pharmaceutical composition including, inter alia, any one of the compounds of this invention or any combination thereof, together with one or more pharmaceutically acceptable excipients.

Furthermore, in one embodiment, the invention provides a method for stimulating, inhibiting, suppressing or modulating an immune response in a subject, the method may include, inter alia, administering to a subject any one of the compounds of this invention or any combination thereof.

Furthermore, in one embodiment, the invention provides a method for stimulating, inhibiting, suppressing or modulating an immune response in a subject, the method includes, inter alia, administering to a subject a pharmaceutical composition including, inter alia, any one of the compounds of this invention or any combination thereof, together with one or more pharmaceutically acceptable excipients.

Furthermore, in one embodiment, "pharmaceutical composition" can mean a therapeutically effective amount of one or more compounds of the present invention together with suitable excipients and/or carriers useful for stimulating, inhibiting, suppressing or modulating an immune response in a subject. In one embodiment, "therapeutically effective amount" may refer to that amount that provides a therapeutic effect for a given condition and administration regimen. In one embodiment, such compositions can be administered by any method known in the art.

In one embodiment, the compositions of the present invention are formulated as oral or parenteral dosage forms, such as uncoated tablets, coated tablets, pills, capsules, powders, granulates, dispersions or suspensions. In another embodiment, the compositions of the present invention are formulated for intravenous administration. In another embodiment, the compounds of the present invention are formulated in ointment, cream or gel form for transdermal administration. In another embodiment, the compounds of the present invention are formulated as an aerosol or spray for nasal application. In another embodiment, the compositions of the present invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents Parenteral and intravenous forms should also include minerals and other materials to make them compatible with the type of injection or delivery system chosen. Of course, other excipients may also be used.

BRIEF DESCRIPTION OF THE DRAWINGS

FIG. 4 demonstrates (a) the preparation of compound XVIII, according to embodiments of the invention; (b) the preparation of compound 10, according to embodiments of the invention.

FIG. 6 schematically depicts the synthesis of sphingosine, according to embodiments of the invention, as conducted herein. Reagents and conditions; a) C2H3MgBr, THF, Anti- Syn 3.5:1 61%; b) (i) Grubbs catalyst 2nd generation, CH2Cl2, Pentadecene, 71%; (ii) BzCl, pyridine, 90%; (iii) Amberlyst 15 H+ form, MeOH 70%.

DETAILED DESCRIPTION OF THE PRESENT INVENTION

Figure 1:
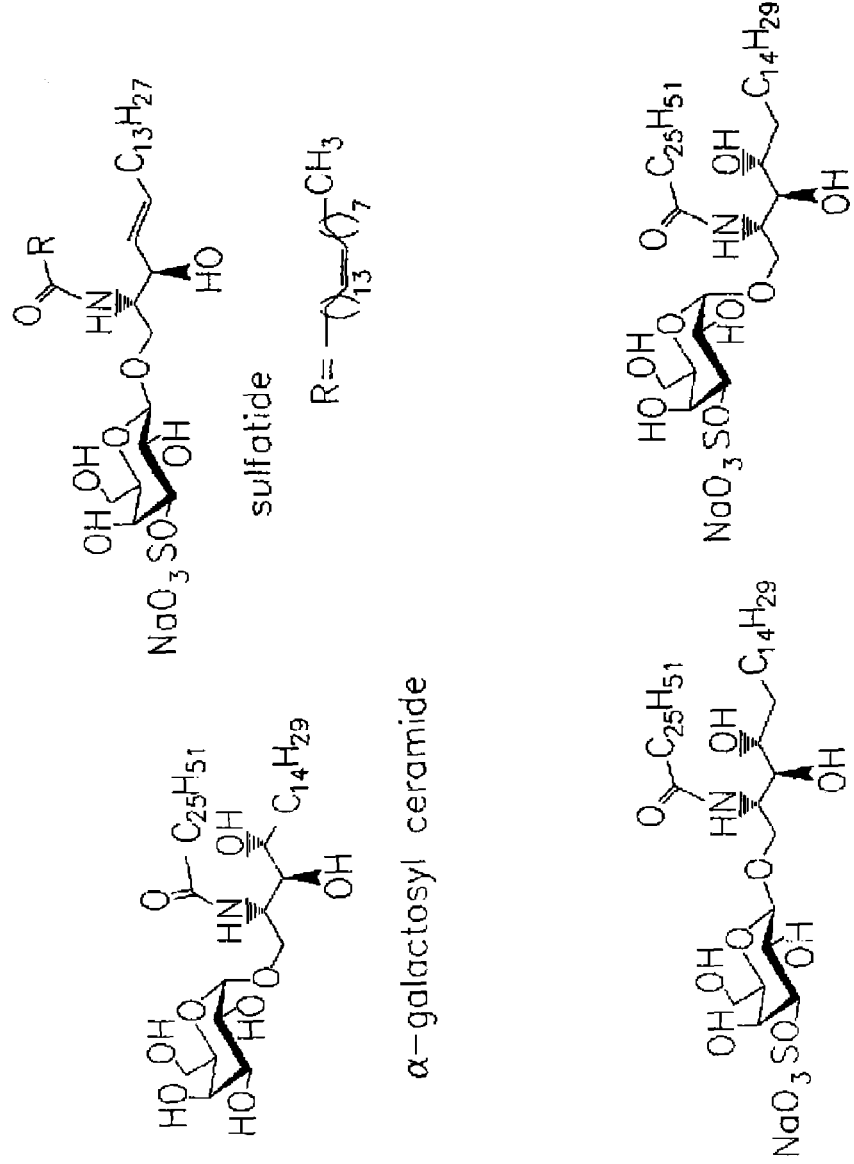
FIG. 1 demonstrates structures of α-galactosylceramide, sulfatide and 3-O-sulfo-α/β-galactosylceramides 10, 24, according to embodiments of the invention.

This invention provides, in one embodiment, a compound represented by the structure of formula 1:

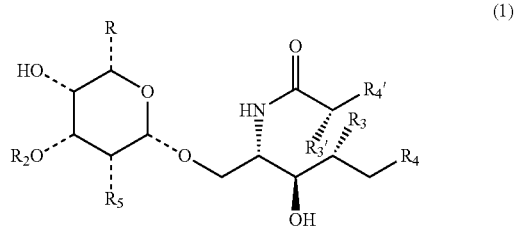

wherein, R=COOR$_1$ or CH$_2$OR$_1$;
R$_1$=H or an alkyl group;
R$_2$=H or SO$_3^-$;
R$_3$=H or OH;
R$_3$'=H or OH;
R$_4$ and R$_4$' are independently chosen from
(a) H,
(b) alkyl;
(c) alkenyl; and
(d) oxaalkyl;
R$_5$=OH, acetamido or a halogen atom;
or a pharmaceutically acceptable salt thereof,
wherein if R=CH$_2$OR$_1$, R$_2$=H, R$_3$ is OH and R$_3$' is H, then one of the following is true:

(i) $R_5$=acetamido, halogen atom or OH in an axial position;
(ii) $R_4$=H, or unsaturated or saturated alkyl chain having 9 carbon atoms or fewer; or
(iii) $R_4'$=H, or unsaturated or saturated alkyl chain having 20 carbon atoms or fewer.

In another embodiment, this invention provides a compound represented by the structure of formula 2:

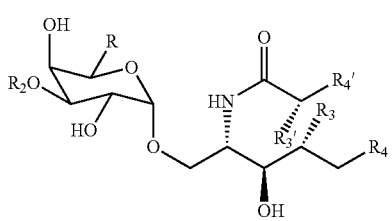

(2)

wherein R=$COOR_1$ or $CH_2OR_1$;
$R_1$=H or an alkyl group;
$R_2$=H or $SO_3^-$;
$R_3$=H or OH;
$R_3'$=H or OH; and
$R_4$=H, unsaturated or saturated, alkyl group; and
$R_4'$=H, unsaturated or saturated, alkyl group;
or a pharmaceutically acceptable salt thereof,
wherein if R=$CH_2OR_1$, $R_2$=H, $R_3$ is OH and $R_3'$ is H, then one of the following is true:
(i) $R_4$=H, or unsaturated or saturated alkyl chain having 9 carbon atoms or fewer;
or (ii) $R_4'$=H, or unsaturated or saturated alkyl chain having 20 carbon atoms or fewer.

In one embodiment, the alkyl chain of $R_4$ has 1 carbon atom, in another embodiment, the alkyl chain of $R_4$ has between 1-5, or in another embodiment, 2-6, or in another embodiment, 3-7, or in another embodiment, 4-8, or in another embodiment 5-9 carbon atoms. In one embodiment, the alkyl chain of $R_4$ has 10-25 carbon atom, in another embodiment, the alkyl chain of $R_4$ has between 10-15 carbon atoms.

In another embodiment, the alkyl chain of $R_4'$ has 1 carbon atom, in another embodiment, the alkyl chain of $R_4'$ has between 1-10, or in another embodiment, 10-15, or in another embodiment, 5-13, or in another embodiment, 8-15, or in another embodiment 10-25 carbon atoms or, in another embodiment, between 20-30 carbon atoms.

In another embodiment, this invention provides a compound represented by the structure of formula 3:

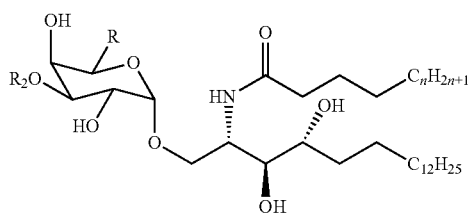

(3)

wherein, R=$COOR_1$ or $CH_2OR_1$;
$R_1$=H or an alkyl group;
$R_2$=$SO_3^-$; and
n=integer;
or a pharmaceutically acceptable salt thereof.

In another embodiment, n is an integer ranging from 1-5, or, in another embodiment, between 5-10, or in another embodiment, 10-15, or in another embodiment, 10-20, or in another embodiment, 1-15, or in another embodiment 15-25 carbon atoms or, in another embodiment, between 10-30.

In another embodiment, this invention provides a compound represented by the structure of formula 4:

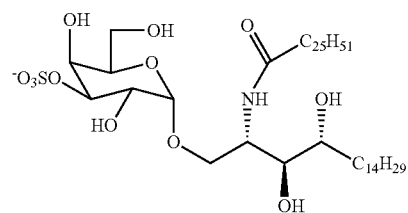

(4)

or a pharmaceutically acceptable salt thereof.

In another embodiment, the salt may be, inter alia, a sodium salt.

In another embodiment, this invention provides a compound represented by the structure of formula 5:

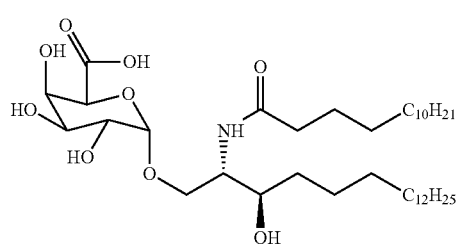

(5)

In another embodiment, this invention provides a compound represented by the structure of formula 6:

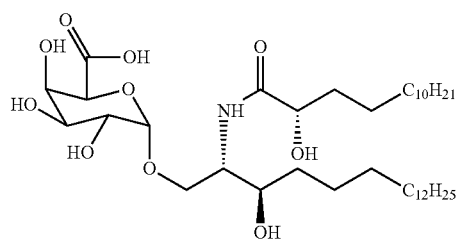

(6)

In another embodiment, this invention provides a compound represented by the structure of formula 7:

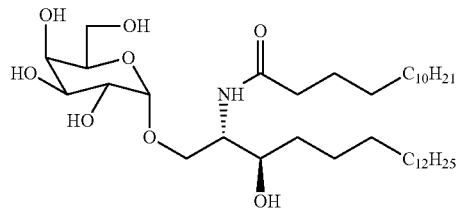

(7)

In another embodiment, this invention provides a compound represented by the structure of formula 8:

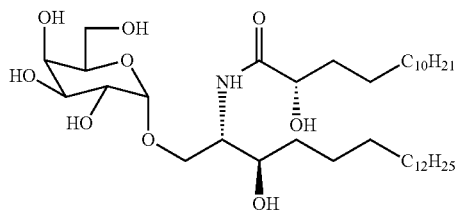
(8)

In one embodiment, this invention provides a compound represented by the structure of formula 9:

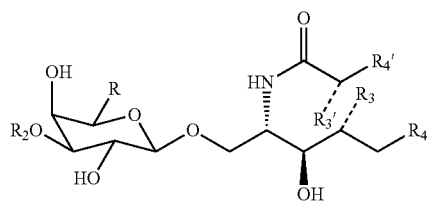
(9)

wherein, R=COOR$_1$ or CH$_2$OR$_1$

R$_1$=H or an alkyl group;

R$_2$=H or SO$_3^-$;

R$_3$=OH;

R$_3$'=H or OH; and

R$_4$=H, unsaturated or saturated, alkyl group; and

R$_4$'=H, unsaturated or saturated, alkyl group;

or a pharmaceutically acceptable salt thereof,
wherein if R=CH$_2$OR$_1$, R$_2$=H, R$_3$ is OH and R$_3$' is H, then one of the following is true:

(i) R$_4$=H, or unsaturated or saturated alkyl chain having 9 carbon atoms or fewer; or (ii) R$_4$'=H, or unsaturated or saturated alkyl chain having 20 carbon atoms or fewer.

In another embodiment, this invention provides a compound represented by the structure of formula 10:

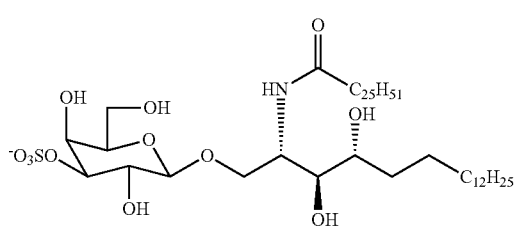
(10)

or a pharmaceutically acceptable salt thereof. In another embodiment, the salt may be, inter alia, a sodium salt.

In still another embodiment, this invention provides a compound represented by the structure of formula 17:

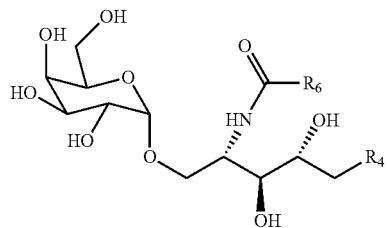
(17)

wherein
R$_4$ and R$_6$ are independently selected from:
(a) alkyl,
(b) alkenyl,
(c) alkyl terminating in aryl, substituted aryl, heteroaryl or substituted heteroaryl; and
(d) alkenyl terminating in aryl, substituted aryl, heteroaryl or substituted heteroaryl.

In certain embodiments of compounds of formula 17,
R$_6$ is

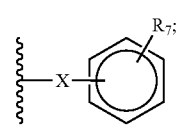

X is an alkyl chain; and
R$_7$ is chosen from halogen, H, phenyl, alkyl, alkoxy, nitro, and CF$_3$.

In other embodiments of compounds of formula 17,
R$_4$ is

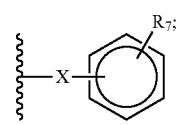

X is an alkyl chain; and
R$_7$ is chosen from halogen, H, phenyl, alkyl, alkoxy, nitro, and CF$_3$.

Furthermore, in one embodiment, the invention provides a process for the preparation of a compound represented by the structure of formula (4)

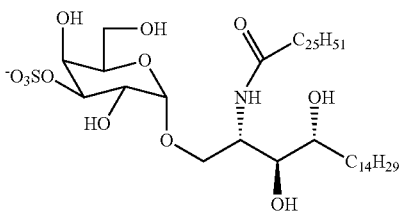
(4)

or a pharmaceutically salt thereof, the process including, inter alia, the step of:
removing the benzyldiene protecting group and hydrogenating of the compound represented by the structure of formula (4a), (4a)

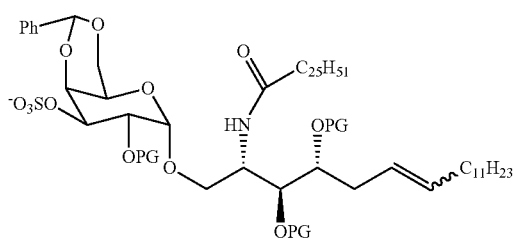

or a salt thereof, wherein PG is a hydroxy protecting group. In another embodiment, the hydroxy protecting group may be benzyl.

In one embodiment of the invention, the compound of formula (4a) may be obtained by a process including, inter alia, the step of:

conducting a selective sulfation of the 3" OH of the galactose moiety of the compound represented by the structure of formula (4b):

(4b)

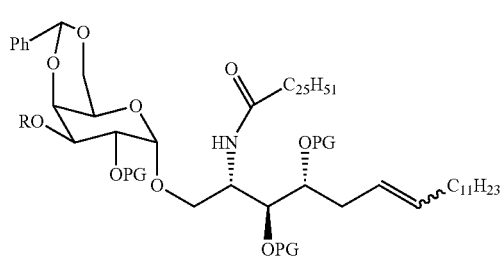

wherein PG is a hydroxy protecting group and R is H. In another embodiment, the hydroxy protecting group may be benzyl.

In one embodiment of the invention, the compound of formula (4b) wherein R is H, may be obtained by a process including, inter alia, the step of removing the levulinyl protecting group of a compound of formula (4b) wherein R is levulinyl, thereby obtaining a compound of formula (4b) wherein R is H.

In one embodiment of the invention, the compound of formula (4b) wherein R is levulinyl may be obtained by a process including, inter alia, the step of:

reacting a compound represented by the structure of formula (4c):

(4c)

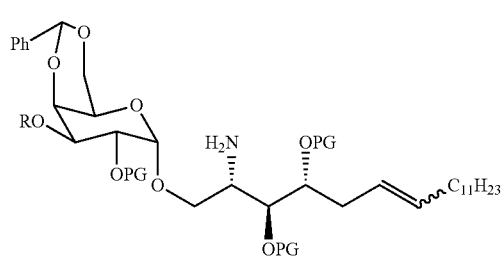

wherein R is H or levulinyl with hexacosanoic acid, thereby obtaining the compound of formula (4b) wherein R is levulinyl.

In one embodiment of the invention, the compound of formula (4c), wherein R is H or levulinyl, may be obtained by a process including, inter alia, the step of:

reducing the azide group of a compound represented by the structure of formula (4d):

(4d)

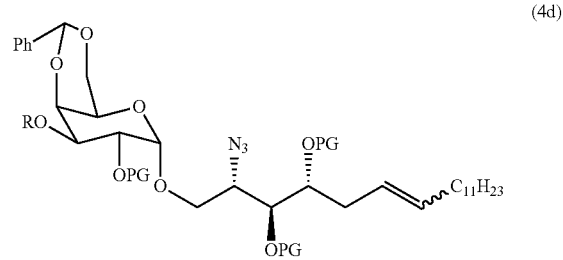

wherein R is levulinyl, thereby obtaining a compound of formula (4c) wherein R is H or levulinyl.

In one embodiment of the invention, the compound of formula (4d) wherein R is levulinyl, may be obtained by a process including, inter alia, the step of:

reacting a compound represented by the structure of formula (4e)

(4e)

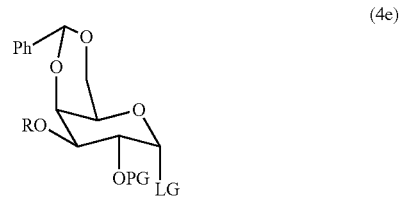

wherein PG is a hydroxy protecting group, LG is a leaving group and R is levulinyl, with a compound represented by the structure of formula (4f)

(4f)

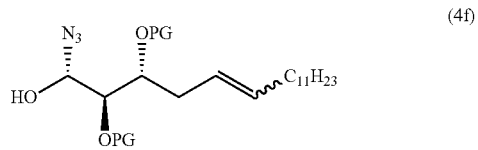

wherein PG is a hydroxy protecting group, to form an alpha glycosidic bond, thereby obtaining the compound of formula (4d) wherein R is levulinyl. In another embodiment, the leaving group may be, inter alia,

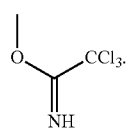

In one embodiment, the invention provides a process for the preparation of a compound represented by the structure of formula (10)

(10)

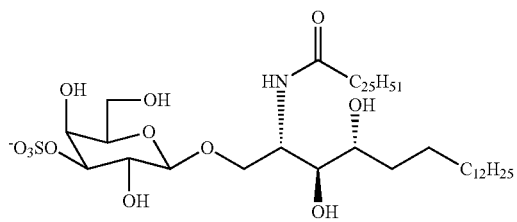

or a pharmaceutically salt thereof, including, inter alia, the step of:
conducting a selective sulfation of the 3" OH of the galactose moiety of the compound represented by the structure of formula (10a):

(10a)

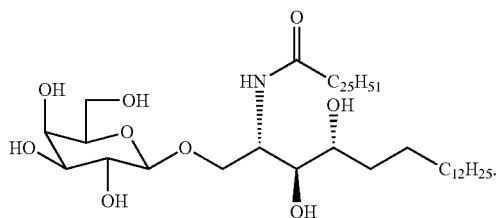

In another embodiment, the sulfation may be conducted in the presence of $Bu_2SnO$.

In one embodiment of the invention, the compound of formula (10a) may be obtained by the process including, inter alia, the step of:
removing the hydroxy protecting groups and hydrogenating the compound represented by the structure of formula (10b):

(10b)

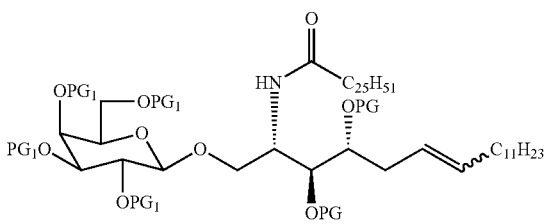

wherein PG and $PG_1$ are hydroxy protecting groups, thereby obtaining the compound of formula (10a). In another embodiment, the PG may be, inter alia, benzyl. In another embodiment, the PG1 may be, inter alia, benzoyl. In one embodiment of the invention, the compound of formula (10b) may be obtained by a process including, inter alia, the step of:
reacting a compound represented by the structure of formula (10c):

(10c)

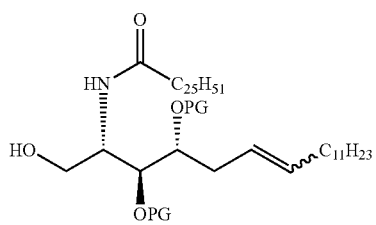

wherein PG is a hydroxy protecting group,
with a compound represented by the structure of formula (10d):

(10d)

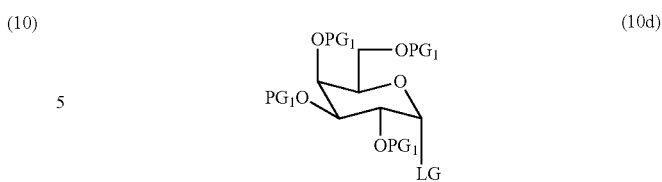

wherein $PG_1$ is a hydroxy protecting group and LG is a leaving group, thereby obtaining the compound of formula (10b). In another embodiment, the leaving group may be, inter alia,

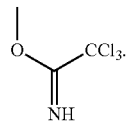

In one embodiment of the invention, the compound of formula (10c) may be obtained by a process comprising the steps of:
reducing the azide of a compound represented by the structure of formula (10e):

(10e)

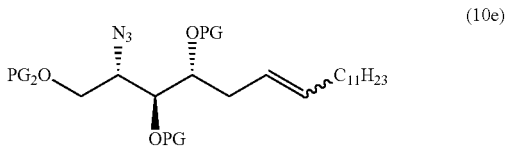

wherein PG and $PG_2$ are hydroxy protecting groups;
reacting the resulting amine with hexacosanoic acid; and removing the hydroxy protecting group $PG_2$, thereby obtaining the compound of formula (10c). In another embodiment, the $PG_2$ may be, inter alia, TIPS.

In one embodiment, the invention provides a process for the preparation of a compound represented by the structure of formula (11):

(11)

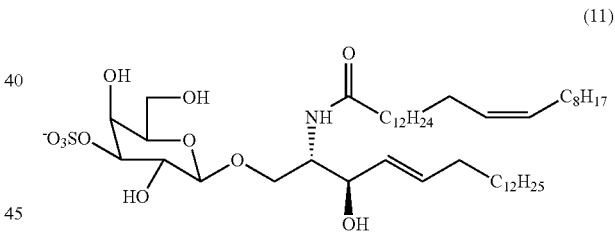

or a pharmaceutically salt thereof, including, inter alia, the step of:
conducting a selective sulfation of the 3" OH of the galactose moiety of the compound represented by the structure of formula (11a):

(11a)

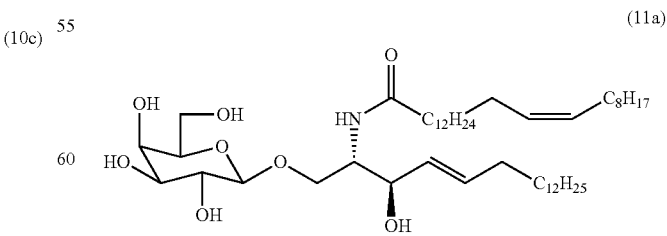

thereby obtaining the a compound represented by the structure of formula (10). In another embodiment, the sulfation may be conducted in the presence of $Bu_2SnO$.

In one embodiment of the invention, the compound of formula (11a) may be obtained by the process including, inter alia, the step of:

removing the hydroxy protecting groups of the compound represented by the structure of formula (11b):

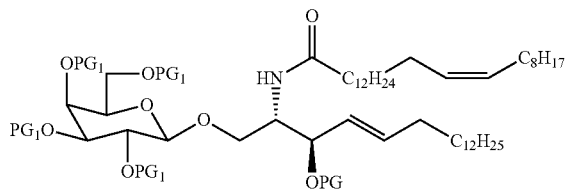

(11b)

wherein PG and $PG_1$ are hydroxy protecting groups, thereby obtaining the compound of formula (11a). In another embodiment, PG may be, inter alia, benzoyl. In another embodiment, $PG_1$ may be, inter alia, benzoyl.

In one embodiment of the invention, the compound of formula (10b) may be obtained by a process including, inter alia, the step of:

deprotecting the amine of a compound represented by the structure of formula (11c):

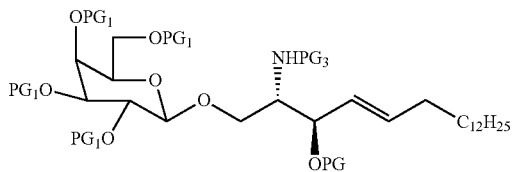

(11c)

wherein PG and $PG_1$ are hydroxy protecting groups, and $PG_3$ is an amino protecting group, and reacting with nervonic acid, thereby obtaining the compound of formula (11b). In another embodiment, the amino protecting group may be, inter alia, tBoc.

In one embodiment, any one of the compounds of the invention may be a ligand for an NKT (natural killer T) cell. In another embodiment, the ligand may be in a complex with a CD1 molecule. In another embodiment, the CD1 molecule is a CD1d molecule. In another embodiment, the ligand stimulates NKT cells, which express a CD161+ NK marker as well as an invariant T cell antigen receptor (TCR) on the surface thereof.

In another embodiment, the invention provides a composition or vaccine including, inter alia, any one of the compounds of the invention. In another embodiment, the composition or vaccine may include, inter alia, at least one cell population. In another embodiment, the cell population may include, inter alia, NKT cells, antigen presenting cells, or a combination thereof.

In another embodiment, the invention provides a method for stimulating NKT cells, the method including, inter alia, contacting an NKT cell with any one of the compounds of the invention.

In another embodiment, the invention provides a cell population obtained by any one of the methods of the invention.

In another embodiment, the invention provides a method for stimulating, inhibiting, suppressing or modulating an immune response in a subject, the method includes, inter alia, the step of contacting an NKT cell in the subject with any one of the compounds of the invention.

In another embodiment, the compound according to the invention may be in a complex with a CD1 molecule. In another embodiment, the CD1 molecule may be CD1d. In another embodiment, the complex may be displayed on a dendritic cell. In another embodiment, the complex may be displayed on any antigen presenting cell.

In one embodiment of the invention, the NKT cells secrete a cytokine. In another embodiment the NKT cell may be a Vα24iNKT cell in humans. In another embodiment the NKT cell may be a Vα14i NKT cell in mice.

In one embodiment of the invention, the subject may be immunocompromised. In another embodiment, the subject is infected. In another embodiment, the subject is infected with HIV. In another embodiment, the subject is infected with mycobacteria. In another embodiment, the subject is infected with malaria. In another embodiment, the subject is infected with HIV, mycobacteria, or malaria.

In one embodiment of the invention, the subject is afflicted with cancer. In one embodiment of the invention, the subject is at an elevated risk for cancer. In one embodiment of the invention, the subject has precancerous precursors.

In one embodiment of the invention, the immune response is biased toward Th1 or Th2. In another embodiment, the subject suffers from, or is at an elevated risk for an autoimmune disease. In another embodiment, the biasing of the immune response results in the suppression, inhibition or abrogation of the autoimmune disease. In another embodiment, the subject has an inappropriate or undesirable immune response. In another embodiment, the response is inflammatory. In another embodiment, the inappropriate or undesirable response exacerbates an infection, disease or symptom in the subject.

In another embodiment, the invention provides an adjuvant including, inter alia, any one of the compounds according to the invention.

In another embodiment, the invention provides a method of enhancing immunogenicity of a compound, composition, or vaccine in a subject, the method includes, inter alia, administering to the subject a compound, composition or vaccine further comprising an adjuvant of according to the invention, wherein the adjuvant enhances the immunogenicity of the compound, composition or vaccine.

In another embodiment, the invention provides a method of stimulating or enhancing cytokine production in a subject, the method includes, inter alia, administering to the subject any one of the compounds of the invention, whereby an NKT cell in the subject secretes a cytokine following contact with the compound. In another embodiment, the cytokine may be interferon-γ or Interleukin-4.

In another embodiment, this invention provides an NK T cell obtained via contacting an NK T cell with a compound of this invention. In one embodiment, such contact is in the presence of an antigen presenting cell, which in another embodiment expresses a CD1 molecule, wherein the compound, or a fragment thereof, is displayed in the context of the CD 1 molecule.

In one embodiment, the phrase "NKT cell" or "Natural Killer cell", refers to a T cell population that causes, stimulates or contributes to cytokine production, and/or in another embodiment, is cytotoxic. In one embodiment, the NKT cells are a homogenous population, or in another embodiment, a heterogeneous population.

NKT cells are an exceptional subset of mature lymphocytes that bear both NK and T cell receptors. Murine NKT cells express NK1.1 and TCRαβ receptors and are especially dense in the bone marrow and liver. The cells may express a very limited TCR repertoire, which may include an invariant α-chain. The ligand for NKT cells may be non-polymorphic, and a non-classical MHC class I molecule may present a specific antigen processed via a TAP (transporter associated with antigen processing)-independent pathway.

In one embodiment, the antigen is presented in the context of a CD1 molecule, which in one embodiment is CD1d. Activated NK T cells may display an NK-like perforin-dependent cytotoxicity against various cells, including tumor cells or cell lines and inhibit tumor metastasis, among other applications, as is described further hereinbelow, and representing embodiments of the methods of this invention.

The T cells of this invention may express CD161 and Vα24i TCR on their cell surface. In one embodiment, the T cells may be classified as CD 161$^{high}$ expressors, or in another embodiment, the T cells may be classified as CD 161$^{low}$ expressors, or in another embodiment, a combination thereof.

It is to be understood that the NK T cells of this invention, and those obtained via the methods of this invention, may express any number or combination of cell surface markers, as described herein, and as is well known in the art, and are to be considered as part of this invention.

In one embodiment, the T cell subpopulation, are "invariant NK T cells," which may represent a major fraction of the mature T cells in thymus, the major T cell subpopulation in murine liver, and/or up to 5% of splenic T cells.

In another embodiment, the T cell subpopulation may be "non-invariant NK T cells", which may comprise human and mouse bone marrow and human liver T cell populations that are, for example, CD1d-reactive noninvariant T cells which express diverse TCRs, and which can also produce a large amount of IL-4 and IFN-γ.

In one embodiment, the NKT cells of this invention are obtained by positive selection for expression of CD161 and Vα24i TCR, and in another embodiment, the T cells may be obtained via negative selection procedures, as are well known in the art.

In one embodiment, the NK T cells of this invention may be obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells may be obtained. In one embodiment, the NK T cells are obtained from human sources, which may be, in another embodiment, from human fetal, neonatal, child, or adult sources. In another embodiment, the NK T cells of this invention may be obtained from animal sources, such as, for example, porcine or simian, or any other animal of interest. In another embodiment, the NK T cells of this invention may be obtained from subjects that are normal, or in another embodiment, diseased, or in another embodiment, susceptible to a disease of interest.

In one embodiment, the T cells and/or cells, as described further hereinbelow, of this invention are isolated from tissue, and, in another embodiment, an appropriate solution may be used for dispersion or suspension, toward this end. In another embodiment, T cells and/or cells, as described further hereinbelow, of this invention may be cultured in solution.

Such a solution may be, in another embodiment, a balanced salt solution, such as normal saline, PBS, or Hank's balanced salt solution, or others, each of which represents another embodiment of this invention. The solution may be supplemented, in other embodiment, with fetal calf serum, bovine serum albumin (BSA), normal goat serum, or other naturally occurring factors, and, in another embodiment, may be supplied in conjunction with an acceptable buffer. The buffer may be, in other embodiments, HEPES, phosphate buffers, lactate buffers, or the like, as will be known to one skilled in the art.

In another embodiment, the solution in which the T cells or cells of this invention may be placed is in medium is which is serum-free, which may be, in another embodiment, commercially available, such as, for example, animal protein-free base media such as X-VIVO 10™ or X-VIVO 15™ (BioWhittaker, Walkersville, Md.), Hematopoietic Stem Cell-SFM media (GibcoBRL, Grand Island, N.Y.) or any formulation which promotes or sustains cell viability. Serum-free media used, may, in another embodiment, be as those described in the following patent documents: WO 95/00632; U.S. Pat. No. 5,405,772; PCT US94/09622. The serum-free base medium may, in another embodiment, contain clinical grade bovine serum albumin, which may be, in another embodiment, at a concentration of about 0.5-5%, or, in another embodiment, about 1.0% (w/v). Clinical grade albumin derived from human serum, such as Buminate® (Baxter Hyland, Glendale, Calif.), may be used, in another embodiment.

In another embodiment, the T cells of this invention may be separated via affinity-based separation methods. Techniques for affinity separation may include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques may also include the use of fluorescence activated cell sorters, which can have varying degrees of sophistication, such as multiple color channels, low angle and obtuse light scattering detecting channels, impedance channels, etc. It is to be understood that any technique, which enables separation of the NK T cells of this invention may be employed, and is to be considered as part of this invention.

In another embodiment, the affinity reagents employed in the separation methods may be specific receptors or ligands for the cell surface molecules indicated hereinabove.

In another embodiment, the antibodies utilized herein may be conjugated to a label, which may, in another embodiment, be used for separation. Labels may include, in other embodiments, magnetic beads, which allow for direct separation, biotin, which may be removed with avidin or streptavidin bound to, for example, a support, fluorochromes, which may be used with a fluorescence activated cell sorter, or the like, to allow for ease of separation, and others, as is well known in the art. Fluorochromes may include, in one embodiment, phycobiliproteins, such as, for example, phycoerythrin, allophycocyanins, fluorescein, Texas red, or combinations thereof.

In one embodiment, cell separations utilizing antibodies will entail the addition of an antibody to a suspension of cells, for a period of time sufficient to bind the available cell surface antigens. The incubation may be for a varied period of time, such as in one embodiment, for 5 minutes, or in another embodiment, 15 minutes, or in another embodiment, 30 minutes, or in another embodiment, 45 minutes, or in another embodiment, 60 minutes, or in another embodiment, 90 minutes. Any length of time which results in specific labeling with the antibody, with minimal non-specific binding is to be considered envisioned for this aspect of the invention.

Any length of time which results in specific labeling with the antibody, with minimal non-specific binding is to be considered envisioned for this aspect of the invention.

In another embodiment, the staining intensity of the cells can be monitored by flow cytometry, where lasers detect the quantitative levels of fluorochrome (which is proportional to the amount of cell surface antigen bound by the antibodies). Flow cytometry, or FACS, can also be used, in another embodiment, to separate cell populations based on the intensity of antibody staining, as well as other parameters such as cell size and light scatter.

In another embodiment, the labeled cells are separated based on their expression of CD161 and Vα24i TCR. The separated cells may be collected in any appropriate medium that maintains cell viability, and may, in another embodiment, comprise a cushion of serum at the bottom of the collection tube.

In another embodiment, the culture containing the T cells of this invention may contain other cytokines or growth factors to which the cells are responsive. In one embodiment, the cytokines or growth factors promote survival, growth, function, or a combination thereof of the NK T cells. Cytokines and growth factors may include, in other embodiments, polypeptides and non-polypeptide factors.

In one embodiment, the NK T cell populations of this invention are antigen specific.

In one embodiment, the term "antigen specific" refers to a property of the population such that supply of a particular antigen, or in another embodiment, a fragment of the antigen, results, in one embodiment, in specific cell proliferation, when presented the antigen, which in one embodiment, is in the context of CD1. In one embodiment, the antigen is any compound of this invention.

In another embodiment, supply of the antigen or fragment thereof, results in NK T cell production of interleukin 2, or in another embodiment, interferon-γ, or in another embodiment, interleukin-4, or in another embodiment, a combination thereof. In one embodiment, the NK T cell population expresses a monoclonal T cell receptor. In another embodiment, the NK T cell population expresses polyclonal T cell receptors.

In one embodiment, the T cells will be of one or more specificities, and may include, in another embodiment, those that recognize a mixture of antigens derived from an antigenic source. In one embodiment, a mixture of the compounds of this invention may be used to simulate a NK T cells of varying specificity.

In one embodiment, the NK T cell population suppresses an autoimmune response. In one embodiment, the term "autoimmune response" refers to an immune response directed against an auto- or self-antigen. In one embodiment, the autoimmune response is rheumatoid arthritis, multiple sclerosis, diabetes mellitus, myasthenia gravis, pernicious anemia, Addison's disease, lupus erythematosus, Reiter's syndrome, atopic dermatitis or Graves disease. In one embodiment, the autoimmune disease caused in the subject is a result of self-reactive T cells, which recognize multiple self-antigens.

In another embodiment, the NK T cell population suppresses an inflammatory response. In one embodiment, the term "inflammatory response" refers to any response that is, in one embodiment, caused by inflammation or, in another embodiment, whose symptoms include inflammation. By way of example, an inflammatory response may be a result of septic shock, or, in another embodiment, a function of rheumatoid arthritis. The inflammatory response may be a part of an overall inflammatory disorder in a subject, and may comprise, in another embodiment, cardiovascular disease, rheumatoid arthritis, multiple sclerosis, Crohn's disease, inflammatory bowel disease, systemic lupus erythematosus, polymyositis, septic shock, graft versus host disease, host versus graft disease, asthma, rhinitis, psoriasis, cachexia associated with cancer, or eczema. In one embodiment, as described hereinabove, the inflammation in the subject may be a result of T cells, which recognize multiple antigens in the subject. In one embodiment, the NK T cells of this invention may be specific for a single antigen where multiple antigens are recognized, yet the NK T cell population effectively suppresses inflammation in the subject. In one embodiment, suppression of inflammation is via modulating an immune response as a result of production of a particular cytokine profile. In one embodiment, the NK T cells produce cytokines which serve to downmodulate the inflammatory response.

In another embodiment, the NK T cell populations of this invention suppresses an allergic response. In one embodiment, the term "allergic response" refers to an immune system attack against a generally harmless, innocuous antigen or allergen. Allergies may in one embodiment include, but are not limited to, hay fever, asthma, atopic eczema as well as allergies to poison oak and ivy, house dust mites, bee pollen, nuts, shellfish, penicillin or other medications, or any other compound or compounds which induce an allergic response. In one embodiment, multiple allergens elicit an allergic response, and the antigen recognized by the NK T cells of this invention may be any antigen thereof. In one embodiment, suppression of allergic responses is via modulating an immune response as a result of production of a particular cytokine profile. In one embodiment, the NK T cells produce cytokines which serve to downmodulate the allergic response.

In another embodiment, the NK T cells of the present invention are utilized, in circumstances wherein eliciting a "Th1" response is beneficial in a subject, wherein the subject has a disease where a so-called "Th2" type response has developed. Introduction of the NK T cells, in one embodiment, results in a shift toward a Th1 type response, in response to the cytokine profile produced from the NK T cells.

In one embodiment, the term "Th2 type response" refers to a pattern of cytokine expression, elicited by T Helper cells as part of the adaptive immune response, which support the development of a robust antibody response. Typically Th2 type responses are beneficial in helminth infections in a subject, for example. Typically Th2 type responses are recognized by the production of interleukin-4 or interleukin 10, for example.

In one embodiment, the term "Th1 type response" refers to a pattern of cytokine expression, elicited by T Helper cells as part of the adaptive immune response, which support the development of robust cell-mediated immunity. Typically Th1 type responses are beneficial in intracellular infections in a subject, for example. Typically Th1 type responses are recognized by the production of interleukin-2 or interferon γ, for example.

In another embodiment, the reverse occurs, where a Th1 type response has developed, when Th2 type responses provide a more beneficial outcome to a subject, where introduction of the NK T cells, vaccines or compositions of the present invention provides a shift to the more beneficial cytokine profile. One example would be in leprosy, where the NK T cells, vaccines or compositions of the present invention stimulates a Th1 cytokine shift, resulting in tuberculoid leprosy, as opposed to lepromatous leprosy, a much more severe form of the disease, associated with Th2 type responses.

In another embodiment, the NK T cells of this invention, and obtained via the methods of this invention, may be a part of a vaccine or composition. Such vaccines and/or compositions may be used in any applicable method of this invention, and represents an embodiment thereof.

For example, in one embodiment, the methods of this invention for stimulating, inhibiting, suppressing or modulating an immune response in a subject, which comprise contacting an NKT cell in a subject with a compound of the invention, may also comprise contacting the NKT cell with a compound in a composition, or in another embodiment, contacting the NKT cell with a vaccine comprising at least one compound of the invention.

It is to be understood that any use of the NK T cells, vaccines or compositions of the present invention for methods of enhancing immunogenicity, such as, for example, for purposes of immunizing a subject to prevent disease, and/or ameliorate disease, and/or alter disease progression are to be considered as part of this invention.

Examples of infectious virus to which stimulation of a protective immune response is desirable, which may be accomplished via the methods of this invention, or utilizing the NK T cells, vaccines or compositions of the present invention include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g. African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria to which stimulation of a protective immune response is desirable, which may be accomplished via the methods of this invention, or utilizing the NK T cells, vaccines or compositions of the present invention include: *Helicobacter pylori, Borellia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Chlamidia* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Actinomyces israelli* and *Francisella tularensis.*

Examples of infectious fungi to which stimulation of a protective immune response is desirable, which may be accomplished via the methods of this invention, or utilizing the NK T cells, vaccines or compositions of the present invention include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* sp., *Leishmania* sp., *Schistosoma* sp. and *Toxoplasma* sp.

It is to be understood that the modulation of any immune response, via the use of the NK T cell populations, vaccines or compositions of this invention are to be considered as part of this invention, and an embodiment thereof.

In another embodiment, the NK T cell populations of this invention may be isolated, culture-expanded, or otherwise manipulated, as will be understood by one skilled in the art. In one embodiment, the NK T cells as derived by the methods of this invention, may be further engineered to express substances of interest. In one embodiment, the NK T cell populations may be engineered to express particular adhesion molecules, or other targeting molecules, which, when the cells are provided to a subject, facilitate targeting of the NK T cell populations to a site of interest. For example, when NK T cell activity is desired to modulate an immune response at a mucosal surface, the isolated NK T cell populations of this invention may be further engineered to express the $\alpha_e\beta_7$ adhesion molecule, which has been shown to play a role in mucosal homing. The cells can be engineered to express other targeting molecules, such as, for example, an antibody specific for a protein expressed at a particular site in a tissue, or, in another embodiment, expressed on a particular cell located at a site of interest, etc. Numerous methods are well known in the art for engineering the cells, and may comprise the use of a vector, or naked DNA, wherein a nucleic acid coding for the targeting molecule of interest is introduced via any number of methods well described.

A nucleic acid sequence of interest may be subcloned within a particular vector, depending upon the desired method of introduction of the sequence within cells. Once the nucleic acid segment is subcloned into a particular vector it thereby becomes a recombinant vector. Polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

There are a number of techniques known in the art for introducing the above described recombinant vectors into cells, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone, or any of the marker proteins listed herein.

In another embodiment, this invention provides a method for producing an isolated, culture-expanded NK T cell population, comprising contacting Vα14i, or Vα24i T cells with dendritic cells and a compound of this invention, for a period of time resulting in antigen-specific T cell expansion and isolating the expanded T cells thus obtained, thereby producing an isolated, culture-expanded NK T cell population.

In one embodiment, the method for producing an isolated culture-expanded NK T cell population, further comprises the step of adding a cytokine or growth factor to the dendritic cell, NK T cell culture. In one embodiment, NK T cells secretion of interleukin-2, interferon-γ or interleukin-4 is detected, at which time the NK T cells are used in the methods of this invention.

Dendritic cells stimulated NK T cell cytokine production, when presenting a compound of this invention, in the context of CD1. In another embodiment of this invention, the stimulated NK T cells may induce maturation of the dendritic cells, which may be mediated via TCR and CD1d/glycolipid interactions, and engagement of the CD40/CD40L interaction. This in turn, in another embodiment, may promote IL-12 secretion by the dendritic cells, and/or upregulation of, interalia, MHC molecules, DEC-205, or costimulatory molecules such as the B7 family. Dendritic cell maturation as a result of this interaction, may, in another embodiment, lead to enhanced adaptive immune responses, which in another embodiment, includes adjuvant activity of the compounds of this invention.

In one embodiment, the term "dendritic cell" (DC) refers to antigen-presenting cells, which are capable of presenting antigen to T cells, in the context of CD1. In one embodiment, the dendritic cells utilized in the methods of this invention may be of any of several DC subsets, which differentiate from, in one embodiment, lymphoid or, in another embodiment, myeloid bone marrow progenitors. In one embodiment, DC development may be stimulated via the use of granulocyte-macrophage colony-stimulating-factor (GM-CSF), or in another embodiment, interleukin (IL)-3, which may, in another embodiment, enhance DC survival.

In another embodiment, DCs may be generated from proliferating progenitors isolated from bone marrow. In another embodiment, DCs may be isolated from CD34+ progenitors as described by Caux and Banchereau in Nature in 1992, or from monocytes, as described by Romani et al, J. Exp. Med. 180: 83-93 '94 and Bender et al, J. Immunol. Methods, 196: 121-135, '96 1996. In another embodiment, the DCs are isolated from blood, as described for example, in O'Doherty et al, J. Exp. Med. 178: 1067-1078 1993 and Immunology 82: 487-493 1994, all methods of which are incorporated fully herewith by reference.

In one embodiment, the DCs utilized in the methods of this invention may express myeloid markers, such as, for example, CD11c or, in another embodiment, an IL-3 receptor-α (IL-3Rα) chain (CD123). In another embodiment, the DCs may produce type I interferons (IFNs). In one embodiment, the DCs utilized in the methods of this invention express costimulatory molecules. In another embodiment, the DCs utilized in the methods of this invention may express additional adhesion molecules, which may, in one embodiment, serve as additional costimulatory molecules, or in another embodiment, serve to target the DCs to particular sites in vivo, when delivered via the methods of this invention, as described further hereinbelow.

In one embodiment, the DCs may be obtained from in vivo sources, such as, for example, most solid tissues in the body, peripheral blood, lymph nodes, gut associated lymphoid tissue, spleen, thymus, skin, sites of immunologic lesions, e.g. synovial fluid, pancreas, cerebrospinal fluid, tumor samples, granulomatous tissue, or any other source where such cells may be obtained. In one embodiment, the dendritic cells are obtained from human sources, which may be, in another embodiment, from human fetal, neonatal, child, or adult sources. In another embodiment, the dendritic cells used in the methods of this invention may be obtained from animal sources, such as, for example, porcine or simian, or any other animal of interest. In another embodiment, dendritic cells used in the methods of this invention may be obtained from subjects that are normal, or in another embodiment, diseased, or in another embodiment, susceptible to a disease of interest.

Dendritic cell separation may accomplished in another embodiment, via any of the separation methods as described herein. In one embodiment, positive and/or negative affinity based selections are conducted. In one embodiment, positive selection is based on CD86 expression, and negative selection is based on GR1 expression.

In another embodiment, the dendritic cells used in the methods of this invention may be generated in vitro by culturing monocytes in presence of GM-CSF and IL-4.

In one embodiment, the dendritic cells used in the methods of this invention may express CD83, an endocytic receptor to increase uptake of the autoantigen such as DEC-205/CD205 in one embodiment, or DC-LAMP (CD208) cell surface markers, or, in another embodiment, varying levels of the antigen presenting MHC class I and II products, or in another embodiment, accessory (adhesion and co-stimulatory) molecules including CD40, CD54, CD58 or CD86, or any combination thereof. In another embodiment, the dendritic cells may express varying levels of CD115, CD14, CD68 or CD32.

In one embodiment, mature dendritic cells are used for the methods of this invention. In one embodiment, the term "mature dendritic cells" refers to a population of dendritic cells with diminished CD115, CD14, CD68 or CD32 expression, or in another embodiment, a population of cells with enhanced CD86 expression, or a combination thereof. In another embodiment, mature dendritic cells will exhibit increased expression of one or more of p55, CD83, CD40 or CD86 or a combination thereof. In another embodiment, the dendritic cells used in the methods of this invention will express the DEC-205 receptor on their surface. In another embodiment, maturation of the DCs may be accomplished via, for example, CD40 ligation, CpG oligodeoxyribonucleotide addition, ligation of the IL-1, TNFα or TOLL like receptor ligand, bacterial lipoglycan or polysaccharide addition or activation of an intracellular pathway such as TRAF-6 or NF-κB.

In one embodiment, inducing DC maturation may be in combination with endocytic receptor delivery of a preselected antigen. In one embodiment, endocytic receptor delivery of antigen may be via the use of the DEC-205 receptor.

In one embodiment, the maturation status of the dendritic may be confirmed, for example, by detecting either one or more of 1) an increase expression of one or more of p55, CD83, CD40 or CD86 antigens; 2) loss of CD115, CD14, CD32 or CD68 antigen; or 3) reversion to a macrophage phenotype characterized by increased adhesion and loss of veils following the removal of cytokines which promote maturation of PBMCs to the immature dendritic cells, by methods well known in the art, such as, for example, immunohistochemistry, FACS analysis, and others.

In one embodiment, the dendritic cells used for the methods of this invention may express, or in another embodiment, may be engineered to express a costimulatory molecule. In one embodiment, dendritic cells used for the methods of this invention are enriched for $CD86^{high}$ or $CD80^{high}$ expression.

In another embodiment, the dendritic cells used in the methods of this invention are selected for their capacity to expand antigen-specific NK T cells. In one embodiment, the DCs are isolated from progenitors or from blood for this purpose. In another embodiment, dendritic cells expressing high amounts of DEC-205/CD205 are used for this purpose.

NK T cell expansion, in one embodiment, is antigen-specific. In one embodiment, a compound of this invention is supplied in the culture simultaneously with dendritic cell contact with the NK T cells. In another embodiment, dendritic cells, which have already processed antigen are contacted with the NK T cells.

In one embodiment, the term "contacting a target cell" refers herein to both direct and indirect exposure of cell to the indicated item. In one embodiment, contact of NK T cells with a compound of this invention, a cytokine, growth factor, dendritic cell, or combination thereof, is direct or indirect. In one embodiment, contacting a cell may comprise direct injection of the cell through any means well known in the art, such as microinjection. It is also envisaged, in another embodiment, that supply to the cell is indirect, such as via provision in a culture medium that surrounds the cell, or administration to a subject, via any route well known in the art, and as described hereinbelow.

Methods for priming dendritic cells with antigen are well known to one skilled in the art, and may be effected, as described for example Hsu et al., Nature Med. 2:52-58 (1996); or Steinman et al. International application PCT/US93/03141.

In one embodiment, a compound of this invention is added to a culture of dendritic cells prior to contact of the dendritic cells with NK T cells. In one embodiment, a compound of this invention is used at a concentration of between about 0.1 to about 200 μg/ml. In one embodiment, 10-50 μg/ml is used. The dendritic cells are, in one embodiment, cultured in the presence of the antigen for a sufficient time to allow for uptake and presentation, prior to, or in another embodiment, concurrent with culture with NK T cells. In another embodiment, the compound is administered to the subject, and, in another embodiment, is targeted to the dendritic cell, wherein uptake occurs in vivo, for methods as described hereinbelow.

Antigenic uptake and processing, in one embodiment, can occur within 24 hours, or in another embodiment, longer periods of time may be necessary, such as, for example, up to and including 4 days or, in another embodiment, shorter periods of time may be necessary, such as, for example, about 1-2 hour periods.

In one embodiment, NK T cells may be cultured with dendritic cells with a dendritic cell to T cell ratio of 10:1 to 1:1 to 1:10, which ratio, in some embodiments is dependent upon the purity of the NKT cell population used. In one embodiment, about 20,000-100,000 cells/well (96-well flat bottom plate) of a NKT cell line, or 5 million per ml T cells, or in another embodiment, 200,000-400,000 cells/well of enriched NKT are administered to a subject, for some of the methods of this invention.

In one embodiment, about 5 million T cells are administered to a subject, for some of the methods of this invention.

In another embodiment, the NK T cells expanded by the dendritic cells in the methods of this invention are autologous, syngeneic or allogeneic, with respect to the dendritic cells.

In another embodiment, the dendritic cells used in the methods of this invention are isolated from a subject suffering from an autoimmune disease or disorder, cancer, an infection, which in one embodiment, is HIV, mycobacterial or malarial infection.

In another embodiment, the dendritic cells used in the methods of this invention are isolated from a subject with an inappropriate or undesirable immune response, or in another embodiment, the dendritic cells used in the methods of this invention are isolated from a subject with an allergic response.

In one embodiment, the NK T cells can be used to modulate an immune response, in a disease-specific manner. It is to be understood that any immune response, wherein it is desired to enhance cytokine production, or elicit a particular cytokine profile, including interferon-γ, interleukin-2 and/or interleukin-4, the NK T cells of this invention may be thus utilized, and represents an embodiment of this invention.

In another embodiment, the methods of this invention may further comprise the step of culturing previously isolated, NK T cells with additional dendritic cells, and a compound of this invention, for a period of time resulting in further NK T cell expansion, cytokine production, or a combination thereof.

In another embodiment, this invention provides a method for delaying onset, reducing incidence or suppressing a disease in a subject, comprising the steps of contacting in a culture NK T cells with dendritic cells and a compound of this invention, for a period of time resulting in NK T cell expansion, cytokine production or a combination thereof, and administering NK T cells thus obtained to the subject, wherein the NK T cells delay onset, reduce incidence or suppress a disease in the subject, thereby delaying onset, reducing incidence or suppressing a disease in the subject.

In one embodiment, cells for administration to a subject in this invention may be provided in a composition. These compositions may, in one embodiment, be administered parenterally or intravenously. The compositions for administration may be, in one embodiment, sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium. In another embodiment, the compositions may comprise adjuvants, which are well known to a person skilled in the art (for example, vitamin C, antioxidant agents, etc.) for some of the methods as described herein, wherein stimulation of an immune response is desired, as described further hereinbelow.

In one embodiment, the compounds, cells, vaccines or compositions of this invention may be administered to a subject via injection. In one embodiment, injection may be via any means known in the art, and may include, for example, intra-lymphoidal, or subcutaneous injection.

In another embodiment, the NK T cells and dendritic cells for administration in this invention may express adhesion molecules for targeting to particular sites. In one embodiment, NK T cells and/or dendritic cells may be engineered to express desired molecules, or, in another embodiment, may be stimulated to express the same. In one embodiment, the DC cells for administration in this invention may further express chemokine receptors, in addition to adhesion molecules, and in another embodiment, expression of the same may serve to attract the DC to secondary lymphoid organs for priming. In another embodiment, targeting of DCs to these sites may be accomplished via injecting the DCs directly to secondary lymphoid organs through intralymphatic or intranodal injection.

In one embodiment, the antigen is delivered to dendritic cells in vivo in the steady state, which, in another embodiment, leads to expansion of disease specific NK T cells. Antigen delivery in the steady state can be accomplished, in one embodiment, as described (Bonifaz, et al. (2002) Journal of Experimental Medicine 196: 1627-1638; Manavalan et al. (2003) Transpl Immunol. 11: 245-58).

In another embodiment, select types of dendritic cells in vivo function to prime the NK T cells.

In one embodiment, this invention provides a method for modulating an immune response, which is an inappropriate or undesirable response. In one embodiment, the immune response is marked by a cytokine profile which is deleterious to the host.

In one embodiment, the NK T cells of this invention may be administered to a recipient contemporaneously with treatment for a particular disease, such as, for example, contemporaneous with standard anti-cancer therapy, to serve as adjunct treatment for a given cancer. In another embodiment, the NK T cells of this invention may be administered prior to the administration of the other treatment.

In another embodiment, this invention provides a method for modulating an immune response, which is directed to infection with a pathogen, and the immune response is not protective to the subject.

In one embodiment, the pathogen may mimic the subject, and initiate an autoimmune response. In another embodiment, infection with the pathogen results in inflammation, which damages the host. In one embodiment, the response results in inflammatory bowel disease, or in another embodiment, gastritis, which may be a result, in another embodiment, of *H. pylori* infection.

In another embodiment, the immune response results in a cytokine profile, which is not beneficial to the host. In one embodiment, the cytokine profile exacerbates disease. In one embodiment, a Th2 response is initiated when a Th1 response is beneficial to the host, such as for example, in lepromatous leprosy. In another embodiment, a Th1 response is initiated, and persists in the subject, such as for example, responses to the egg antigen is schistosomiasis.

According to this aspect, and in one embodiment, administration of the NK T cells alters the immune response initiated in the subject, was not beneficial to the subject. In another embodiment, the method may further comprise the step of administering an agent to the subject, which if further associated with protection from the pathogen.

In one embodiment, the term "modulating" refers to initiation, augmentation, prolongation, inhibition, suppression or prevention of a particular immune response, as is desired in a particular situation. In one embodiment, modulating results in diminished cytokine expression, which provides for diminished immune responses, or their prevention. In another embodiment, modulation results in the production of specific cytokines which have a suppressive activity on immune responses, or, in another embodiment, inflammatory responses in particular. In another embodiment, modulating results in enhanced cytokine expression, which provides for enhanced immune responses, or their stimulation. In another embodiment, modulation results in the production of specific cytokines which have a stimulatory activity on immune responses, or, in another embodiment, responses to infection, or neoplasia, in particular.

In one embodiment, this invention provides a method for modulating an immune response in a subject, comprising the steps of contacting a dendritic cell population in vivo with compound of this invention, whereby the dendritic cell population contacts NK T cells in the subject, wherein NK T cell contact promotes cytokine production from the NK T cell population, thereby modulating an immune response in a subject.

In one embodiment, the term "modulating" refers to stimulating, enhancing or altering the immune response. In one embodiment, the term "enhancing an immune response" refers to any improvement in an immune response that has already been mounted by a mammal. In another embodiment, the term "stimulating an immune response" refers to the initiation of an immune response against an antigen of interest in a mammal in which an immune response against the antigen of interest has not already been initiated. It is to be understood that reference to modulation of the immune response may, in another embodiment, involve both the humoral and cell-mediated arms of the immune system, which is accompanied by the presence of Th2 and Th1 T helper cells, respectively, or in another embodiment, each arm individually. For further discussion of immune responses, see, e.g., Abbas et al. Cellular and Molecular Immunology, 3rd Ed., W. B. Saunders Co., Philadelphia, Pa. (1997).

Modulation of an immune response can be determined, in one embodiment, by measuring changes or enhancements in production of specific cytokines and/or chemokines for either or both arms of the immune system. In one embodiment, modulation of the immune response resulting in the stimulation or enhancement of the humoral immune response, may be reflected by an increase in IL-6, which can be determined by any number of means well known in the art, such as, for example, by ELISA or RIA. In another embodiment, modulation of the immune response resulting in the stimulation or enhancement of the cell-mediated immune response, may be reflected by an increase in IFN-$\gamma$ or IL-12, or both, which may be similarly determined.

In one embodiment, stimulating, enhancing or altering the immune response is associated with a change in cytokine profile. In another embodiment stimulating, enhancing or altering the immune response is associated with a change in cytokine expression. Such changes may be readily measured by any number of means well known in the art, including as described herein, ELISA, RIA, Western Blot analysis, Northern blot analysis, PCR analysis, RNase protection assays, and others.

In one embodiment, the infection is a latent infection.

In another embodiment, the immune response inhibits disease progression in the subject, or in another embodiment, the immune response inhibits or prevents neoplastic transformation in the subject.

In one embodiment, inhibition or prevention of neoplastic transformation according to the methods of this invention may be effected via the use of tumor specific antigens, in addition to the compounds of this invention. In one embodiment, a tumor specific antigen may be, for example, mutated proteins which are expressed as a result of a neoplastic, or preneoplastic events. In one embodiment, the antigen is a molecule associated with malignant tumor cells, such as, for example altered ras. Non-limiting examples of tumors for which tumor specific antigens have been identified include melanoma, B cell lymphoma, uterine or cervical cancer.

In one embodiment, a melanoma antigen such as the human melanoma specific antigen gp75 antigen may be used, or, in another embodiment, in cervical cancer, papilloma virus antigens may be used for the methods of this invention. Tumor specific idiotypic protein derived from B cell lymphomas, or in another embodiment, antigenic peptide or protein is derived from the Epstein-Bass virus, which causes lymphomas may be used, as well.

In another embodiment, the antigenic peptide or protein is derived from HER2/neu or chorio-embryonic antigen (CEA) for suppression/inhibition of cancers of the breast, ovary, pancreas, colon, prostate, and lung, which express these antigens. Similarly, mucin-type antigens such as MUC-1 can be used against various carcinomas; the MAGE, BAGE, and Mart-1 antigens can be used against melanomas. In one embodiment, the methods may be tailored to a specific cancer patient, such that the choice of antigenic peptide or protein is based on which antigen(s) are expressed in the patient's cancer cells, which may be predetermined by, in other embodiments, surgical biopsy or blood cell sample followed by immunohistochemistry.

In one embodiment, the subject being treated via a method of this invention has a precancerous precursor, and/or is at an elevated risk for cancer. Such elements are well known in the art, and may comprise inappropriate expression of a given surface marker or oncoprotein, the presence of hyperplastic cells, or the subject may have at least one family member afflicted with a given cancer, or have a lifestyle associated with enhanced risk for the incidence of cancer, such as, for example, exposure to radiation, certain viral infections, smoking tobacco products, and others, as will be appreciated by one skilled in the art.

It is to be understood that any disease, disorder or condition, whereby such disease, disorder or condition may be positively affected by the production of a given cytokine profile, or in another embodiment, is positively affected by the presence of NK T cells, and may be so positively affected via a method of this invention, is to be considered as part of this invention.

The following non-limiting examples may help to illustrate some embodiments of the invention.

EXAMPLES

Figure 5A:
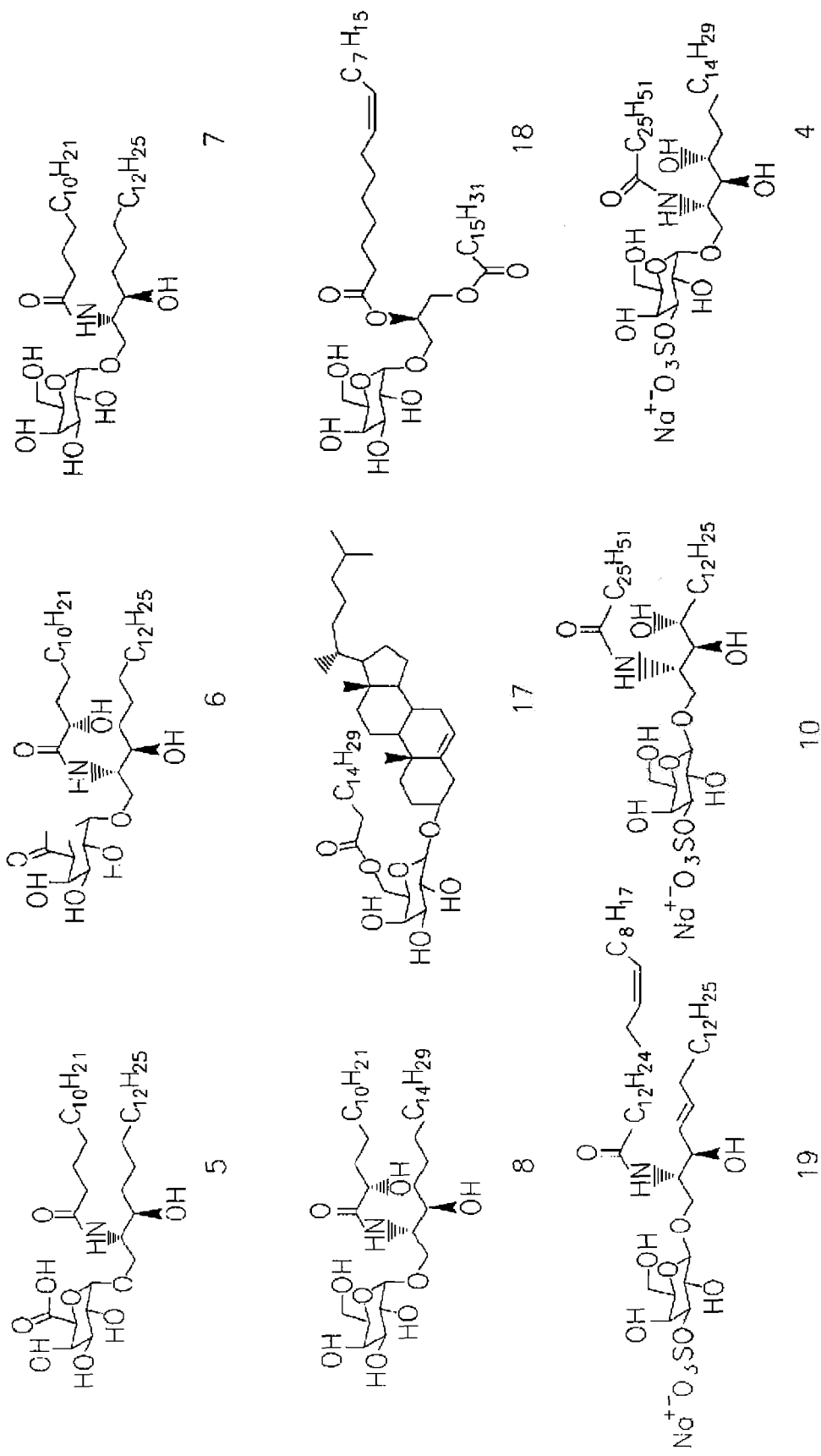
FIG. 5 depicts structures of glycolipids and analogues thereof, according to embodiments of the invention.
Figure 5B:
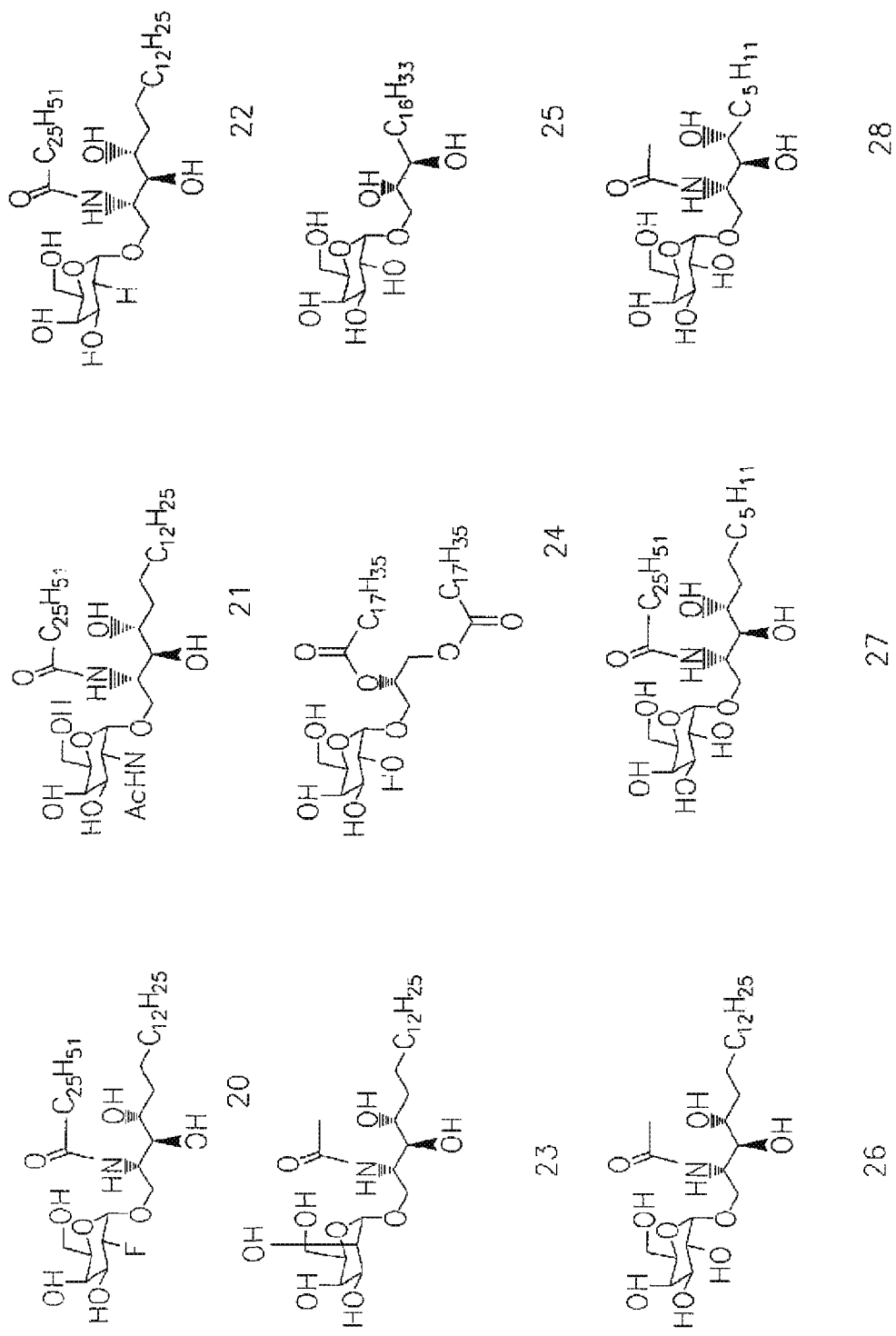
Figure 7A:
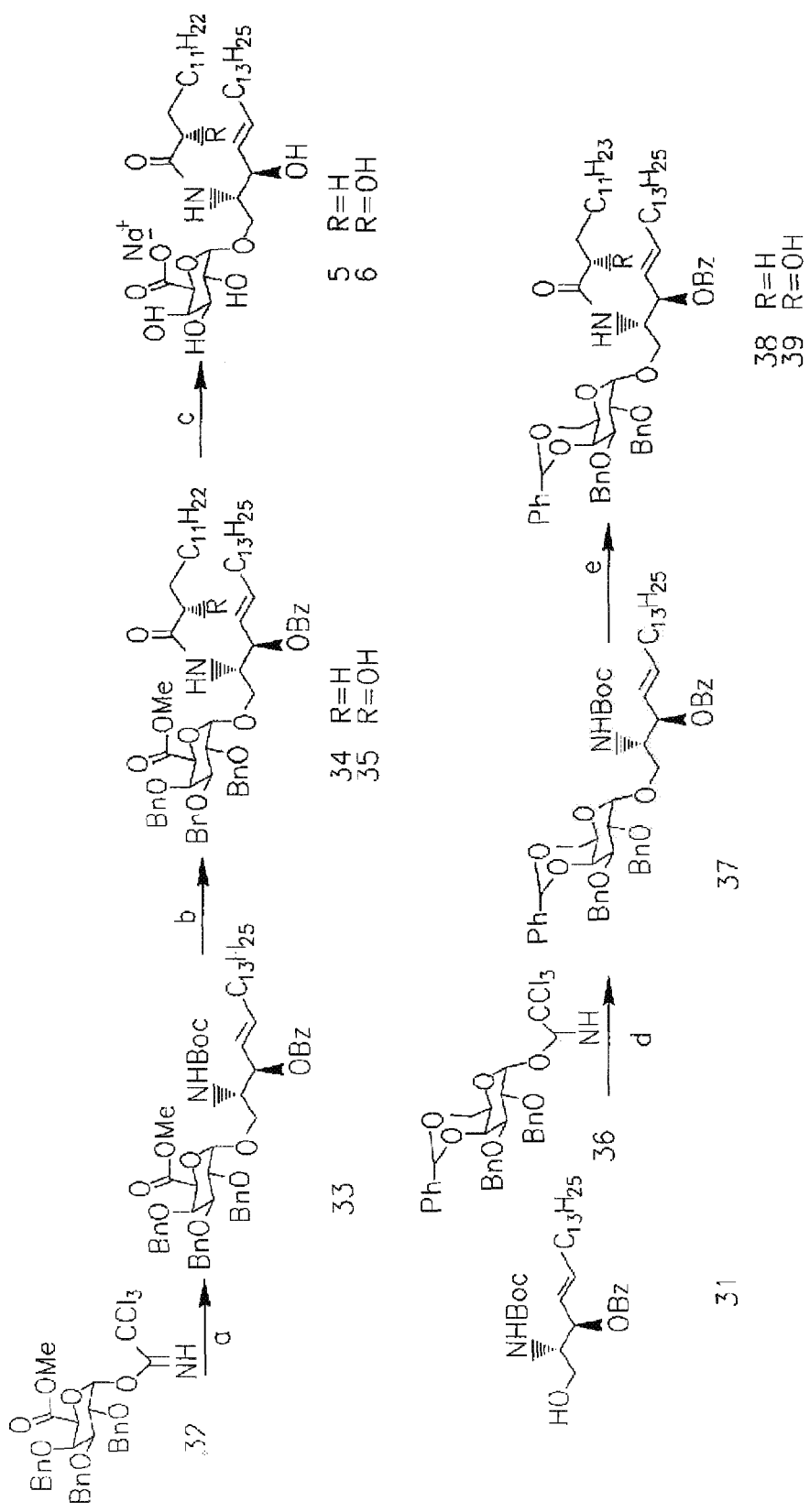
FIG. 7 schematically depicts the synthesis of some glycolipids, according to embodiments of the invention, as conducted herein. Reagents and conditions; a) 32, TMSOTf, 67%; b) (i) TFA, DCM, (ii) HBTU, myristic acid or 2-(S)-hydroxy myristic acid, n-Morpholine, ≈92% 2 steps; c) H$_2$, 20% Pd(OH)2, (ii) LiOH, H2O:THF:MeOH, 38%, 2 steps; d) 36, TMSOTf, 60%; e) (i) TFA, DCM, (ii) HBTU, myristic acid or 2-(S)-hydroxy myristic acid, n-Morpholine, ≈92% 2 steps; f) (i) NaOMe, MeOH, (ii) Pd/C, H$_2$, EtOH, 90% 2 steps; g) 40, TMSOTf, 62%. h) (i) TFA, DCM, (ii) HBTU, nervonic acid, n-Morpholine, 60% 2 steps; i) (i) NaOMe, MeOH, quant. (ii) Bu$_2$SnO, MeOH, (iii) Me$_3$N.SO$_3$, THF, 95%; j-k) (i) LDA, TMSOOTMS, (ii) H+, MeOH, 30%, 2 steps; then LiOH, H$_2$O:MeOH:THF, 81%; l) Novozyme 435, CH$_2$=CHOAc, 54% based on S isomer.
Figure 7B:
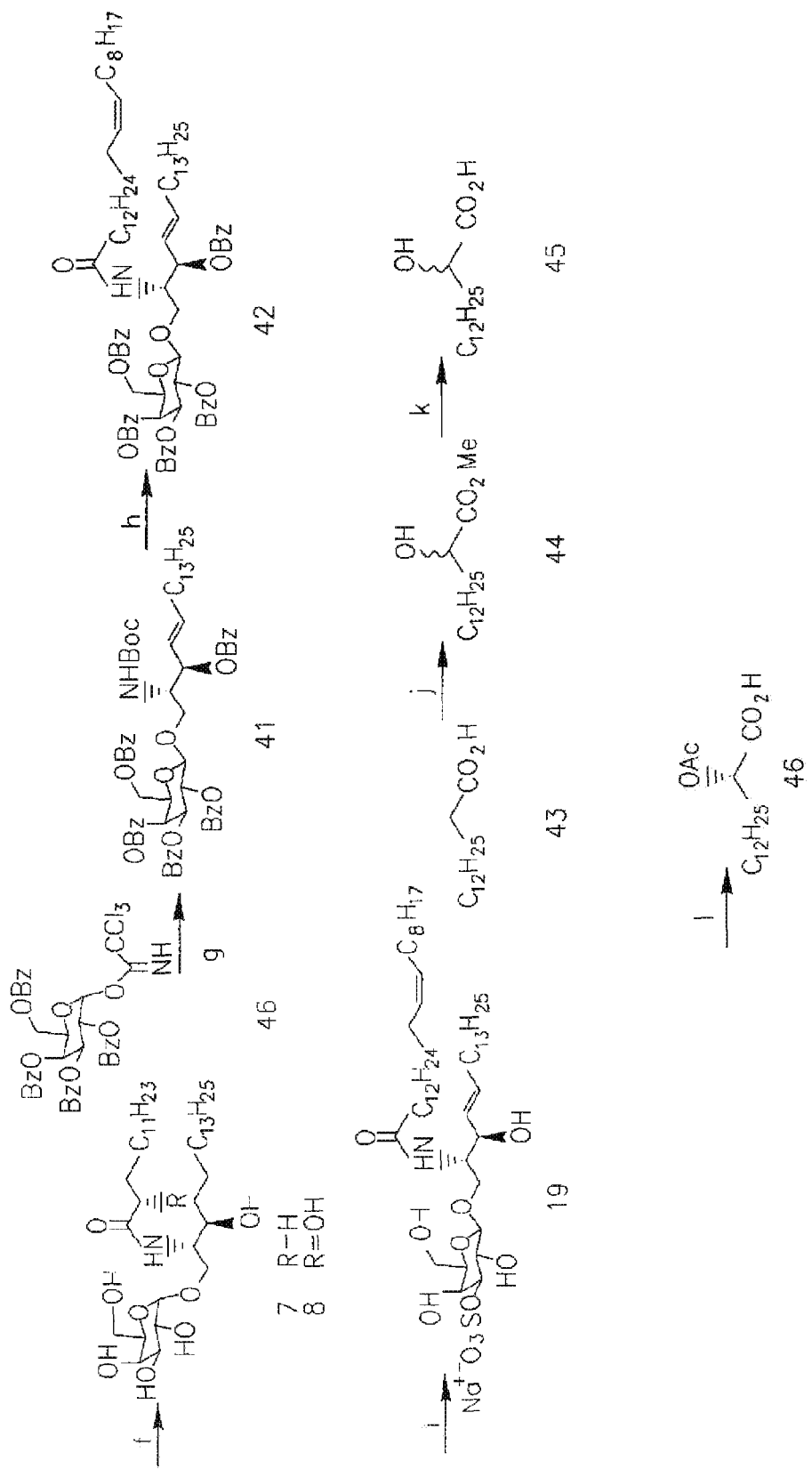

A number of glycolipids were synthesized (FIG. 5) and tested them for NKT cell activation. These included glycolipids of bacterial origin (compounds 5, 6, 17, and 18), α-GalCer analogues modified on the galactose moiety and acyl group, and variations of sulfatide, the only known promiscuous ligand for CD1. The bacterial glycolipids include those isolated from the outer membrane of *Sphingomonas wittichii* [Kawahara, K., Kubota, M., Sato, N., Tsuge, K. & Seto, Y. (2002) *FEMS Microbiol. Lett.* 214, 289-294] and glycolipids from *Borrelia burgdorferi*, the Lyme disease spirochete. CD1d-deficient (CD1d $^{-/-}$) mice were shown to have impaired host resistance to infection by *B. burgdorferi* making its glycolipids attractive compounds for further study as possible natural CD1d antigens [Kumar, H., Belperron, A., Barthold, S. W. & Bockenstedt, L. K. (2000) *J. Immunol.* 165, 4797-4801]. The structures of its two major glycolipids were recently elucidated as cholesteryl 6-O-acyl-β-D-galactopyranoside 5 (*B. burgdorferi* glycolipid 1, BbGL-I) and 1,2-di-O-acyl-3-O-α-D-galactopyranosyl-sn-glycerol 6 (BbGL-II). The *Sphingomonas* glycolipids, two new α-linked glycosphingolipids 5 and 6, (GSL-1 and GSL-2 respectively) differ most significantly from α-GalCer in the carbohydrate moiety as they contain galactosyluronic acids as the polar head group [Ben-Menachem, G., Kubler-Kielb, J., Coxon, B., Yergey, A. & Schneerson, R. (2003) *Proc. Natl. Acad. Sci. USA* 100, 7913-7918]. However, they are more physiologically relevant as natural ligands for CD1d-mediated NKT-cell activation since they originate from bacteria. Biological experiments further show that galactouronic sphingolipids stimulate IL-2 secretion in 1.2 (Vα14 Vβ8.2 DN3A4) NKT cell hybridomas. An α-GalCer analogue 4, 3-O-sulfo-galactosylceramide (3-O-sulfo-GalCer) also caused significant IL-2 secretion demonstrating that Vα14i NKT cell response is less sensitive to modification at the 3-OH position of galactose. By contrast, any modification made at the 2-OH position of galactose abolished all biological activity. Most other synthetic analogues, however, were active. In addition, reactivity of human Vα24i NKT cells to GSL-1 and GSL-2 and sulfatides were conserved.

Example 1

Synthesis of analogues of glycolipid α-galactosyl ceramide: 3-O-sulfo-α-galactosyl ceramide Preparation of Reagents Reagents All chemicals were purchased as reagent grade and used without further purification. Dichloromethane ($CH_2Cl_2$, DCM) was distilled over calcium hydride and tetrahydrofuran (THF) over sodium/benzophenone. Anhydrous methanol (MeOH) and pyridine (Py) were purchased from a commercial source.

General Assay Information:

Reactions were monitored with analytical thin-layer chromatography (TLC) on silica gel 60 $F_{254}$ glass plates and visualized under UV (254 nm) and/or by staining with acidic ceric ammonium molybdate. Flash column chromatography was performed on silica gel 60 Geduran (35-75 μm EM Science). $^1$H NMR spectra were recorded on a 400-500- or 600-Hz NMR spectrometer at 20° C. Chemical shift (in ppm) was determined relative to tetramethylsilane (δ 0 ppm) in deuterated solvents. Coupling constant(s) in hertz (Hz) were measured from one-dimensional spectra. $^{13}$C Attached Proton Test (C-Apt) spectra were obtained with the NMR-400, 500 or 600 spectrometer (100, 125 or 150 Hz) and were calibrated with either $CDCl_3$ (δ 77.23 ppm) or Py-$d_5$ (δ 123.87 ppm).

p-Methylphenyl 2-O-benzyl-4,6-O-benzylidene-3-O-levulinyl-1-thio-D-galactopyranoside (II)

3 grams of I (6.45 mmol) was dissolved in DCM. LevOH (0.9 ml, 1.35 eq), EDC (1.6 g, 1.3 eq) and DMAP (197 mg, 0.25 eq) were added. The reaction was allowed to proceed overnight while covered in foil. The reaction was then diluted with DCM, washed with water, saturated sodium bicarbonate solution, brine and dried over sodium sulfate. After removal of the solvent the mixture was purified by column chromatography (Hexanes:EtOAc:DCM 3:1:1) to give 2.83 g of II in 78% yield.

$^1$H (CDCl$_3$ 500 MHz) δ=7.61-7.03 (m, 14H), 5.48 (s, 1H), 4.98 (dd, J=3.7 Hz, J=9.6 Hz, 1H), 4.77 (d, J=11.0 Hz, 1H), 4.63 (d, J=9.5 Hz, 1H), 4.51 (d, J=11 Hz, 1H), 4.36-4.32 (m, 2H), 3.99-3.97 (m, 1H), 3.90-3.86 (m, 1H), 3.51 (s, 1H), 2.56-2.50 (m, 2H), 2.46-2.40 (m, 2H), 2.31 (s, 3H), 2.09, (s, 3H); $^{13}$C NMR (125 MHz, CDCl$_3$) δ=206.05, 172.09, 138.18, 137.76, 137.64, 133.11, 129.61, 128.98, 128.57, 128.22, 128.01, 127.68, 127.57, 126.45, 100.83, 86.53, 75.41, 75.05, 73.77, 73.71, 69.09, 37.70, 29.60, 27.99; HRMS (MALDI-FTMS) calcd. for C$_{32}$H$_{34}$O$_7$SNa [M+Na]$^+$ 585.1923, found 585.1900.

2-O-benzyl-4,6-O-benzylidene-3-O-levulinyl-D-galactopyranoside (III)

II (600 mg, 1.07 mmol) was dissolved in 50 mL of acetone. The reaction mixture was cooled to 0° C., and NBS (228 mg, 1.28 mmol, 1.2 equiv) was added. The reaction mixture turned orange immediately. After 10 min the reaction was quenched by addition of solid NH$_4$Cl. The mixture was diluted with water and ethyl acetate, and the aqueous layer was extracted with ethyl acetate (3×). The combined organic layer was extracted with brine, dried over sodium sulfate, and evaporated. The residue was subjected to column chromatography (hexanes:ethyl EtOAc:DCM 1:1:1) to give 442 mg (91%) of 7.

$^1$H (CDCl$_3$ 500 MHz) δ=7.50-7.25 (m, 10H), 5.48 (d, J=4.8, 1H), 5.38 (s, 1H), 5.32 (dd, J=3.7 Hz, J=10.3 Hz, 1H), 4.94-4.90 (m, 1H), 4.73-4.62 (m, 3H), 4.36 (d, J=3.3 Hz, 1H), 4.05 (dd, J=3.3 Hz, 10.3 Hz, 1H), 4.00-3.98 (m, 2H), 3.93, (s, 1H), 3.52-3.51 (m, 1H), 2.71-2.53 (m, 4H), 2.08 (s, 3H); $^{13}$C NMR (125 MHz, CDCl$_3$) δ=206.43, 177.73, 172.35, 172.24, 138.41, 137.78, 137.63, 137.57, 128.89, 128.85, 128.38, 128.21, 128.03, 127.75, 127.67, 127.51, 126.15, 126.12, 100.61, 97.50, 91.98, 77.57, 74.68, 74.10, 73.82, 73.56, 73.38, 73.28, 70.55, 69.17, 68.93, 66.24, 62.18, 37.82, 37.79, 29.67, 289.38, 28.11, 28.04; HRMS (MALDI-FTMS) calcd. for C$_{25}$H$_{29}$O$_8$ [M+H]$^+$ 457.1862 found 457.1856.

O-(2-O-benzyl-4,6-O-benzylidene-3-O-levulinyl-D-galactopyranosyl)Trichloroacetimidate (IV)

To a solution of III (188.5 mg, 0.46 mmol) dissolved in 4 ml of DCM was added CCl$_3$CN (0.46 ml, 4.62 mmol) and DBU (31 μl, 0.21 mmol). After 2 hours at room temperature, the dark solution was concentrated and then purified by flash chromatography Hexanes:EtOAc (2:1) and 1% triethylamine to yield 8 (211 mg, 77%).

$^1$H (CDCl$_3$ 500 MHz) δ=7.59-7.34 (m, 10H), 5.61 (s, 1H), 5.45 (dd, J=3.2 Hz, 10.7 Hz, 1H), 4.80-4.72 (m, 2H), 4.60 (d, J=3.3 Hz, 2H), 4.38-4.33 (m, 2H), 4.13-4.10 (dd, J=1.8 Hz, 12.5 Hz, 1H), 4.05 (s, 1H), 2.79-2.72 (m, 2H), 2.65 (m, 2H), 2.16 (s, 3H); $^{13}$C NMR (125 MHz, CDCl$_3$) δ=206.43, 177.73, 172.35, 172.27, 138.41, 137.78, 137.63, 137.57, 128.89, 128.85, 128.38, 128.21, 128.03, 127.86, 127.75, 127.67, 127.51, 126.15, 126.12, 100.61, 97.50, 91.98, 77.57, 74.68, 74.10, 73.56, 73.38, 73.28, 70.55, 69.17, 68.93, 66.24, 6218, 37.82 37.79, 29.67, 29.38, 28.11, 28.04.

2-Azido-3,4-di-O-benzyl-1-O-(2-O-benzyl-4,6-O-benzylidene-3-O-levulinyl-α-D-galactopyranosyl)-D-ribo-octadeca-6-ene-1-ol (VI)

A solution of trichloroacetimidate IV (150 mg, 0.25 mmol, 1.5 equiv)) and sphingosine derivative V (86 mg, 0.16 mmol) in 2.5 mL of anhydrous THF was added over freshly dried powdered AW-300 molecular sieves and cooled to −20° C. TMSOTf (23 μL, 0.8 equiv) was slowly added to the solution, and the mixture was warmed up to 0° C. in 2.5 hours. The reaction was quenched by addition of Et$_3$N (0.1 mL), and the mixture was diluted with EtOAc and filtered through Celite. The organic layer was washed with saturated aqueous NaHCO$_3$ and brine, dried (Na$_2$SO$_4$), and concentrated. The residue was purified by column chromatography on silica gel (hexanes:EtOAc 6:1) to furnish VI (57 mg, 46% based on consumed acceptor V) as a syrup, and recover V (18 mg).

$^1$H NMR (CDCl$_3$, 400 MHz): δ=7.49-7.23 (m 20H), 5.56-5.45 (m 3H), 5.32 (dd, 1H, J=3.5 Hz, 10.5 Hz), 4.98 (d, 1H, J=3.1 Hz), 4.70-4.51 (m, 6H), 4.38 (m, 1H), 4.13-3.82 (m, 5H), 3.71-3.62 (m, 4H), 2.75-2.40 (m, 6H), 2.08 (s, 3H), 2.06-1.97 (m, 2H), 1.25 (bs, 18H), 0.88 (t, 3H, J=7.0 Hz); $^{13}$C NMR (125 MHz, CDCl$_3$) δ=206.30, 172.25, 138.21, 137.93, 137.67, 132.60, 128.89, 128.37, 128.35, 128.33, 129.29, 128.08, 127.27, 128.08, 127.78, 127.73, 127.69, 127.63, 127.60, 127.17, 124.69, 100.65, 98.61, 79.41, 78.95, 74.06, 73.65, 73.41, 73.10, 71.94, 70.79, 69.02, 68.21, 62.41, 61.97, 37.93, 31.89, 29.71-29.32, 28.19, 27.58, 22.66, 14.10; ESI-MS (positive-ion mode): m/z 982.4 [M+Na]$^+$.

3,4-Di-O-benzyl-1-O-(2-O-benzyl-4,6-O-benzylidene-α-D-galactopyranosyl)-2-hexacosylamino-D-ribo-octadeca-6-ene-1-ol (X)

The azide VI (57 mg, 0.059 mmol) was dissolved in 2.0 mL of anhydrous THF and cooled to 0° C. PMe$_3$ (0.4 mL of 1.0 M in toluene, 0.4 mmol) was added to the solution, and the reaction was warmed up to room temperature and stirred over night. After almost disappearance of the starting material, 0.8 mL of aq 1 M NaOH was added to the mixture and stirred for 5 hours. CH$_2$Cl$_2$ was then added to the solution, and the mixture was washed with brine, dried over Na$_2$SO$_4$, and concentrated. The residue was used for the next step without further purification. Hexacosanoic acid (35 mg, 0.088 mmol, 1.5 eq) was suspended in CH$_2$Cl$_2$ (2.0 ml), and then DEPBT (26 mg 0.087 mmol, 1.5 eq) and DIEA (15 μL, 1.5 eq) were added. The mixture was vigorously shaken for 1 h to give a clear light yellow solution in which above crude amine mixture VIIIa and VIIIb was added subsequently. The solution was stirred over night at room temperature and then diluted with EtOAc and washed with saturated NaHCO$_3$ and brine. The organic phase was dried over Na$_2$SO$_4$ and concentrated to afford a solid (IXa and IXb, 57 mg), which was dissolved in 2 mL Py-HOAc solution (3:1 v/v, contains 0.30M NH$_2$NH$_2$.HOAc) and stirred for 1.5 h at room temperature. After the usual workup similarly as above, the residue was purified by column chromatography on silica gel (hexanes:EtOAc 2:1) to furnish X (40 mg, 56% over 3 steps) as a solid.

$^1$H NMR (CDCl$_3$, 400 MHz) δ=7.47-7.23 (m 20H), 5.67 (d, 1H, J=8.6 Hz), 5.51-5.44 (m, 3H), 4.95 (d, 1H, J=2.7 Hz), 4.77-4.49 (m, 6H), 4.40 (m, 1H), 4.21 (d, 1H, J=2.7 Hz), 4.12-4.07 (m, 2H), 3.94-3.58 (m, 8H), 2.45 (m, 2H), 2.08-1.88 (m, 4H), 1.49 (m, 2H), 1.25 (bs, 62H), 0.88 (t, 6H, J=7.0

Hz); $^{13}$C NMR (CDCl$_3$, 100 MHz): δ=173.14, 138.50, 138.33, 137.74, 132.57, 129.32, 128.62, 128.40, 128.08, 127.95, 127.85, 126.45, 125.20, 101.37, 99.04, 79.97, 79.22, 76.29, 73.48, 73.41, 71.79, 69.50, 68.86, 68.19, 62.94, 50.26, 36.96, 32.13, 29.91-29.56, 28.14, 27.78, 25.93, 22.90, 14.34; HRMS (MALDI-FTMS) calcd for C$_{78}$H$_{119}$NO$_9$Na [M+Na]$^+$ 1236.8777, found 1236.8741.

3,4-Di-O-benzyl-1-O-(2-O-benzyl-4,6-O-benzylidene-3-O-sulfo-α-D-galactopyranosyl)-2-hexacosylamino-D-ribo-octadeca-6-ene-1-ol, sodium salt (XI)

To a solution of X (40 mg, 0.033 mmol) in Py (2.5 mL) was added SO$_3$.Py complex (79 mg, 0.5 mmol, 15 eq). The mixture was stirred at room temperature for 2.5 hours. Water solution (2.5 mL) of NaHCO$_3$ (62 mg) was added to quench the reaction. The reaction mixture was diluted with CH$_2$Cl$_2$, and washed with brine, dried (Na$_2$SO$_4$), and concentrated. The residue was purified by column chromatography on silica gel (CH$_2$Cl$_2$:MeOH 15:1) to give XI (39 mg, 90%) as a solid.
$^1$H NMR (CDCl$_3$/CD$_3$OD 1:1, 400 MHz) δ=7.87 (d, 1H, J=8.9 Hz), 7.58-7.17 (m, 20H), 5.59 (s, 1H), 5.43 (m, 2H), 4.96 (m, 3H), 4.82 (m, 1H), 4.73 (d, 1H, J=2.3 Hz), 4.62-4.58 (m, 2H), 4.52-4.44 (m, 2H), 4.19-3.99 (m, 5H), 3.78 (bs, 2H), 3.66 (bs, 1H), 3.56 (m, 1H), 2.47 (m, 1H), 2.34 (m, 1H), 2.13 (t, 2H, J=7.0 Hz), 2.01 (m, 2H), 1.54 (bs, 2H), 1.27 (bs, 62H), 0.89 (t, 6H, J=7.0 Hz); $^{13}$C NMR (CDCl$_3$/CD$_3$OD 1:1, 100 MHz): δ=173.92, 138.30, 137.66, 137.57, 131.42, 128.43, 128.01-127.03, 125.95, 125.66, 100.59, 98.99, 80.16, 79.75, 75.04, 74.84, 73.97, 73.60, 73.49, 71.09, 68.74, 67.00, 62.70, 49.71, 49.62, 31.56, 29.29-29.02, 27.01, 25.59, 22.27, 13.44; HRMS (MALDI-FTMS) calcd for C$_{78}$H$_{118}$NO$_{12}$SNaK [M+K]$^+$ 1354.7909, found 1354.7933.

2-Hexacosylamino-1-O-(3-O-sulfo-α-D-galactopyranosyl)-D-ribo-1,3,4-octadecantriol, sodium salt (4)

XI (39 mg, 0.030 mmol) was dissolved in HOAc-MeOH (1:1 v/v, 6 mL). 80 mg of palladium black was added and the reaction solution was saturated with hydrogen by a balloon. After stirring at room temperature for 20 hours, the catalyst was removed by filtration over Celite and washed with CH$_2$Cl$_2$/MeOH (1:1) thoroughly. Evaporation of the solvent gave a residue which was dissolved in CH$_2$Cl$_2$/MeOH (1:1) mixed solvent again and then saturated NaHCO$_3$ (3 mL) was added to stir at room temperature for half an hour. After removal of the solvent, the residue was purified by column chromatography on silica gel (CH$_2$Cl$_2$:MeOH 6:1) to give 4 (24 mg, 83%) as a light yellow solid.
$^1$H NMR (CDCl$_3$/CD$_3$OD 1:1, 400 MHz) δ=4.95 (d, 1H, J=3.5 Hz), 4.49 (dd, 1H, J=2.7 Hz, 10.2 Hz), 4.35 (m, 1H), 4.17 (m, 1H), 4.02 (dd, 1H, J=2.7 Hz, 9.8 Hz), 3.88-3.85 (m, 2H), 3.80-3.72 (m, 4H), 3.69-3.65 (m, 2H), 3.61-3.57 (m, 1H), 2.24 (t, 2H, J=7.4 Hz), 1.59 (m, 4H), 1.27 (bs, 68H), 0.89 (t, 6H, J=7.0 Hz); $^{13}$C NMR (CDCl$_3$/CD$_3$OD 1:1, 100 MHz): δ=174.31, 99.08, 77.57, 73.42, 71.64, 70.44, 67.81, 67.19, 66.48, 61.28, 49.90, 35.89, 31.51, 31.32, 29.29-28.94, 25.53, 22.22, 13.34; HRMS (MALDI-FTMS) calcd for C$_{50}$H$_{98}$NO$_{12}$SNa$_2$ [M+Na]$^+$ 982.6599, found 982.6585.

Synthesis Scheme

Sulfatide and α-galactosyl ceramide have similar structures and possess immunostimulatory and immunomodulatory activity, when presented to T cells via CD1. In order to determine whether hybrid molecules of sulfatide and α-galactosyl ceramide, which are sulfate derivatives 3-O-sulfo-α/β-galactosylceramides 10 and 4 (FIG. 1), have comparable activity, the molecules were synthesized and evaluated for immunostimulatory activity.

For the synthesis of 3-O-sulfo-a-galactosylceramides 4, selective sulfation at 3" OH of the galactose moiety is a key step. Typically, regioselective sulfation of the 3-hydroxyl of the sugar ring utilizes dibutylstannylene acetals as activated intermediates, however, this method can only be applied to β-galactosides; for α-galactosides, the dibutylstannylene acetal can form a complex between the 2-hydroxyl and the anomeric oxygen to give the 2"-O-derivative by reaction with an electrophile.

In order to address this, a 3"-lev and 2"-benzyl-4",6"-benzylidene protected trichloroacetimidate donor IV (FIG. 2). The temporary protecting group Lev, can be selectively removed after glycosylation in the presence of hydrazine. The benzyl and benzylidene groups at 2,4,6 positions direct the next α-glycosidic bond formation (Figueroa-Perez, S. et al Carbohydrate Res. 2000, 328, 95; Plettenburg, O. et al. J. Org. Chem. 2002, 67, 4559).

Figures 2A, 2B:
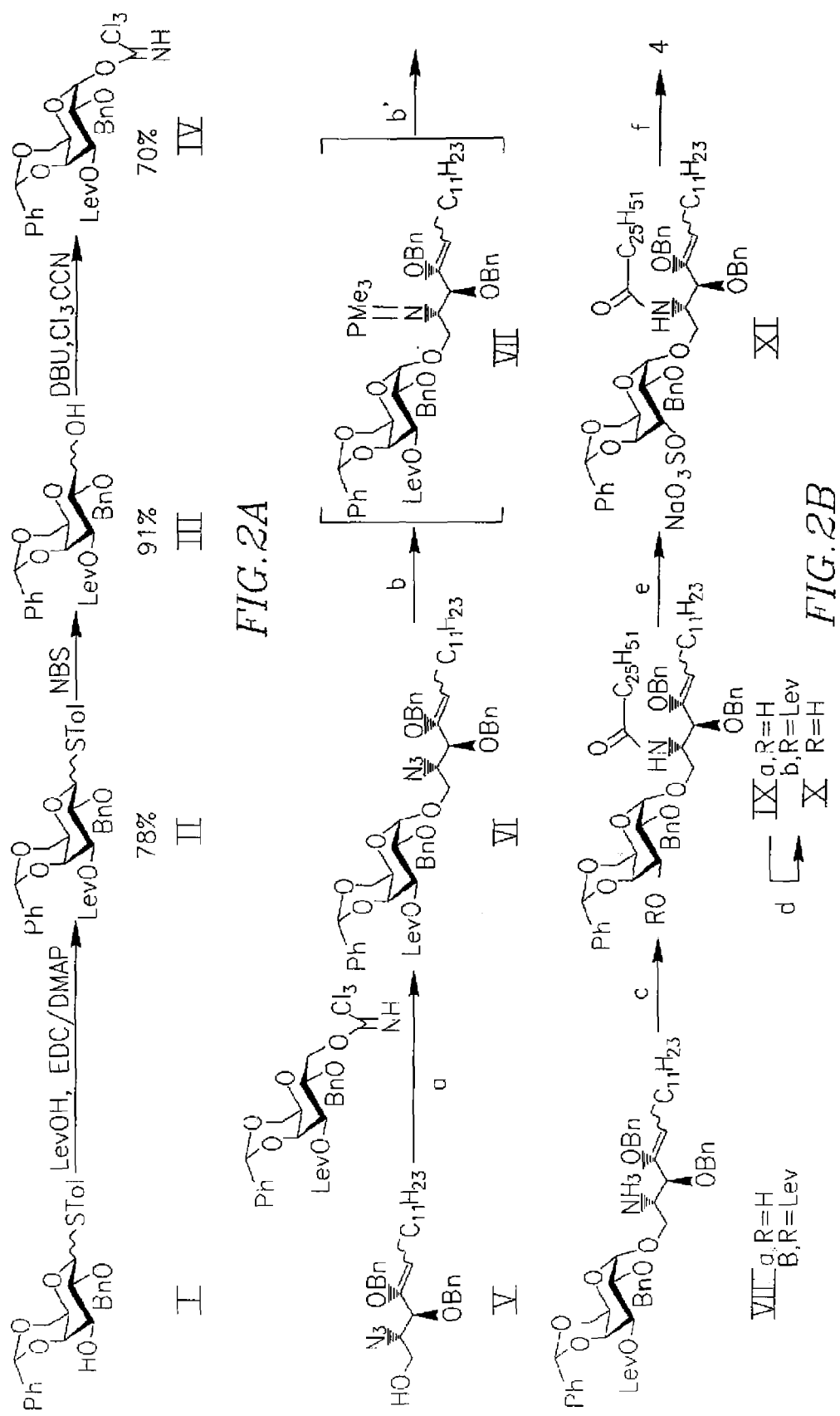
FIG. 2 demonstrates the preparation of (a) compound IV, according to embodiments of the invention; (b) the preparation of compound 4, according to embodiments of the invention.

As shown in FIG. 2A, the preparation of IV started with the known thioglycoside I in 50% yield over three steps. The sphingosine building block V was employed in this synthesis, with donor IV coupled to acceptor V in the presence of TMSOTf, used as promoter to give α-glycoside VI, in a moderate yield.

A staudinger reduction of VI with PMe$_3$, in NaOH solution was used to hydrolyze the imino-phosphorane intermediate VII, however, the Lev group cannot survive under this conditions and approximate 50% of the Lev group was cleaved to give an amine mixture of VIIIa and VIIIb (1:1) determined by $^1$H NMR. Since VIIIa possesses a free C-3 hydroxyl, it is crucial to choose a selective coupling reagent in the condensation between amine VIIIa and the fatty acid.

Since DEPBT [3-(diethoxyphosphoryloxy)-(1,2,3)-benzotriazin-4(3H)-one] can selectively form an amide bond in the presence of unprotected hydroxyl groups, it was used in the reaction mixture with VIIIa, VIIIb, and hexacosanoic acid to give IXa and IXb, followed by deprotection of the remaining Lev groups using hydrazine to provide the desired galactosyl ceramide X in 56% yield over 3 steps. Treating the 3"-OH free glycolipid X with Py.SO3 led to the sulfate derivative XI in high yield, which gave compound 4 upon hydrogenation with palladium black and neutralization with NaHCO$_3$ (aqueous solution) in 78% yield (FIG. 2B).

Example 2

Synthesis of analogues of glycolipid α-galactosyl ceramide

3-O-sulfo-β-galactosylceramide

Figure 3:
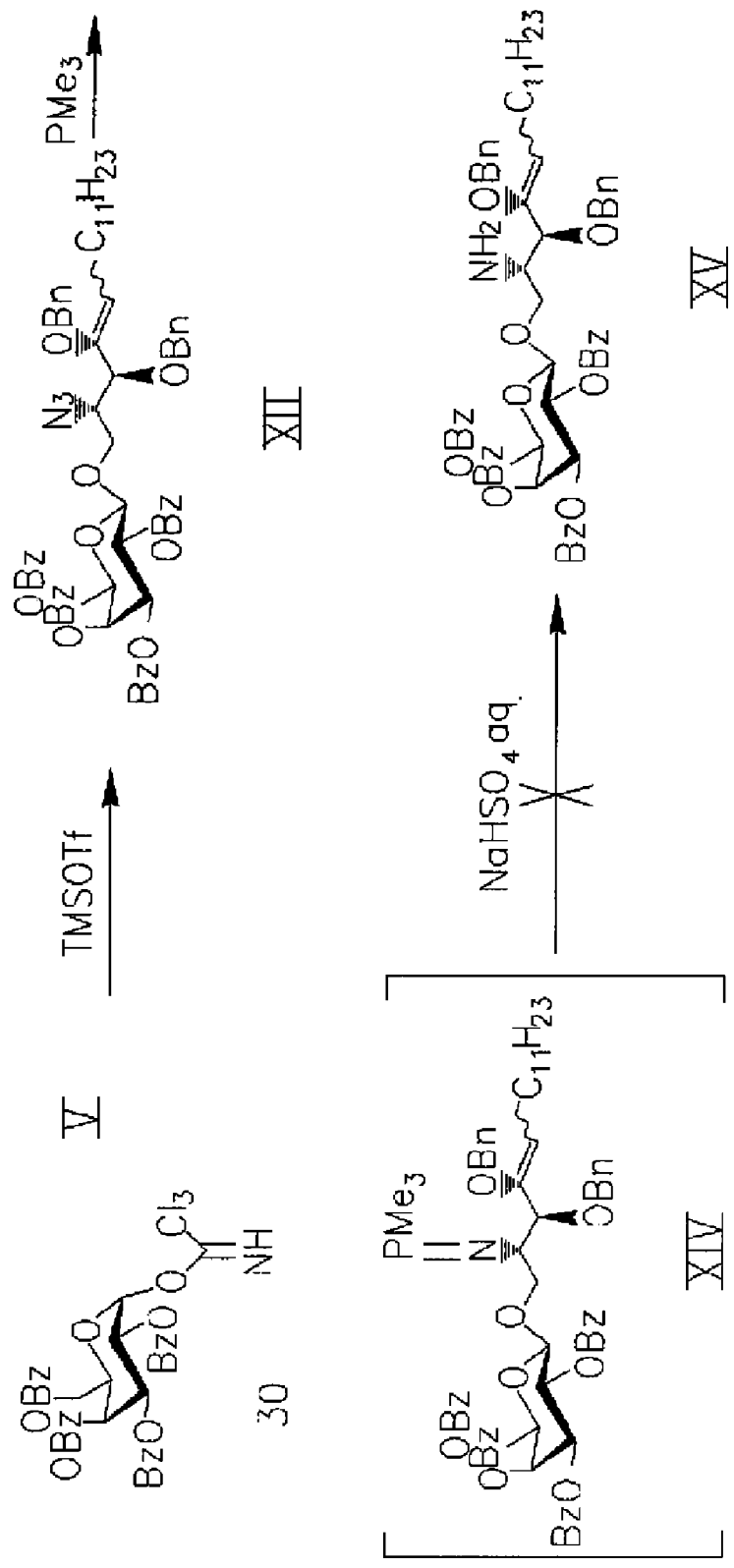
FIG. 3 demonstrates the preparation of compound XV, according to embodiments of the invention.

For the synthesis of 10, perbenzoylated trichloroacetimidate donor 40 is used in the glycosylation of the sphingosine acceptor V to yield a β-galactosyl ceramide derivative XII (FIG. 3). After the Staudinger reduction of XII, a complex mixture was produced, with no isolation of the amine XV. Since the perbenzoylated galactosyl ceramide is sensitive to basic conditions, a NaHSO$_4$ solution instead of a NaOH solution was used for the reduction work-up procedure to decompose the imino-phosphorane intermediate XIV. However, hydrolyzation of XIV into XV was very slow, and in turn, the longer reaction time led to the degradation of glycosidic bond which attributed to complicated product formation.

Example 3

Synthesis of analogues of glycolipid α-galactosyl ceramide

3-O-sulfo-β-galactosylceramide

Another synthetic strategy was used to synthesize 3-O-sulfo-β-galactosylceramide. In this strategy, the azide was first reduced, and the fatty acid coupled, prior to the glycosylation step (FIG. 4A). Compound XVIII was prepared from the sphingosine derivative XVI (Plettenburg, O. et al. J. Org. Chem. 2002, 67, 4559) in 54% yield over 2 steps.

Using TMSOTf as a promoter, the ceramide acceptor XVIII was reacted with donor 40 to give the β-glycoside XIX in 54% yield. After debenzyolation and hydrogenation of XIX, the β-galactosyl ceramide XX was obtained in quantitative yield. XX was finally sulfated by $Bu_2SnO/Me_3N.SO_3$ and subsequently neutralized by $NaHCO_3$ to give the product 10, in 80% yield (FIG. 4B) (Compostella, F et al. Tetrahedron 2002, 58, 8703).

Example 4

Recognition of Glycolipids by the Human NKT Cell Line Results in Cytokine Secretion Materials and Methods Glycolipids α-GalCer was obtained as described [Plettenburg, O., et al. (2002) J. Org. Chem. 67, 4559-64]. The intermediates 29, 36 and 40 (FIGS. 3 and 4), were obtained as described [Plettenburg, O., et al. (2002) supra; Williams, L., et al. (1996) Tetrahedron 52, 11673-11694; Deng, S.Y., B et al. (1999) J. Org. Chem. 64, 7265-7266]. The compounds 5, 6, 19, 30, 33, 37, and 41 (FIGS. 3 and 4) were obtained as described hereinbelow. The remaining compounds, except 19, 10 and 4, and their intermediates were obtained as described hereinabove.

Sphingosine Acceptor

The synthesis scheme for the sphingosine acceptor (30) is shown in FIG. 6. Compound 29 (3.31 g, 13.5 mmol) (Williams, L., et al. supra) was dissolved in 70 ml of dry THF. The solution was cooled to −40° C. and vinyl grignard solution (31 ml of a 1 M solution in THF) was added via a dropping funnel over a period of 1 hr. The temperature was kept between −20° C. and −40° C. The reaction mixture was allowed to warm to room temperature and stirred for another hr. The reaction was quenched by addition of 60 ml of saturated $(NH_4)_2SO_4$ solution and evaporated to dryness. The residue was diluted with water and extracted with ethyl acetate (3×). The combined organic layer was extracted with brine, dried over $MgSO_4$ and evaporated to give a yellow oil. Column chromatography (Hex:EtOAc 3:1) yielded the syn diastereomer (2.11 g, 8.2 mmol, anti/syn=3.5:1) in 61% yield. Then the syn diastereomer (300 mg, 1.16 mmol) was dissolved in 1 ml of dry dichloromethane in a two-necked flask equipped with a reflux condenser under argon. 486 mg (3.48 mmol) of pentadecene was added via a syringe. A solution of 20 mg (2 mol %) of Grubb's second generation catalyst (purchased from Strem Chemicals) in 1 ml of dichloromethane was added and the solution was heated under rapid reflux for 40 hr. The reaction mixture was evaporated and then directly chormatographed (Hex:EtOAc 6:1) which yielded (0.82 mmol, 71%) of the desired product.

Synthesis of Glycolipids

The synthesis scheme is shown in FIG. 4. A solution of trichloroacetimidate 32 (160.4 mg, 0.258 mmol) and sphingosine acceptor 31 (100 mg, 0.198 mmol) in 4 ml of anhydrous $Et_2O$ and 2 ml of anhydrous THF was added over freshly dried 4 Å molecular sieves and cooled to −50° C. Trimethylsilylmethyl trifluoromethanesulfonate (TMSOTf) (3.33 mg, 0.0198 mmol) was added and the mixture stirred at −50° C. for 1 hour. The mixture was allowed to warm to −20° C. and another 3.33 mg of TMSOTf was added. The mixture was then slowly allowed to warm to room temperature and stirred for 3 hour. The solution was then diluted with EtOAc and filtered over celite. The organic layer was washed with saturated aqueous $NaHCO_3$ and brine, dried ($MgSO_4$), and concentrated. The residue was purified by column chromatography on silica gel (toluene:EtOAc 12:1) to give 128 mg (67.5%, 0.134 mmol) of 33.

Compound 34 (36 mg, 0.03 mmol), dissolved in 6 ml of EtOAc, was added to 36 mg of 20 wt % palladium hydroxide in 1 ml of EtOAc and saturated with hydrogen. The reaction vessel was purged with hydrogen, and the mixture was stirred at room temperature overnight. The reaction mixture was filtered and the solvent was evaporated. The above hydrogenated compound was dissolved in 2 ml THF, 1 ml water, and 1 ml methanol. LiOH (9 mg, 0.14 mmol) was added to the solution and the reaction was stirred at room temperature for four hours. 100 mg of $Na_2CO_3$ was added and the mixture stirred for 30 minutes. The solvent was evaporated and the remaining residue was purified on silica gel by column chromatography ($CH_2Cl_2$:MeOH 4:1) to give 7.8 mg of 1 (38%, 0.0114 mmol, 2 steps).

After deprotection of compound 42 (14 mg, 0.017 mmol), $Bu_2SnO$ (6.5 mg, 0.0259 mmol) dissolved in 1 ml of MeOH was added. The mixture was refluxed under argon for 2 h. After evaporation of the solvent, $Me_3N.SO_3$ (5 mg, 0.035 mmol) dissolved in 1 ml THF was added and the reaction was allowed to proceed at room temperature for 6 hours. The solvent was then removed under reduce pressure and the residue dissolved in $CHCl_3$/MeOH 1:1 (1 mL) and loaded onto an ion exchange column (Dowex 50X8 Na+ form). After elution with $CHCl_3$/MeOH 1:1, the mixture was concentrated and purified by column chromatography ($CH_2Cl_2$:MeOH 5:1) to give 18 (14.4 mg, 95%).

1.2 Hybridoma Assay

CD1d reactive T cell hybridomas with an invariant Vα14i T cell antigen receptor a chain were used, as described (Sidobre, S., et al. (2004) Proc. Natl. Acad. Sci. USA 101, 12254-12259). T cell hybridomas were stimulated with the indicated glycolipids that were added either to plates coated with soluble CD1d, or with CD transfected A20 B lymphoma cells, as described (Elewaut, D., et al. (2003) J. Exp. Med. 198, 1133-1146). As a measure of T cell activation, IL-2 release into the tissue culture medium was measured after 16 hours culture by an ELISA assay.

Generation of Vα24i Human NKT Cell Line

Human NKT cell lines, expressing the Vα24i T cell receptor as well as CD161, were generated as follows: Anti-CD161 monoclonal antibodies, and anti-CD14 monoclonal antibodies, each coupled to magnetic beads (Miltenyi biotec, Auburn, Calif.), were used sequentially to isolate CD161+ cells and CD14+ cells from leukopaks. Immature dendritic cells were generated from the CD14+ cells after a two-day incubation in the presence of 300 U/ml GM-CSF (R&D systems, Minneapolis, Minn.) and 100 U/ml IL-4 (R&D systems, Minneapolis, Minn.). Following irradiation with 2000 rads, the immature dendritic cells were co-cultured with syngeneic CD161+ cells in the presence of 100 ng/ml of alpha-galactosylceramide and 10 IU/ml of IL-2 (Invitrogen, Carlsbad Calif.) for 10 to 14 days. After stimulating the CD161+ cells a second time with alpha-galactosylceramide-pulsed, irradiated immature dendritic cells, NKT cell lines were shown by flow cytometry to express both CD161+ and V 24i TCR (99% purity).

In Vitro Cytokine Secretion Assay Using Human NKT Cell Lines

IFN-γ and IL-4 secretion by the Vα24i human NKT cell line was determined by ELISA (BD Pharmingen, San Diego, Calif.) after culture for 16 hours. For these assays, $1 \times 10^5$ Vα24i human NKT cells were co-cultured with $4 \times 10^5$ irradiated, immature CD14+ dendritic cells, in the presence of the glycolipid compounds at 10 µg/ml in a 96-well flat-bottom plate.

Results

In order to test whether glycolipids of bacterial origin (5, 6, 8, 17) (represented in FIG. 5), or analogues thereof, which comprise structures similar to α-GalCer either at the sugar or lipid moiety, activate NKT cells through CD1d, the glycolipids were synthesized and assayed. Analogues 7 and 8 (FIG. 5) were prepared, and used to probe the effect of the carboxyl group on the sugar and the α-hydroxyl group on the lipid. Compounds 19, 10 and 4 contain a 3'-sulfate group with an α or β-glycosidic linkage. 20-23 were prepared to probe the effect of the 2'-modification of α-GalCer. Analogues of α-GalCer with modification of the lipid moiety were also prepared to probe their interaction with CD1d and the subsequent effect on NKT cell activation.

Figure 8A:
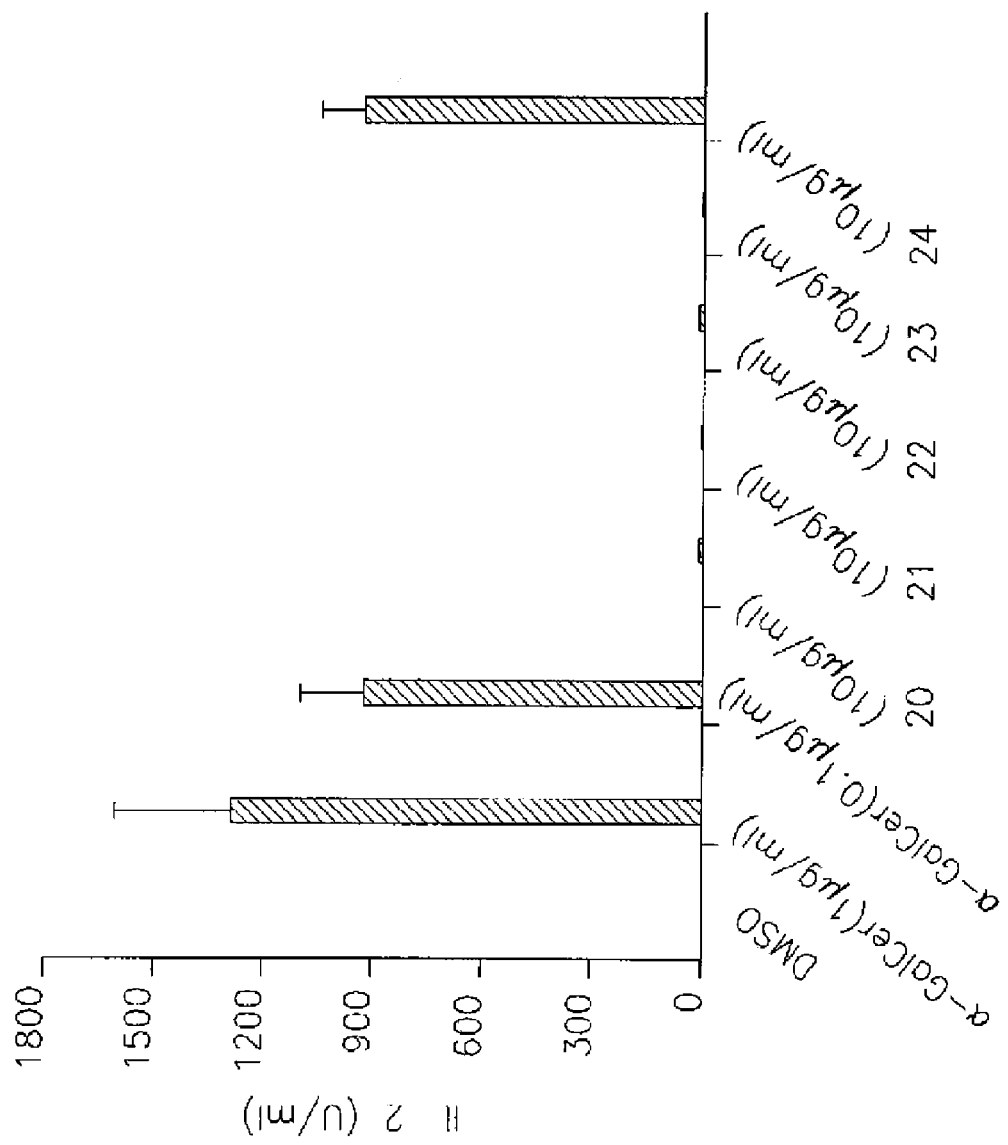
FIG. 8 demonstrates the IL-2 secretion profiles obtained with glycolipids, according to embodiments of the invention. (a) IL-2 secretion profile obtained with 3-O-sulfo-GalCer, as compared to α-GalCer and analogues. (b) Dose dependent secretion of IL-2 by Sphingomonas GSLs and analogues.

Mouse Vα14i NKT cells immortalized by cell fusion provided a convenient method for assaying the ability of the synthetic glycolipids to activate T cells. As shown in FIG. 8a, the 3-O-sulfo-α-GalCer, 4, stimulated significant IL-2 release from the hybridomas when used at 10 µg/ml. Dose response curves indicated, however, that this compound was somewhat less active than α-GalCer (data not shown) in this model. By contrast, every modification of the 2 OH position of the galactose (compounds 10-13) that were tested abolished all biological activity. These data indicate that the Vα14i NKT cell response to glycolipids apparently is more sensitive to modifications of the 2 than to the 3 position.

B. burgdorferi glycolipids (17-18) and compounds 24 and 25 were moderately active in the 1.2 hybridoma assay. However IL-2 secretion could only be detected when large quantities of the glycolipids were used to stimulate the hybridoma cells.

Figure 8B:
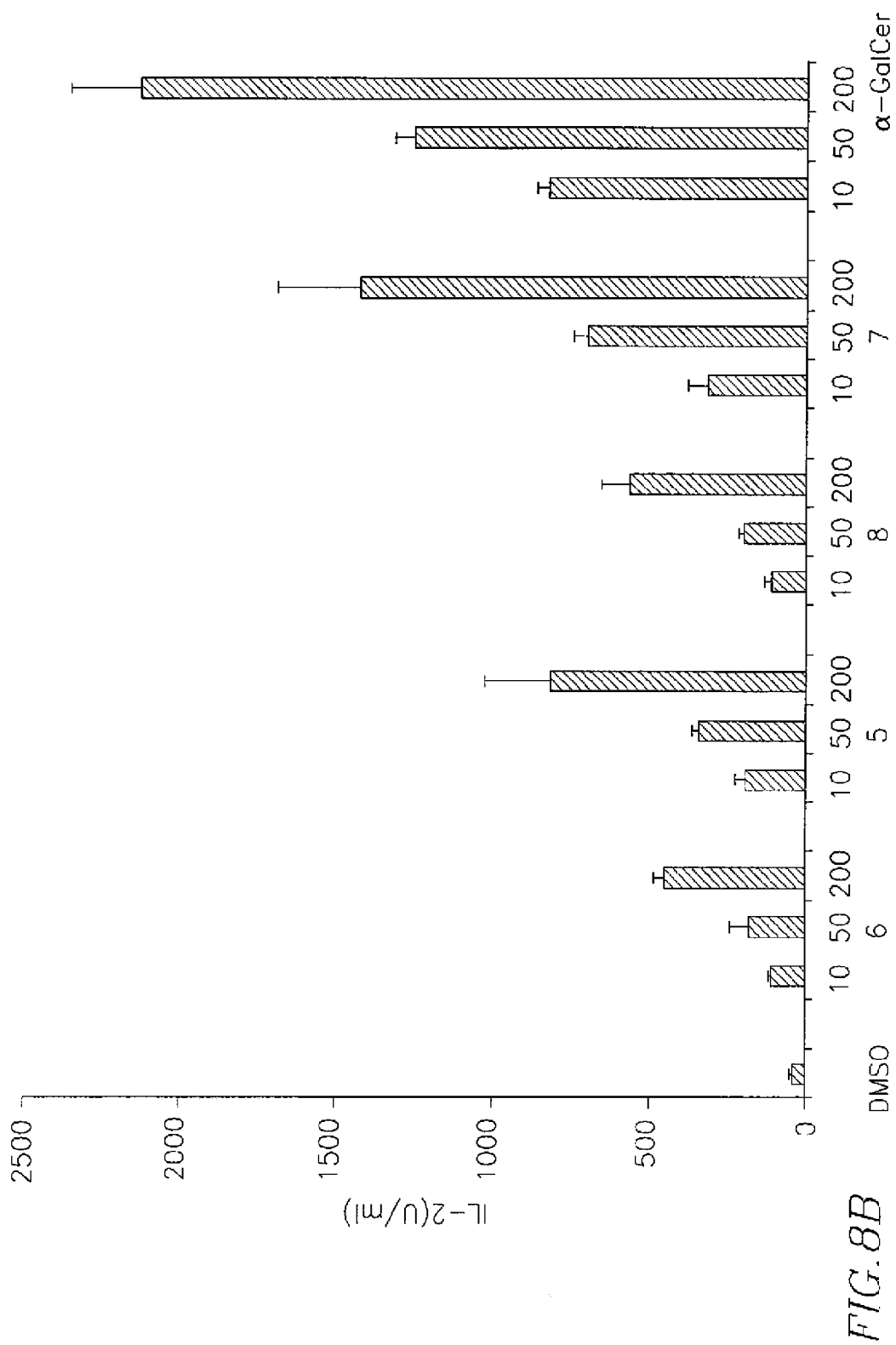

CD1d coated plates were used to assay response of the hybridomas to the *Sphingomonas* glycolipids (FIG. 8b). A substantial level of IL-2 secretion can be observed for all compounds. The structure of the sugar head group significantly affected the activation of the hybridomas. α-GalCer and the galactose analogue 7, consistently solicited greater IL-2 secretion when compared to the galacturonic acid derivatives. Also affecting activity was the (S)-2-hydroxy of the fatty amide tail. A fully saturated tail was more greatly favored, suggesting that the α-hydroxyl group is not optimal. In fact the (S)-2-hydroxy appeared to have a greater affect on activity as compound to compound 8, a galactose analogue, that was less able to activate IL-2 secretion when compared with 5, the galacturonic acid compound without the α-hydroxyl fatty amide. Though 7 and 8 are not known to be natural products, both could be precursors to compounds 5 and 6.

Figure 9C:
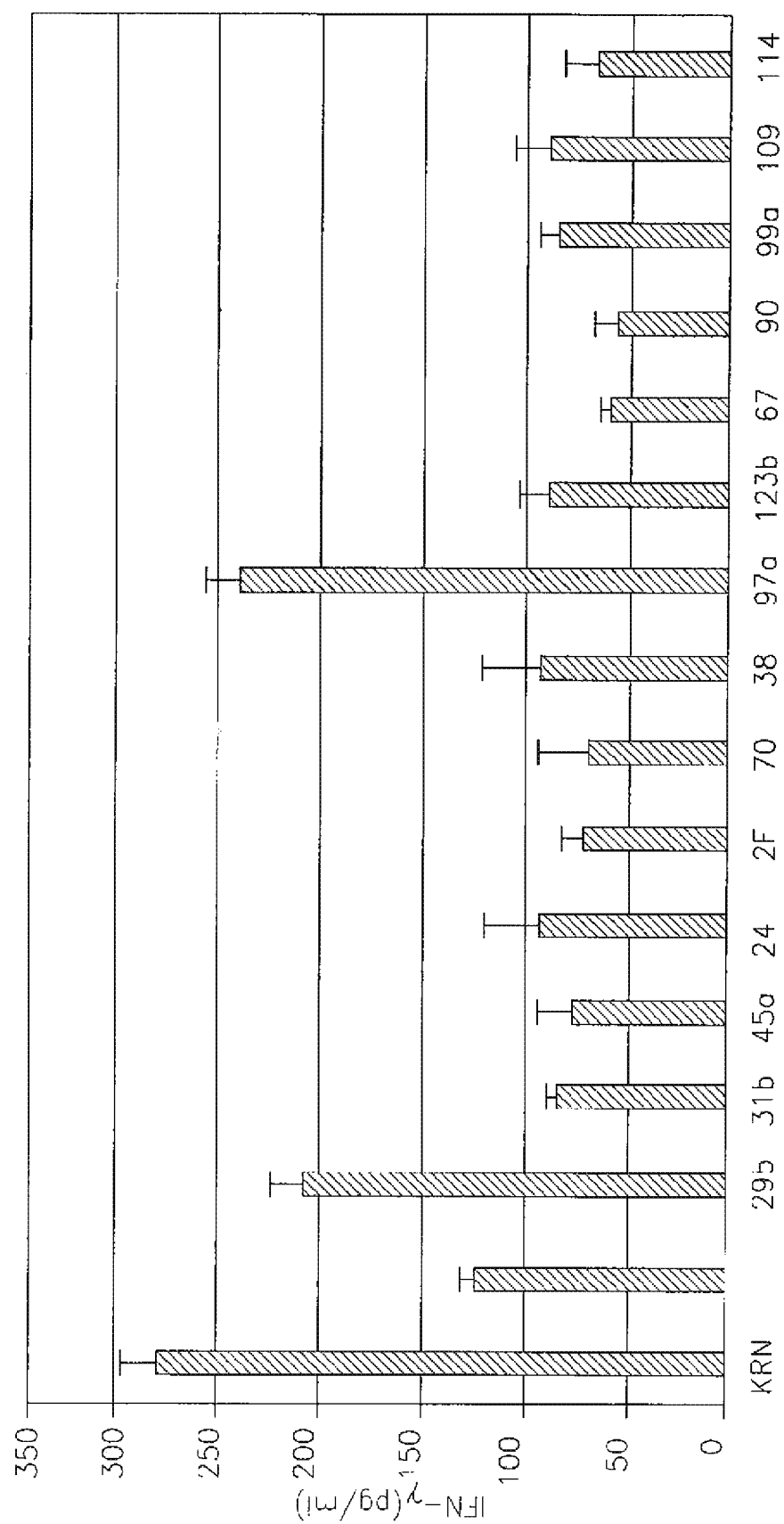
FIG. 9 demonstrates human NKT cell responses to glycolipids, according to embodiments of the invention. Human Vα24i NKT cells respond to synthetic Sphingomonas and sulfatide glycolipids, in terms of IFN-γ (a) and IL-4 (b) release after culture with 4×10$^5$ autologous immature CD14+ dendritic cells pulsed with the indicated glycolipid antigens at 10 μg/ml. Negative controls included similar numbers of NKT cells and dendritic cells, cultured without added glycolipid. Data represent mean±S.D. of duplicate well; (c) in vitro INF-γ secretion by human CD161$^+$ NK+NKT cells (2×10$^5$/well) in the presence of CD14$^+$ DCs (4×10$^5$/well) and 20 μg/ml of various glycolipids; (d) in vitro IL-4 secretion by human CD161$^+$ NK+NKT cells (2×10$^5$/well) in the presence of CD14$^+$ DCs (4×10$^5$/well) and 20 μg/ml of various glycolipids.
Figure 9D:
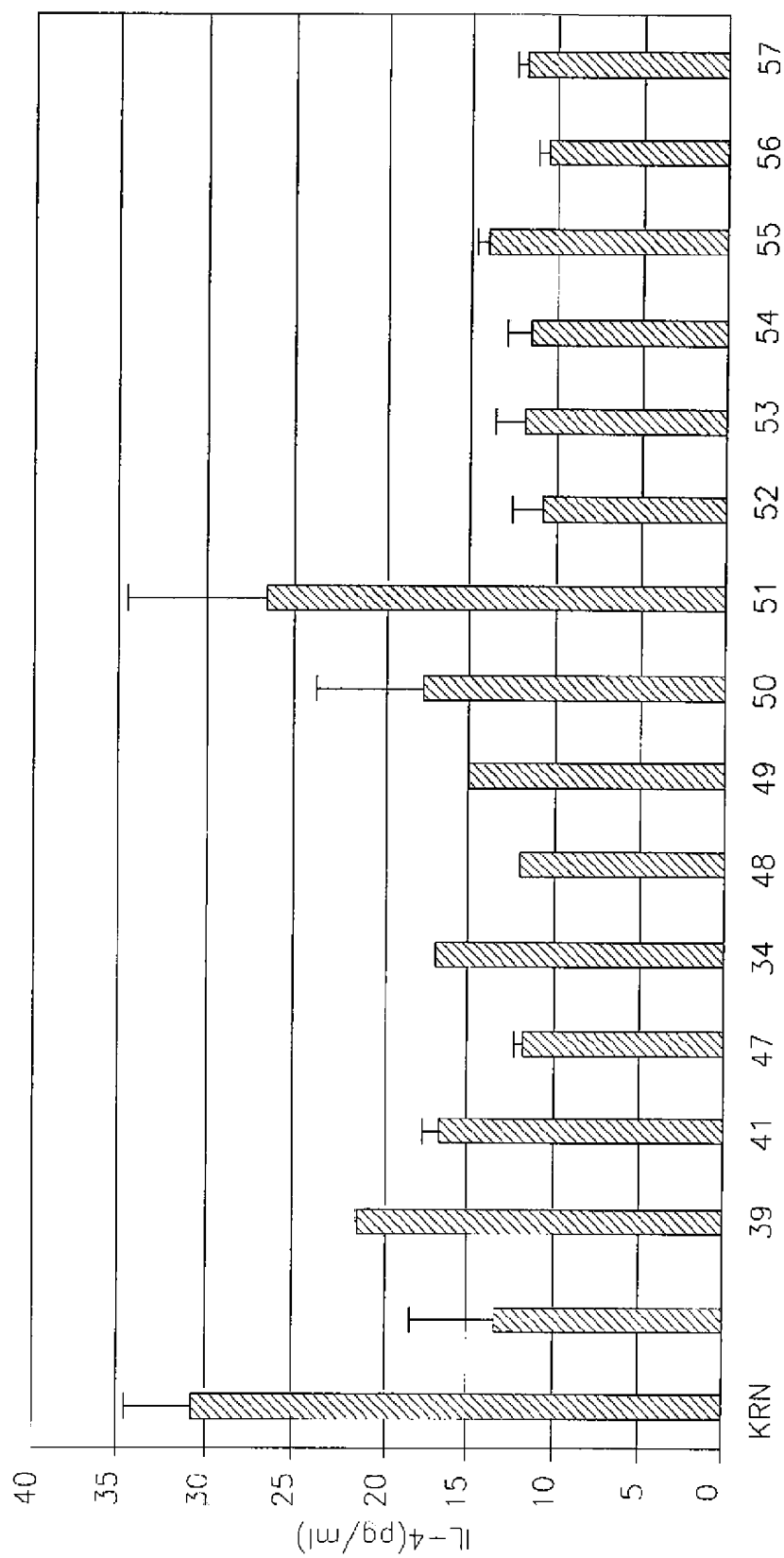

IFN-γ and IL-4 secretion from a Vα24i NKT cell line were assessed, after stimulation with irradiated, syngeneic CD14+ immature dendritic cells in the presence of 10 µg/ml of the glycolipids and 10 IU/ml of IL-2 (FIG. 9a). Stimulation of the NKT cell line by each glycolipid compound resulted in significant IFN-γ and IL-4 secretion, when compared to the negative control. While greater IFN-γ and IL-4 secretion was observed after stimulation by the potent NKT cell agonist, α-GalCer, secretion of IFN-γ and IL-4 by NKT cells stimulated by 1-10 µg/ml of 3-O-sulfo-α-galactosylceramide was approximately half that of α-GalCer, but twice that induced by the other glycolipids. β-linked sulfatides 19 and 10 were also observed to elicit both IFN-γ and IL-4 production. In fact, the level of cytokine secretion was comparable to the GSLs.

As illustrated in FIGS. 8C and 8D, interferon-γ secretion by human NKT cells in response to glycolipid presentation by CD14+ DCs, was superior when the glycolipid was 3-sulfo-α-GalCer 4, as compared to α-GalCer, at a concentration of 10-20 µg/mL. Compound 4 efficiently stimulated IL-4 and IFN-γ secretion, indicating that the modification of the 3"-OH position of the galactose moiety with sulfate was useful in NKT cells stimulation.

NKT cells activation was sensitive to the configuration of the anomeric carbon of glycolipid antigen molecules. 3-sulfo-β-GalCer 10 had minimal to no affinity for NKT lymphocytes due to the β-linkage of glycosidic bond, indicating that the α-linkage of the glycoside was essential for CD1 antigen binding.

Other α-GalCer analogues with an acetyl side chain or a shortened backbone were also tested and some activity was also observed (FIGS. 8C and 8D).

Example 5

Human NKT Cell Lines Bind to Glycolipids in the Context of CD1d

Materials and Methods

In Vitro CD1d-Dimer Assay Using a Human NKT Cell Line

One mg of soluble divalent human CD1d-IgG1 fusion protein (human CD1d-IgG1 dimers, BD Pharmingen) were incubated overnight with 10 M of each glycolipid at 32° C. and at neutral pH according to the manufacturer's protocol. The glycolipid-loaded CD1d-IgG1 dimers were incubated with human NKT cells at 4° C. for 60 minutes, followed by incubation with PE-coupled anti-mouse IgG1 mAb (A85-1). The cells were also surface stained with a PerCP-coupled anti-CD3 mAb (BD Pharmingen, San Diego, Calif.).

Results

Figure 10:
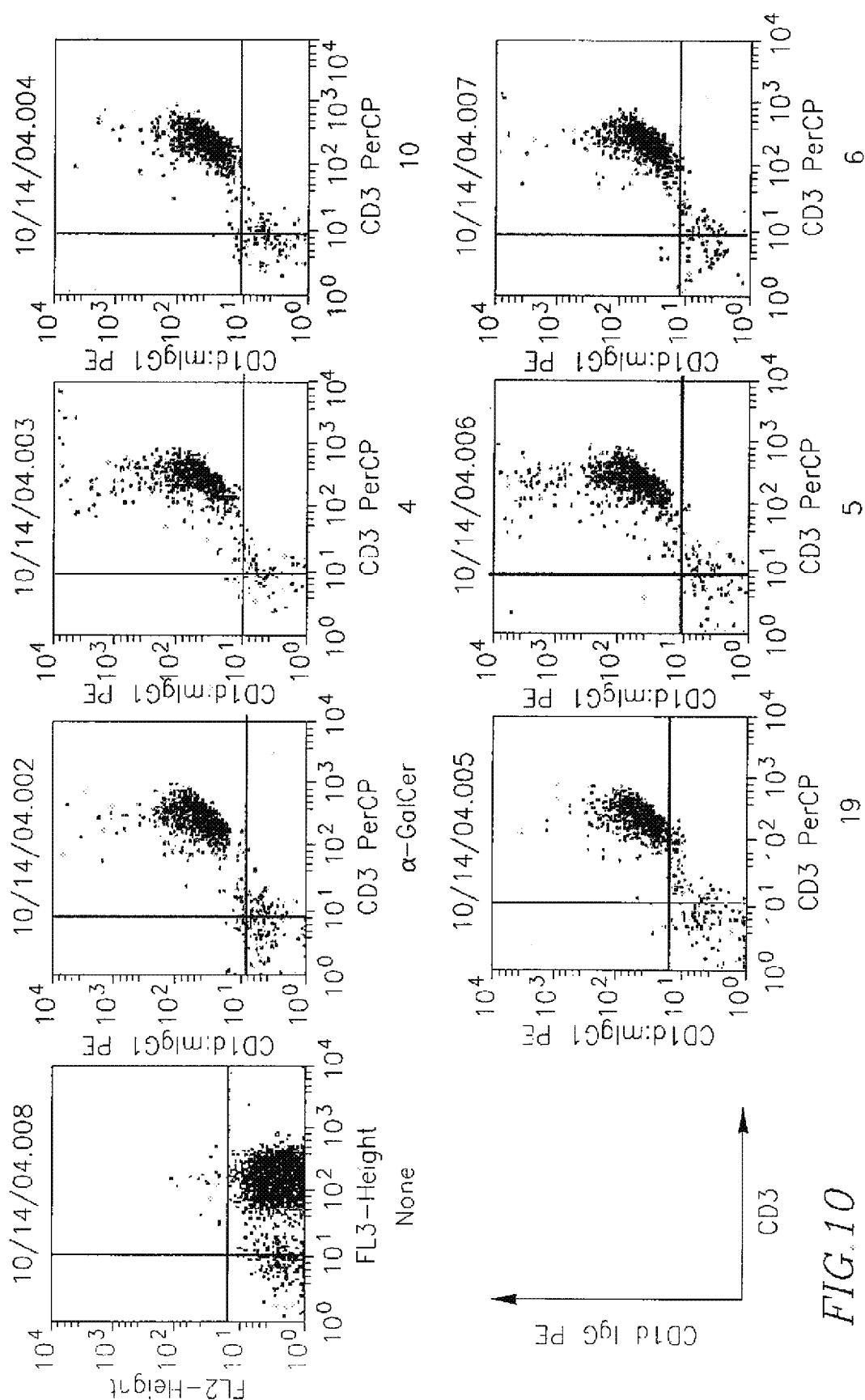
FIG. 10 demonstrates a flow cytometric analysis of a human Vα24i human NKT cell line with human CD1d dimers that were unloaded or loaded with 10M of the indicated glycolipid antigen, according to embodiments of the invention. The cells were also stained with anti-human CD3-PerCP.

Although glycolipids stimulated the NKT cell line, it does not necessarily follow that the glycolipids were presented by CD1d molecules and were capable of triggering the Vα24i T cell receptor expressed by the NKT cells. Therefore, in order to demonstrate glycolipid antigen reactivity to the Vα24i T cell receptor at the single cell level, a human NKT cell line with human CD1d dimers loaded with different glycolipids was stained, and unloaded CD1d dimers were used as a negative control. Each glycolipid-loaded dimer nearly universally stained the human NKT cells, while the unloaded dimer did not stain these cells (FIG. 10).

Example 6

Computer Modeling of GSL Complexed to mCD1d

Materials and Methods

Model Generation

A model of GSL 1 complexed with the crystal structure of mCD1d (Zeng, Z., et al. (1997) Science 277, 339-45) was generated by Autodock 3.0 (Morris, G. M., et al. (1998) J. Comput. Chem. 19, 1639-1662).

Results

Figure 11:
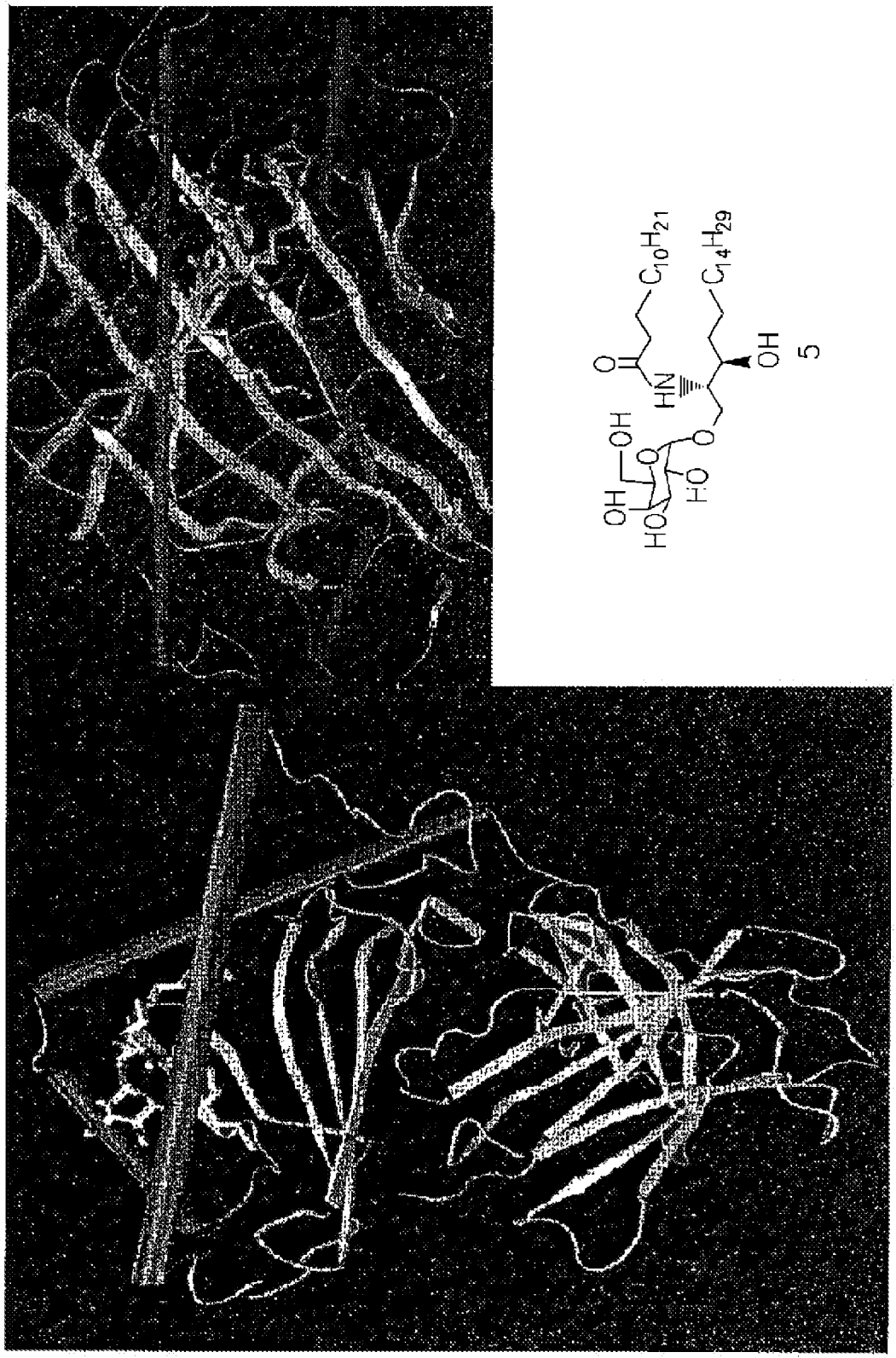
FIG. 11 depicts a computer-generated model of GSL-1 docked to the crystal structure of mCD1d, according to embodiments of the invention. The two acyl tails fit nicely into the hydrophobic pockets of the protein allowing for the sugar head group to be presented for NKT cell recognition.

To further understand the interaction of bacterial glycolipid 1 with CD1d, a model of GSL 1 complexed with mCD1d was generated, and is shown in FIG. 11. According to the model, the fatty acyl chain extended into the F' pocket and the sphingosine chain toward the A' pocket. This allowed for the polar head group to be oriented such that it was exposed for recognition by a T cell antigen receptor. Numerous favorable contacts could be observed between mCD1d and the glycosphingolipid. Among them, possible hydrogen bonding included interactions between the carboxylate of the sugar and the backbone carbonyl of Asp80, and the amide nitrogen of the fatty acid tail with the Asp80 sidechain.

While it was thought that mCD1d to be somewhat accommodating in terms of lipid tail length on NKT cell reactivity, changes in the lipid length, composition, or addition of an α-hydroxyl group on the fatty acid, as seen in FIG. 11, could cause a slight shift in orientation of the sugar and thereby affect CD1d/glycolipid complex recognition by the T-cell receptor. Substitution of galacturonic acid for galactose may produce similar results. The perturbation caused by having the 6-OH oxidized to a carboxylic acid caused only moderate changes in NKT cell reactivity, thus the model provides an effective means for designing additional ligands.

Example 7

Synthesis of Analogues of Glycolipid α-Galactosyl Ceramide

A number of glycolipids were synthesized and tested for NKT cell activation. A synthetic scheme is provided in scheme 1 below:

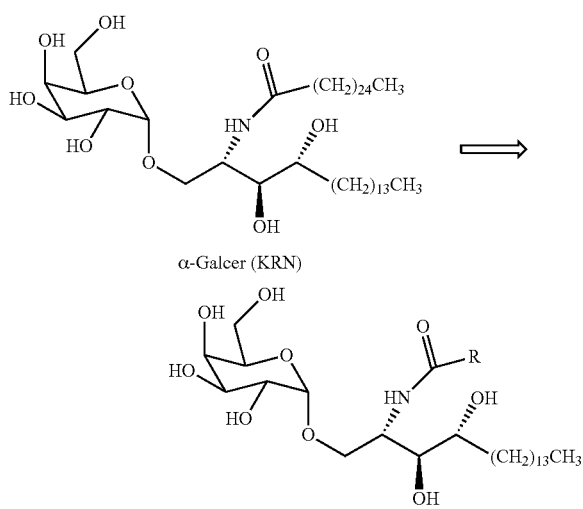

Scheme 1
Synthesis of Fatty Acid Analogues of α-Galcer wherein R is selected from Table 1 below to provide the corresponding compound.

TABLE 1

| Compound No. | R = |
|---|---|
| 58 | phenyl |
| 59 | 4-(trifluoromethyl)phenyl |
| 60 | benzyl (–CH$_2$–C$_6$H$_5$) |
| 61 | (benzo[d][1,3]dioxol-5-yl)methyl |
| 62 | 2-(4-methoxyphenyl)ethyl |
| 63 | 5-(4-chlorophenyl)furan-2-yl |

TABLE 1-continued
| Compound No. | R = |
|---|---|
| 64 | 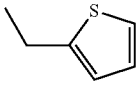 |
| 65 | 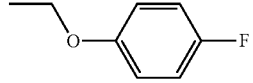 |
| 66 | 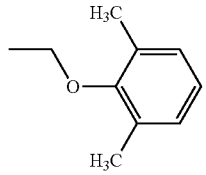 |
| 67 | 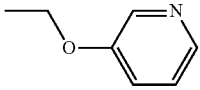 |
| 68 | 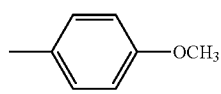 |
| 69 | 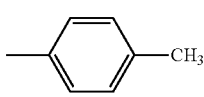 |
| 70 | 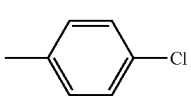 |
| 71 | 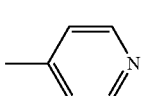 |
| 72 | 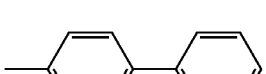 |
| 73 | 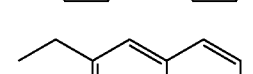 |
| 74 | 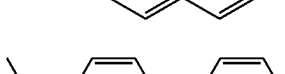 |
| 75 | 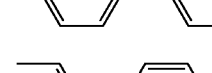 |
| 76 | 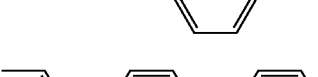 |
| 77 | 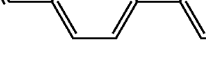 |

TABLE 1-continued

| Compound No. | R = |
|---|---|
| 78 | 3-ethyl-4-phenyl-1,3-oxazolidin-2-one (4S) |
| 79 | 2-methyl-5-(4-nitrophenyl)furan |
| 80 | 3-methylpyridine |
| 81 | 5-chloro-2-methyl-1H-indole |
| 82 | 4-phenylbutyl |
| 83 | 6-phenylhexyl |
| 84 | 8-phenyloctyl |
| 85 | 11-phenylundecyl |
| 86 | 1-propyl-4-(trifluoromethyl)benzene |
| 87 | 1-propyl-4-(trifluoromethyl)benzene |
| 88 | 1-ethyl-4-fluorobenzene (via 2-(4-fluorophenyl)ethyl) |
| 89 | 9-ethyl-9H-fluorene |

TABLE 1-continued

| Compound No. | R = |
|---|---|
| 90 | 1,1-diphenylpropyl group |
| 91 | 3-(piperidin-1-yl)propyl group |
| 92 | 4-(isobutyl)phenylpropyl group (propyl attached to phenyl bearing i-Bu) |
| 93 | 3-(biphenyl-4-yl)propyl group |
| 94 | 5-phenylpentyl group |
| 95 | 6-phenylhexyl group |
| 96 | 8-phenyloctyl group |
| 97 | 10-phenyldecyl group |
| 98 | 15-phenylpentadecyl group |
| 99 | 18-phenyloctadecyl group |
| 100 | 22-phenyldocosyl group |
| 101 | 5-(4-methoxyphenyl)pentyl group |
| 102 | 7-(4-methoxyphenyl)heptyl group |
| 103 | 5-(4-fluorophenyl)pentyl group |

TABLE 1-continued
| Compound No. | R = |
|---|---|
| 104 | 4-fluorophenyl-hexyl |
| 105 | 4-fluorophenyl-nonyl |
| 106 | 4-(trifluoromethyl)phenyl-pentyl |
| 107 | 4-(trifluoromethyl)phenyl-hexyl |
| 108 | 4-(trifluoromethyl)phenyl-nonyl |
| 109 | 4-biphenyl-pentyl |
| 110 | 4-biphenyl-hexyl |
| 111 | 4-biphenyl-nonyl |
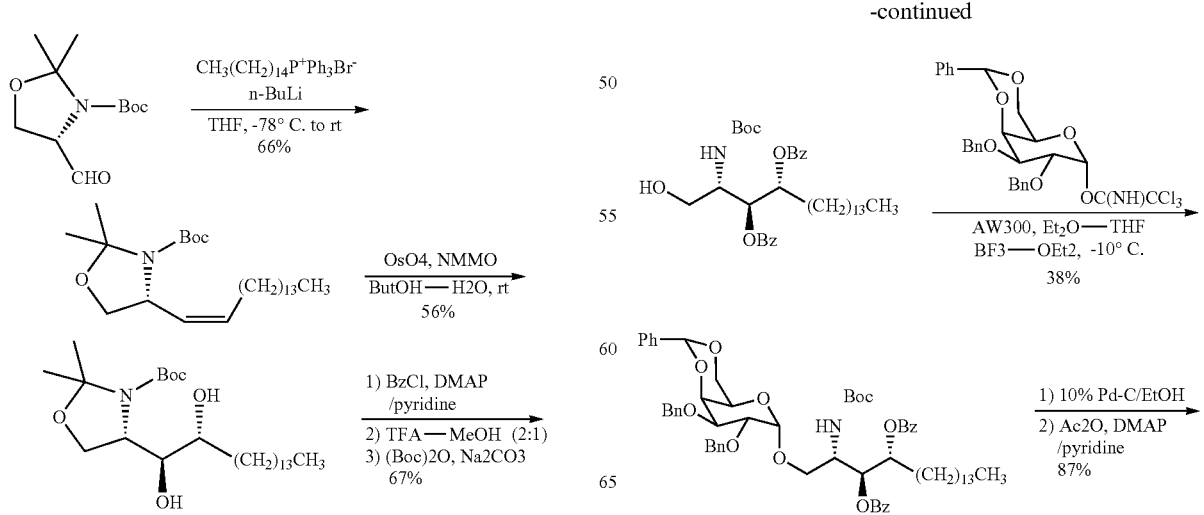

-continued

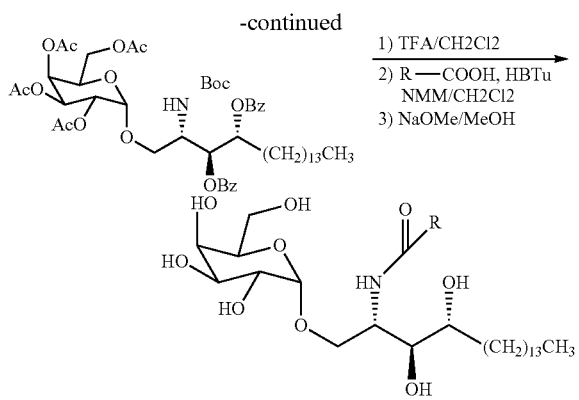

Other compounds were synthesized as described in Xing G W et al. Bioorg Med Chem. 2005 Apr. 15; 13(8):2907-16; and Wu D. et al., Proc Natl Acad Sci USA. 2005 Feb. 1; 102(5): 1351-6.

All chemicals were purchased as reagent grade and used without further purification. Dichloromethane ($CH_2Cl_2$) were distilled over calcium hydride. Tetrahydrofuran (THF) and ether were distilled over sodium metal/benzophenone ketyl. Anhydrous N,N-dimethylformamide (DMF) was purchased from Aldrich. Molecular sieves (MS) for glycosylation were AW300 (Aldrich) and activated by flame. Reactions were monitored with analytical thin layer chromatography (TLC) in EM silica gel 60 F254 plates and visualized under UV (254 nm) and/or staining with acidic ceric ammonium molybdate or ninhydrin. Flash column chromatography was performed on silica gel 60 Geduran (35-75 um, EM Science). $^1H$ NMR spectra were recorded on a Bruker DRX-500 (500 MHz) spectrometer or a Bruker DRX-600 (600 MHz) spectrometer at 20° C. Chemical shifts (δ ppm) were assigned according to the internal standard signal of tetramethylsilane in $CDCl_3$ (δ=0 ppm). $^{13}C$ NMR spectra were obtained using Attached Proton Test (APT) on a Bruker DRX-500 (125 MHz) spectrometer Bruker DRX-600 (150 MHz) spectrometer and were reported in δ ppm scale using the signal of $CDCl_3$ (δ=77.00 ppm) for calibration. Coupling constants (J) are reported in Hz. Splitting patterns are described by using the following abbreviations: s, singlet; brs, broad singlet; d, doublet; t, triplet; q, quartet; m, multiplet. $^1H$ NMR spectra are reported in this order: chemical shift; number(s) of proton; multiplicity; coupling constant(s).

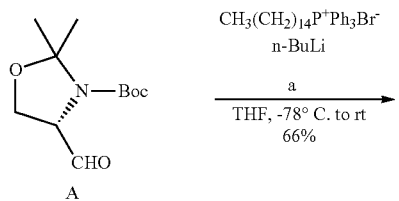

To a stirred solution of Wittig reagent a (6.1 g, 11 mmol), prepared from 1-bromopentadecane and triphenylphosphine refluxed in toluene for 5 days, in THF (30 mL) was added n-BuLi (1.6 mol/L in hexane, 6.4 mL, 10 mmol) dropwise at −78° C., then the solution was stirred for 1 h at room temperature. After 1 h the solution was cooled to −78° C. and Garner's aldehyde A (2.1 g, 9.2 mmol) in THF (20 mL) was added. After stirring for 1 h at room temperature, the solution was poured into ice-water and extracted with AcOEt. The organic layer was washed with brine, dried with $MgSO_4$, and evaporated to dryness. The residue was purified by flash column chromatography on silica gel (toluene 100%) to give B (2.6 g, 66%) as a pale yellow oil. $^1H$ NMR (600 MHz, $CDCl_3$) δ 5.36-5.52 (2H, m), 4.51-4.75 (1H, m), 4.05 (1H, dd, J=6.3 Hz, 8.6 Hz), 3.63 (1H, dd, J=3.3 Hz, 8.6 Hz), 1.94-2.21 (2H, m), 1.20-1.66 (39H, m), 0.88 (1H, t, J=6.9 Hz). $^{13}C$ NMR (150 MHz, $CDCl_3$) δ 151.97, 131.98 (brs), 130.70 (brs), 130.28 (brs), 129.36 (brs), 93.94 (brs), 93.38 (brs), 79.69 (brs), 69.04, 54.55, 31.90, 29.72, 29.67, 29.65, 29.63, 29.59, 29.49, 29.33, 29.29, 28.46, 22.66, 14.08. HRMS (ESI-TOF) for $C_{26}H_{49}NO_3Na^+$ $[M+Na]^+$ calcd 446.3604, found 446.3602.

Synthesis of Compound C:

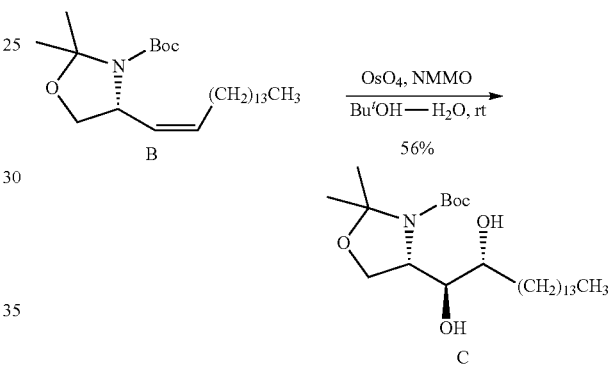

To a stirred solution of B (2.6 g, 6.0 mmol) and 1-methylmorpholine N-oxide (1.1 g, 9.0 mmol) in $Bu^tOH$ and $H_2O$ (1:1, 30 mL), $OsO_4$ (2.5 w/v in $Bu^tOH$, 3.1 mL) was added at room temperature. The solution was stirred overnight and quenched with $Na_2SO_3$ aq. The solution was extracted 2 times with AcOEt, washed with brine, dried with $MgSO_4$, and evaporated to dryness. The residue was purified by flash column chromatography on silica gel ($CHCl_3$ to $CHCl_3$:MeOH 20:1) to give C (1.6 g, 56%) as a white solid. $^1H$ NMR (600 MHz, $CDCl_3$) δ 4.13-4.21 (2H, m), 3.95-4.03 (1H, m), 3.55-3.65 (1H, m), 3.29-3.42 (2H, m), 1.38-1.68 (17H, m), 1.21-1.38 (24H, m), 0.88 (3H, t, J=7.1 Hz). $^{13}C$ NMR (125 MHz, $CDCl_3$) δ: 153.93, 93.97, 81.35, 74.89, 73.85, 65.26, 59.41, 32.27, 31.87, 29.65, 29.63, 29.59, 29.31, 28.31, 26.80, 26.18, 23.94, 22.64, 14.07. HRMS (ESI-TOF) for $C_{26}H_{51}NO_5Na^+$ $[M+Na]^+$ calcd 480.3659, found 480.3659.

Synthesis of Compound D:

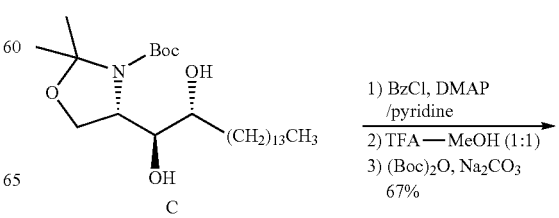

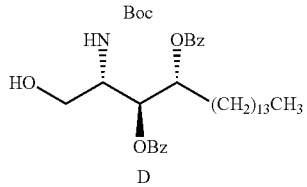

To a stirred solution of C (328 mg, 0.72 mmol) and DMAP (cat.) in pyridine (5 mL) was added BzCl (0.20 mL, 1.8 mmol) and stirred at room temperature overnight. The solution was added Sat. NaHCO$_3$ aq., extracted with AcOEt, washed with brine, dried with MgSO$_4$, and evaporated to dryness. The residue was purified by flash column chromatography on silica gel (Hex.:AcOEt 10:1) to give dibenzoylated product (471 mg) as a colorless oil. To a stirred solution of this compound in dry MeOH (5 mL) was added TFA (10 mL) dropwise at 0° C. After 2 h, the solution was evaporated to dryness and co-evaporated with toluene 3 times. The residue was dissolved in dioxane (15 mL) and Sat. NaHCO$_3$ aq. (15 mL). To a stirred solution, Na$_2$CO$_3$ (155 mg) and Boc$_2$O (320 mg, 1.5 mmol) were added and stirred overnight. This solution was extracted with AcOEt, washed brine, dried with MgSO$_4$ and evaporated to dryness. The residue was purified by flash column chromatography on silica gel (Hex.:AcOEt 5:1) to give D (301 mg, 67% over 3 steps) as a colorless oil. $^1$H NMR (500 MHz, CDCl$_3$) δ: 8.05 (2H, d, J=7.2 Hz), 7.95 (2H, d, J=7.1 Hz), 7.63 (1H, t, J=7.5 Hz), 7.46-7.54 (3H, m), 7.38 (2H, t, J=7.5 Hz), 5.50 (1H, d, J=9.6 Hz), 5.40 (1H, dd, J=2.4 Hz, 9.3 Hz), 5.33 (1H, d, J=9.5 Hz), 4.00-4.07 (1H, m), 3.64-3.67 (2H, m), 2.55-2.65 (1H, m), 1.96-2.10 (2H, m), 1.48 (9H, s), 1.20-1.45 (24H, m), 0.88 (3H, t, J=7.0 Hz). $^{13}$C NMR (125 MHz, CDCl$_3$) δ: 167.03, 166.15, 155.54, 133.73, 133.04, 129.95, 129.64, 129.15, 128.75, 128.63, 128.36, 80.00, 73.81, 73.72, 60.40, 51.46, 31.90, 29.67, 29.65, 29.63, 29.59, 29.53, 29.51, 29.34, 28.30, 25.72, 22.67, 14.11. HRMS (ESI-TOF) for C$_{37}$H$_{55}$NO$_7$Na$^+$ [M+Na]$^+$ calcd 648.3871, found 648.3866.

Synthesis of Compound E:

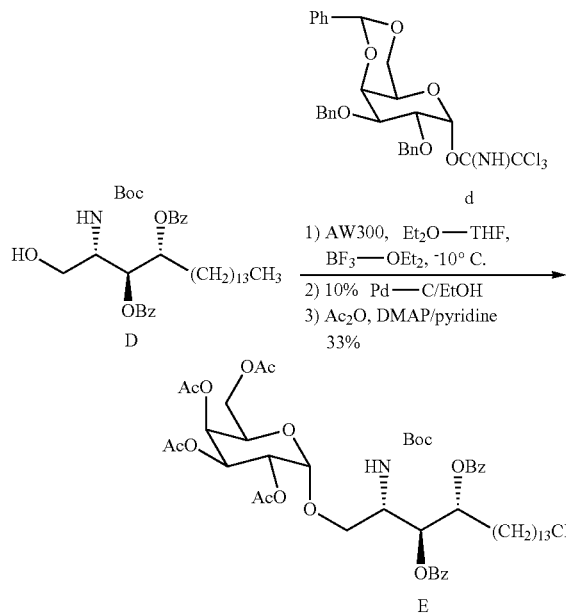

To a stirred solution of D (1.5 g, 2.5 mmol), d (1.8 g, 3.0 mmol) and AW300 (2.0 g) in Et$_2$O-THF (7:1, 34 mL) was cooled to −40° C. and added BF$_3$.OEt$_2$ (0.63 mL, 5 mmol). The solution was stirred for 4 h at ambient temperature, and warmed to room temperature. The solution was filtered, added sat. NaHCO$_3$ aq. and extracted with AcOEt. The organic layer was dried with MgSO$_4$ and evaporated to dryness. The residue was purified by flash column chromatography on silica gel (Hex.:AcOEt 5:1) to give a coupled product (980 mg, 38%) as a colorless oil.

To a stirred solution of this compound (980 mg, 0.95 mmol) in EtOH (30 mL) was added 10% Pd—C (490 mg) and stirred vigorously under H$_2$ atmosphere overnight. The solution was filtered and concentrated to dryness. The residue and DMAP (cat.) were dissolved with pyridine (10 mL) and Ac$_2$O (10 mL), stirred at room temperature overnight. The solution was concentrated, dissolved with AcOEt, washed with brine and concentrated to dryness. The residue was purified by flash column chromatography on silica gel (Hex.:AcOEt 2:1) to give E (790 mg, 87%) as a colorless oil. $^1$H NMR (600 MHz, CDCl$_3$) δ: 8.00 (2H, d, J=7.3 Hz), 7.93 (2H, d, J=7.5 Hz), 7.60 (1H, t, J=7.4 Hz), 7.52 (1H, t, J=7.4 Hz), 7.47 (2H, t, J=7.8 Hz), 7.37 (2H, t, J=7.7 Hz), 5.66 (1H, dd, J=2.3 Hz, 9.6 Hz), 5.41-5.48 (2H, m), 5.29-5.33 (2H, m), 5.16 (1H, dd, J=3.6 Hz, 10.9 Hz), 4.82 (1H, d, J=3.5 Hz), 4.26 (1H, t, J=9.8 Hz), 4.17 (1H, t, J=6.7 Hz), 4.06 (1H, dd, J=6.1 Hz, 11.3 Hz), 4.00 (1H, dd, J=7.1 Hz, 11.3 Hz), 3.78 (1H, dd, J=2.4 Hz, 10.7 Hz), 3.49 (1H, dd, J=2.4 Hz, 10.7 Hz), 2.10 (3H, s), 2.02 (3H, s), 1.99 (3H, s), 1.98 (3H, s), 1.90-1.99 (2H, m), 1.52 (9H, s), 1.20-1.37 (24H, m), 0.88 (3H, t, J=7.0 Hz). $^{13}$C NMR (150 MHz, CDCl$_3$) □: 170.58, 170.28, 170.11, 170.01, 166.11, 164.97, 155.11, 133.34, 132.90, 129.92, 129.70, 129.56, 129.37, 129.52, 128.22, 97.35, 80.28, 73.88, 71.81, 67.84, 67.70, 67.60, 66.97, 66.50, 61.67, 49.94, 31.83, 29.60, 29.58, 29.56, 29.51, 29.43, 29.27, 29.20, 28.27, 28.13, 25.63, 22.60, 20.60, 20.58, 20.52, 20.49, 14.05. HRMS (ESI-TOF) for C$_{51}$H$_{73}$NO$_{16}$Na$^+$ [M+Na]$^+$ calcd 978.4821, found 978.4814.

Alternatively, to a stirred solution of D (1.0 g, 1.6 mmol) d (1.4 g, 2.4 mmol) and AW300 (2.0 g) in Et2O-THF (2:1, 30 mL) was cooled to −30° C. and added TMSOTf (18 µL, 0.081 mmol). The solution was stirred for 1 h at ambient temperature, and d (0.9 g, 1.5 mmol) and TMSOTf (20 µL, 0.090 mmol) was added. The solution was stirred an additional 1 h and then warmed to −10° C. The solution was added triethylamine (2 mL), then filtered, added sat. NaHCO$_3$ aq. and extracted with AcOEt. The organic layer was dried with MgSO4 and evaporated to dryness. The residue was purified by flash column chromatography on silica gel (Hex.:AcOEt 5:1) to give a coupled product (1.3 g, 77%) as a colorless oil.

To a stirred solution of this compound (1.3 g, 1.2 mmol) in AcOEt (30 mL) and EtOH (30 mL) was added 10% Pd—C (600 mg) and stirred vigorously under H$_2$ atmosphere overnight. The solution was filtered and concentrated to dryness. The residue and DMAP (cat.) were dissolved in pyridine (10 mL) and Ac$_2$O (10 mL), stirred at room temperature overnight. The solution was concentrated, dissolved with AcOEt, washed with brine and concentrated to dryness. The residue was purified by flash column chromatography on silica gel (Hex.:AcOEt 2:1) to give 42 (1.1 g, 93%) as a colorless oil. $^1$H NMR (600 MHz, CDCl$_3$) δ: 8.00 (2H, d, J=7.3 Hz), 7.93 (2H, d, J=7.5 Hz), 7.60 (1H, t, J=7.4 Hz), 7.52 (1H, t, J=7.4 Hz), 7.47 (2H, t, J=7.8 Hz), 7.37 (2H, t, J=7.7 Hz), 5.66 (1H, dd, J=2.3 Hz, 9.6 Hz), 5.41-5.48 (2H, m), 5.29-5.33 (2H, m), 5.16 (1H, dd, J=3.6 Hz, 10.9 Hz), 4.82 (1H, d, J=3.5 Hz), 4.26 (1H, t, J=9.8 Hz), 4.17 (1H, t, J=6.7 Hz), 4.06 (1H, dd, J=6.1 Hz, 11.3 Hz), 4.00 (1H, dd, J=7.1 Hz, 11.3 Hz), 3.78 (1H, dd, J=2.4 Hz, 10.7 Hz), 3.49 (1H, dd, J=2.4 Hz, 10.7 Hz), 2.10 (3H, s), 2.02 (3H, s), 1.99 (3H, s), 1.98 (3H, s), 1.90-1.99 (2H, m), 1.52 (9H, s), 1.20-1.37 (24H, m), 0.88 (3H, t, J=7.0 Hz). $^{13}$C NMR (150 MHz, CDCl$_3$) δ: 170.58, 170.28, 170.11, 170.01, 166.11, 164.97, 155.11, 133.34, 132.90, 129.92, 129.70, 129.56, 129.37, 129.52, 128.22, 97.35, 80.28, 73.88, 71.81, 67.84, 67.70, 67.60, 66.97, 66.50, 61.67, 49.94, 31.83, 29.60, 29.58, 29.56, 29.51, 29.43, 29.27, 29.20, 28.27, 28.13, 25.63, 22.60, 20.60, 20.58, 20.52, 20.49, 14.05. HRMS (ESI-TOF) for $C_{51}H_{73}NO_{16}Na^+$ [M+Na]$^+$ calcd 978.4821, found 978.4814.

General procedure of synthesis of fatty acid chain analogues was as follows:

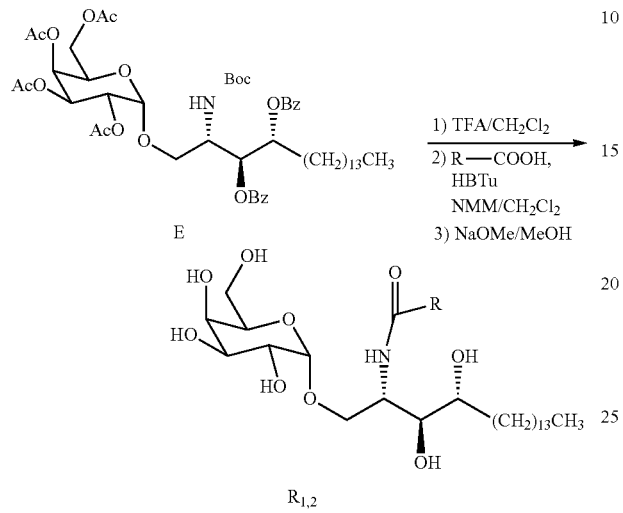

To a stirred solution of E (240 mg, 0.25 mmol) in CH$_2$Cl$_2$ (2.4 mL) was added TFA (2.4 mL) at 0° C. and stirred for 2 h at ambient temperature. The solution was evaporated to dryness and co-evaporated with toluene 3 times to give deprotected amine. This compound was dissolved in CH$_2$Cl$_2$ and used for the next reaction without further purification.

To the deprotected amine (0.021 mmol) in CH$_2$Cl$_2$ (1.0 mL) was added R—COOH (0.031 mmol), HBTu (12 mg, 0.031 mmol) and NMM (31 mg, 0.3 mmol) and stirred at room temperature overnight. The solution was purified by flash column chromatography on silica gel (Hex.:AcOEt 2:1) to give the coupled product as a amorphic solids.

These compounds were dissolved in MeOH (2.0 mL) and 0.5 mol/L NaOMe in MeOH (4 drops) was added. The solution was stirred overnight at room temperature and evaporated to dryness. The residues were purified by flash column chromatography on silica gel (CHCl$_3$:MeOH 10:1) to give R$_{1,2}$.

Compound R$_{1,2}$ were synthesized in a manner similar to that described above.

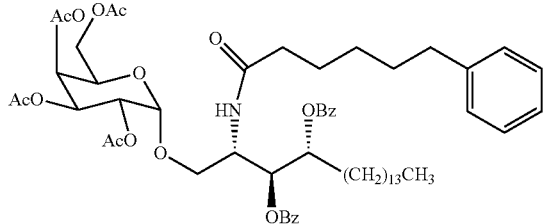

Intermediate of R$_1$: Yield 28 mg (65%). $^1$H NMR (600 MHz, CDCl$_3$) □: 8.00 (2H, dd, J=1.2 Hz, 8.2 Hz), 7.91 (2H, dd, J=1.2 Hz, 8.3 Hz), 7.61 (1H, t, J=7.4 Hz), 7.53 (1H, t, J=7.4 Hz), 7.47 (2H, t, J=7.8 Hz), 7.38 (2H, t, J=7.8 Hz), 7.25-7.28 (2H, m), 7.15-7.20 (3H, m), 6.57 (1H, d, J=9.7 Hz), 5.69 (1H, dd, J=2.4 Hz, 9.9 Hz), 5.43 (1H, d, J=3.3 Hz), 5.33 (1H, dd, J=3.4 Hz, 10.9 Hz), 5.29-5.32 (1H, m), 5.15 (1H, dd, J=3.6 Hz, 10.9 Hz), 4.81 (1H, d, J=3.6 Hz), 4.62 (1H, tt, J=2.5 Hz, 9.9 Hz), 4.11 (1H, dd, J=6.6 Hz, 13.3 Hz), 4.05 (1H, dd, J=6.0 Hz, 11.0 Hz), 3.96 (1H, dd, J=7.0 Hz, 11.3 Hz), 3.73 (1H, dd, J=2.8 Hz, 10.9 Hz), 3.49 (1H, dd, J=2.4 Hz, 10.9 Hz), 2.64 (2H, t, J=7.8 Hz), 2.35 (2H, t, J=7.7 Hz), 2.10 (3H, s), 1.994 (3H, s), 1.986 (3H, s), 1.94 (3H, s), 1.89-1.93 (2H, m), 1.66-1.78 (4H, m), 1.42-1.48 (2H, m), 1.18-1.35 (24H, m), 0.87 (3H, t, J=7.1 Hz). $^{13}$C NMR (150 MHz, CDCl$_3$) □: 172.90, 170.59, 170.39, 170.21, 170.15, 166.50, 165.03, 142.53, 133.49, 133.07, 129.87, 129.77, 129.62, 129.30, 128.62, 128.38, 128.32, 128.24, 125.62, 97.29, 74.14, 71.45, 67.90, 67.53, 67.32, 67.10, 66.68, 61.74, 48.18, 36.65, 35.76, 31.90, 31.22, 29.65, 29.63, 29.60, 29.56, 29.53, 29.34, 29.32, 28.99, 27.86, 25.69, 25.57, 22.67, 20.67, 20.62, 20.58, 20.50, 14.11. HRMS (ESI-TOF) for $C_{36}H_{64}NO_9^+$ [M+H]$^+$ calcd 1030.5522, found 1030.5507.

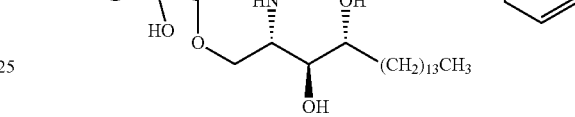

R$_1$: Yield 14 mg (79%). $^1$H NMR (500 MHz, CDCl$_3$-MeOH 4:1) □: 7.25-7.29 (2H, m), 7.15-7.19 (3H, m), 4.90 (1H, d, J=3.9 Hz), 4.17-4.21 (1H, m), 3.94 (1H, d, J=3.2 Hz), 3.87 (1H, d, J=4.7 Hz), 3.67-3.81 (6H, m), 3.51-3.56 (2H, m), 2.61 (2H, t, J=7.8 Hz), 2.20 (2H, t, J=7.6 Hz), 1.44-1.70 (6H, m), 1.21-1.41 (26H, m), 0.88 (3H, t, J=7.0 Hz). $^{13}$C NMR (125 MHz, CDCl$_3$-MeOH 4:1) □: 174.08, 142.25, 128.10, 128.01, 125.42, 99.49, 74.64, 71.86, 70.49, 70.04, 69.53, 68.70, 67.27, 61.69, 50.17, 36.14, 35.46, 32.49, 31.67, 30.93, 29.54, 29.49, 29.46, 29.40, 29.11, 29.00, 28.67, 25.60, 25.40, 22.42, 13.76. HRMS (ESI-TOF) for $C_{36}H_{64}NO_9^+$ [M+H]$^+$ calcd 654.4575, found 654.4568.

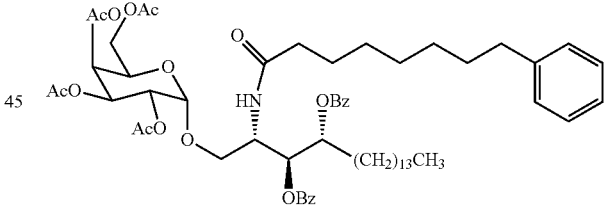

Intermediate of R$_2$: Yield 28 mg (65%). $^1$H NMR (600 MHz, CDCl$_3$) δ: 7.99 (2H, d, J=7.7 Hz), 7.91 (2H, d, J=7.9 Hz), 7.61 (1H, t, J=7.4 Hz), 7.53 (1H, t, J=7.4 Hz), 7.47 (2H, t, J=7.7 Hz), 7.37 (2H, t, J=7.7 Hz), 7.24-7.28 (2H, m), 7.14-7.18 (3H, m), 6.62 (1H, d, J=9.8 Hz), 5.71 (1H, dd, J=2.3 Hz, 9.9 Hz), 5.43 (1H, d, J=3.2 Hz), 5.35 (1H, dd, J=3.3 Hz, 10.9 Hz), 5.29-5.31 (1H, m), 5.15 (1H, dd, J=3.6 Hz, 10.9 Hz), 4.81 (1H, d, J=3.6 Hz), 4.59-4.64 (1H, m), 4.09-4.12 (1H, m), 4.06 (1H, dd, J=5.9 Hz, 11.2 Hz), 3.97 (1H, dd, J=7.0 Hz, 11.3 Hz), 3.73 (1H, dd, J=2.7 Hz, 10.8 Hz), 3.48 (1H, dd, J=2.2 Hz, 10.9 Hz), 2.60 (2H, t, J=7.8 Hz), 2.35 (2H, t, J=7.7 Hz), 2.10 (3H, s), 2.005 (3H, s), 1.996 (3H, s), 1.94 (3H, s), 1.89-1.93 (2H, m), 1.59-1.76 (4H, m), 1.19-1.43 (30H, m), 0.87 (3H, t, J=7.0 Hz). $^{13}$C NMR (150 MHz, CDCl$_3$) □: 172.99, 170.60, 170.38, 17023, 170.16, 166.52, 165.03, 142.80, 133.47, 133.07, 129.87, 129.76, 129.61, 129.30, 128.61, 128.36, 128.31, 128.18, 125.52, 97.24, 74.16, 71.35, 67.93, 67.52, 67.29, 67.12, 66.70, 61.77, 48.15, 36.71, 35.92, 31.89, 31.47, 29.66, 29.63, 29.60, 29.56, 29.53, 29.34, 29.30, 29.26, 29.23, 29.19, 27.80, 25.72, 25.67, 22.66, 20.67, 20.63, 20.58, 20.49, 14.11. HRMS (ESI-TOF) for $C_{60}H_{84}NO_{15}^+$ [M+H]$^+$ calcd 1058.5835, found 1058.5819.

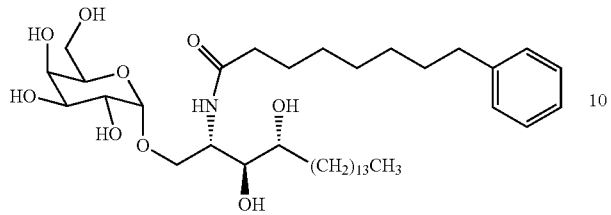

R$_2$: Yield 14 mg (79%). $^1$H NMR (500 MHz, CDCl$_3$-MeOH 4:1) δ: 7.25-7.29 (2H, m), 7.15-7.18 (3H, m), 4.91 (1H, d, J=3.8 Hz), 4.17-4.22 (1H, m), 3.94 (1H, d, J=3.2 Hz), 3.87 (1H, d, J=4.7 Hz), 3.67-3.81 (6H, m), 3.51-3.56 (2H, m), 2.60 (2H, t, J=7.7 Hz), 2.19 (2H, t, J=7.7 Hz), 1.49-1.70 (6H, m), 1.20-1.41 (30H, m), 0.88 (3H, t, J=7.0 Hz). $^{13}$C NMR (125 MHz, CDCl$_3$-MeOH 4:1) □: 174.18, 142.54, 128.11, 127.97, 125.34, 99.49, 74.64, 71.86, 70.48, 70.05, 69.54, 68.71, 67.28, 61.71, 50.17, 36.28, 36.23, 35.67, 32.47, 31.67, 31.24, 29.54, 29.49, 29.47, 29.41, 29.11, 29.04, 29.01, 28.92, 25.60, 25.57, 22.42, 13.76. HRMS (ESI-TOF) for $C_{38}H_{68}NO_9^+$ [M+H]$^+$ calcd 682.4888, found 682.4880.

In general, the phytosphingosine skeleton was constructed by modification of a method described by Savage and co-workers [R. D. Goff, et al. J. Am. Chem. Soc., 2004, 126, 13602-13603] Garner's aldehyde A was coupled with a Wittig reagent prepared from phosphonium bromide B according to Berova's method [O. Shirota, et al., Tetrahedron, 1999, 55, 13643-13658] to give cis olefin B in 66% yield. Treatment of olefin B with osmium tetroxide gave a corresponding diol C and its undesired isomer. The two hydroxyl groups of diol C were protected with benzoyl groups, and then the isopropylidene group was removed by the successive treatment of TFA, followed by Boc anhydride protection to afford phytosphingosine acceptor D in 67% yield over 3 steps.

Glycosylation of phytosphingosine acceptor D and donor d in the presence of BF$_3$.OEt$_2$ gave a predominantly α-configured product. Hydrogenation was avoided as the final deprotection step to ensure accessibility to a more diverse set of compounds. The galactose protecting groups were removed and then protected with acetates to furnish the key intermediate E in 33% over 3 steps.

Compound E was deprotected with TFA to give the deprotected amine. A variety of fatty acyl chain analogues were then couples to the amine to form R after removal of the acetyl groups.

A synthetic scheme for Phytosphingosine Analogues is provided in scheme 2 below:

Synthesis of Phytosphingosine Analogues of α-Galcer

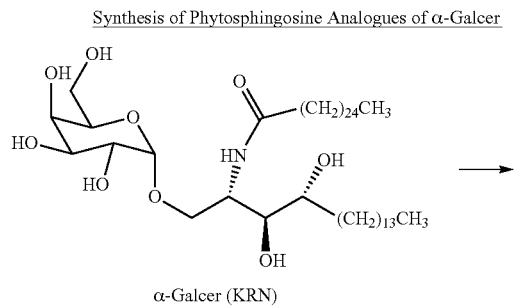

α-Galcer (KRN)

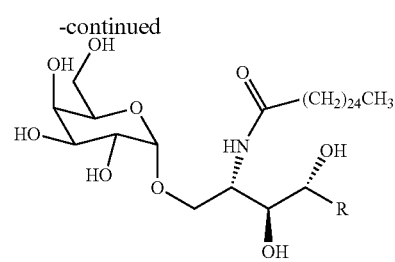

wherein R is selected from Table 2 below to provide the corresponding compound.

TABLE 2

| Compound No. | R = |
|---|---|
| 112 | ![benzyl-ethyl] |
| 113 | ![benzyl-propyl] |

Synthesis of phytosphingosine chain analogues: The synthesis of phytosphingosine chain analogues PC6Ph, PC8Ph, PC11Ph and PC13Ph are summarized in scheme 2. The synthetic route is essentially similar to the one reported in *J. Am. Chem. Soc.* 2006, 128, 9022-9023, supporting information.

Scheme 2. Synthesis of phytosphingosine chain analogues of of a-GalCer.

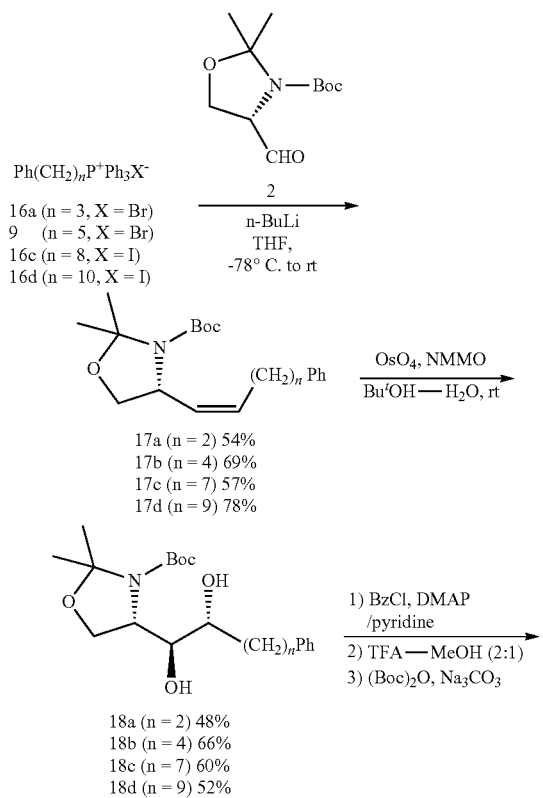

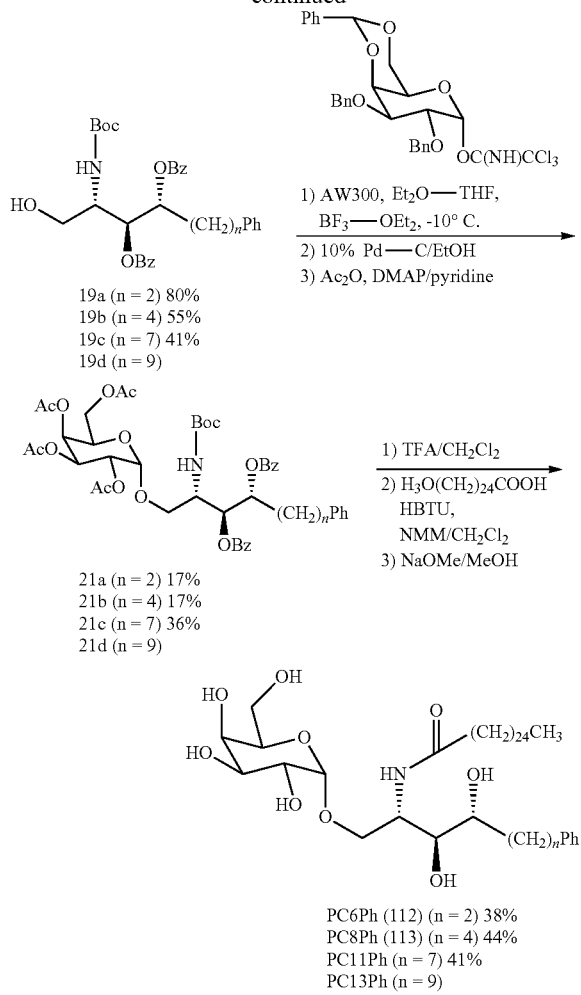

Characterization Data:

Compound 112 (lot. MFJ3-017-1): $^1$H NMR (500 MHz, CDCl$_3$-MeOH 4:1) δ: 7.26 (m, 2H), 7.23-7.19 (m, 2H), 7.18-7.14 (m, 1H), 4.90 (d, J=3.9 Hz, 1H), 4.24-4.19 (m, 1H), 3.86 (dd, J=10.8, 5.2 Hz, 1H), 3.82-3.62 (m, 7H), 3.58-3.53 (m, 2H), 2.92-2.84 (m, 1H), 2.67 (ddd, J=13.7, 9.3, 7.5 Hz, 1H), 2.16 (m, 2H), 2.06-1.98 (m, 1H), 1.74-1.65 (m, 1H), 1.62-1.53 (m, 2H), 1.33-1.19 (m, 44H), 0.88 (t, J=7.0 Hz, 3H). $^{13}$C NMR (125 MHz, CDCl$_3$-MeOH 4:1) δ: 174.06, 141.93, 128.25, 128.01, 125.43, 99.48, 74.60, 70.75, 70.44, 69.99, 69.52, 68.66, 67.03, 61.69, 50.15, 50.06, 36.27, 34.13, 31.67, 31.59, 29.43, 29.31, 29.15, 29.09, 25.55, 22.41, 17.60, 13.76. HRMS (ESI-TOF) for C$_{44}$H$_{80}$NO$_9{}^+$ [M+H]$^+$ calcd 766.5827, found 766.5813.

Compound 113 (lot. MFJ3-018-1): $^1$H NMR (400 MHz, CDCl$_3$-MeOH 4:1) δ: 7.26 (m, 2H), 7.19-7.13 (m, 3H), 4.91 (d, J=3.8 Hz, 1H), 4.20 (q, J=4.4 Hz, 1H), 3.95-3.85 (m, 2H), 3.83-3.61 (m, 6H), 3.59-3.50 (m, 2H), 2.63 (t, J=7.5 Hz, 2H), 2.20 (t, J=7.5 Hz, 2H), 1.78-1.54 (m, 6H), 1.47-1.17 (m, 46H), 0.89 (t, J=6.9 Hz, 3H). $^{13}$C NMR (100 MHz, CDCl$_3$-MeOH 4:1) δ: 174.16, 142.27, 127.91, 127.77, 125.14, 99.33, 74.28, 71.38, 70.42, 69.86, 69.33, 68.51, 66.84, 61.40, 50.02, 36.04, 35.52, 31.93, 31.51, 31.21, 29.26, 29.14, 28.99, 28.94, 25.47, 25.08, 22.25, 13.51. HRMS (ESI-TOF) for C$_{46}$H$_{84}$NO$_9{}^+$ [M+H]$^+$ calcd 794.6140, found 794.6129.

Example 8

Recognition of Glycolipids by Murine NKT Cell Lines Results in IL-2 Secretion Materials and Methods Glycolipids The compound KRN 7000 was purchased (Kirin, Japan). The remaining compounds were synthesized as described hereinabove.

1.2 Hybridoma Assay

CD1d reactive T cell hybridomas with an invariant Vα14i T cell antigen receptor α chain were used, as described (Sidobre, S., et al. (2004) Proc. Natl. Acad. Sci. USA 101, 12254-12259). T cell hybridomas were stimulated with 0.0001-1 µg/ml of the indicated glycolipids added to CD1d transfected A20 B lymphoma cells, as described (Elewaut, D., et al. (2003) J. Exp. Med. 198, 1133-1146). As a measure of T cell activation, IL-2 and IFN-γ release into the tissue culture medium was measured after 16 hours culture by an ELISA assay.

In Vitro Cytokine Secretion Assay Using Human NKT Cell Lines

IL-2 secretion by the Vα24i human NKT cell line was determined by ELISA (BD Pharmingen, San Diego, Calif.) after culture for 16 hours. For these assays, 1×10$^5$ Vα24i human NKT cells were co-cultured with 4×10$^5$ irradiated, immature CD14$^+$ dendritic cells, in the presence of the glycolipid compounds at 10 µg/ml in a 96-well flat-bottom plate [Wu et al. PNAS 2005 102: 1351].

Results

In order to test whether glycolipids with modifications the lipid moiety of α-GalCer affected the immunogenicity of the compound, a series of glycolipids with varied modifications of this region were synthesized and assayed.

Figure 12:
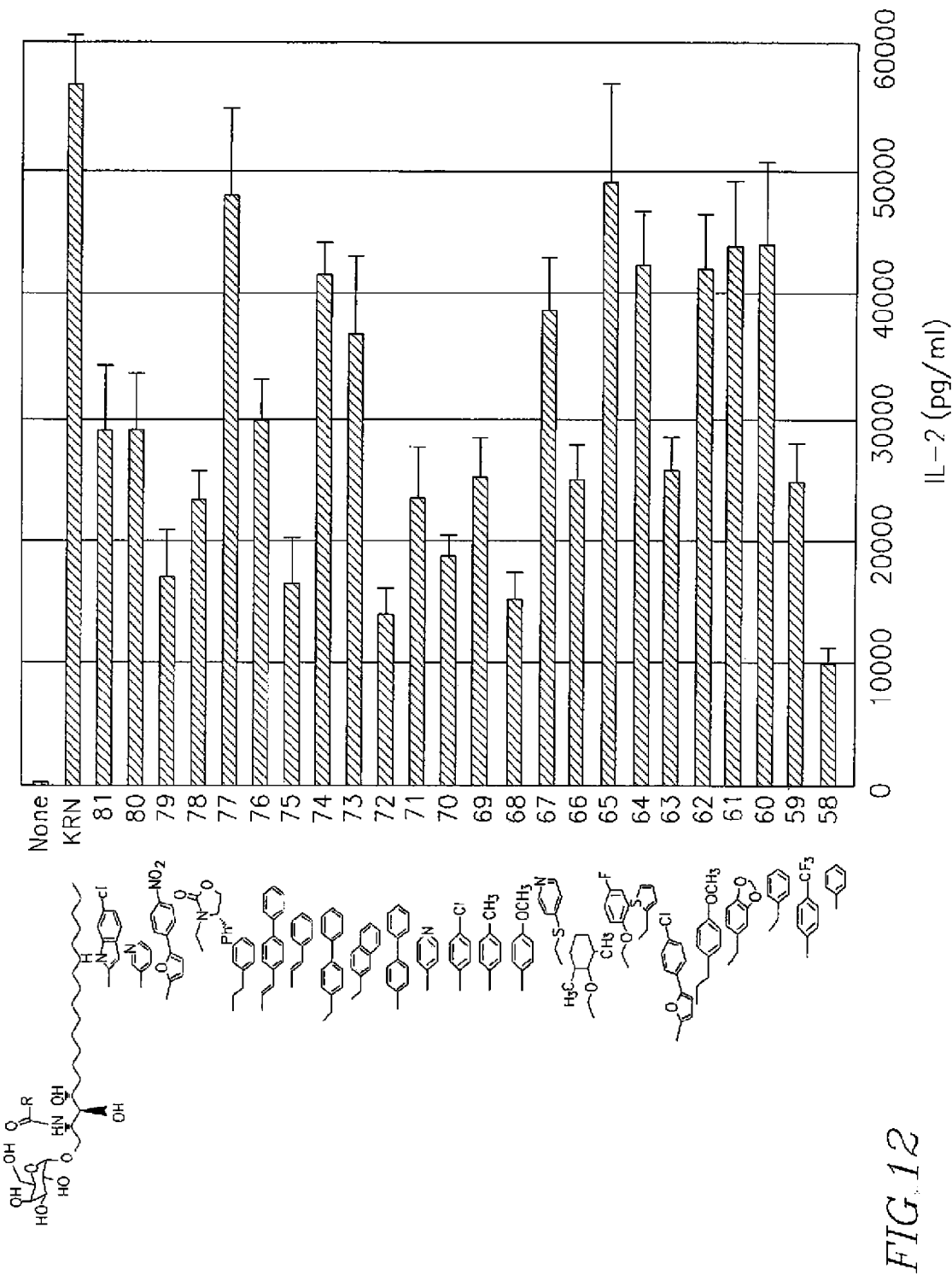
FIG. 12 demonstrates IL-2 secretion profiles obtained from murine NKT cells presented with the glycolipids as indicated, according to embodiments of the invention.

Mouse Vα14i NKT cells immortalized by cell fusion provided a convenient method for assaying the ability of the synthetic glycolipids to activate T cells. As shown in FIG. 12, a number of the compounds (60, 61, 62, 64, 65, 74, 77) stimulated significant IL-2 release from the hybridomas when used at 1 µg/ml, however KRN7000 (α-GalCer) appeared to stimulate the greatest amount of IL-2 release.

Figure 13:
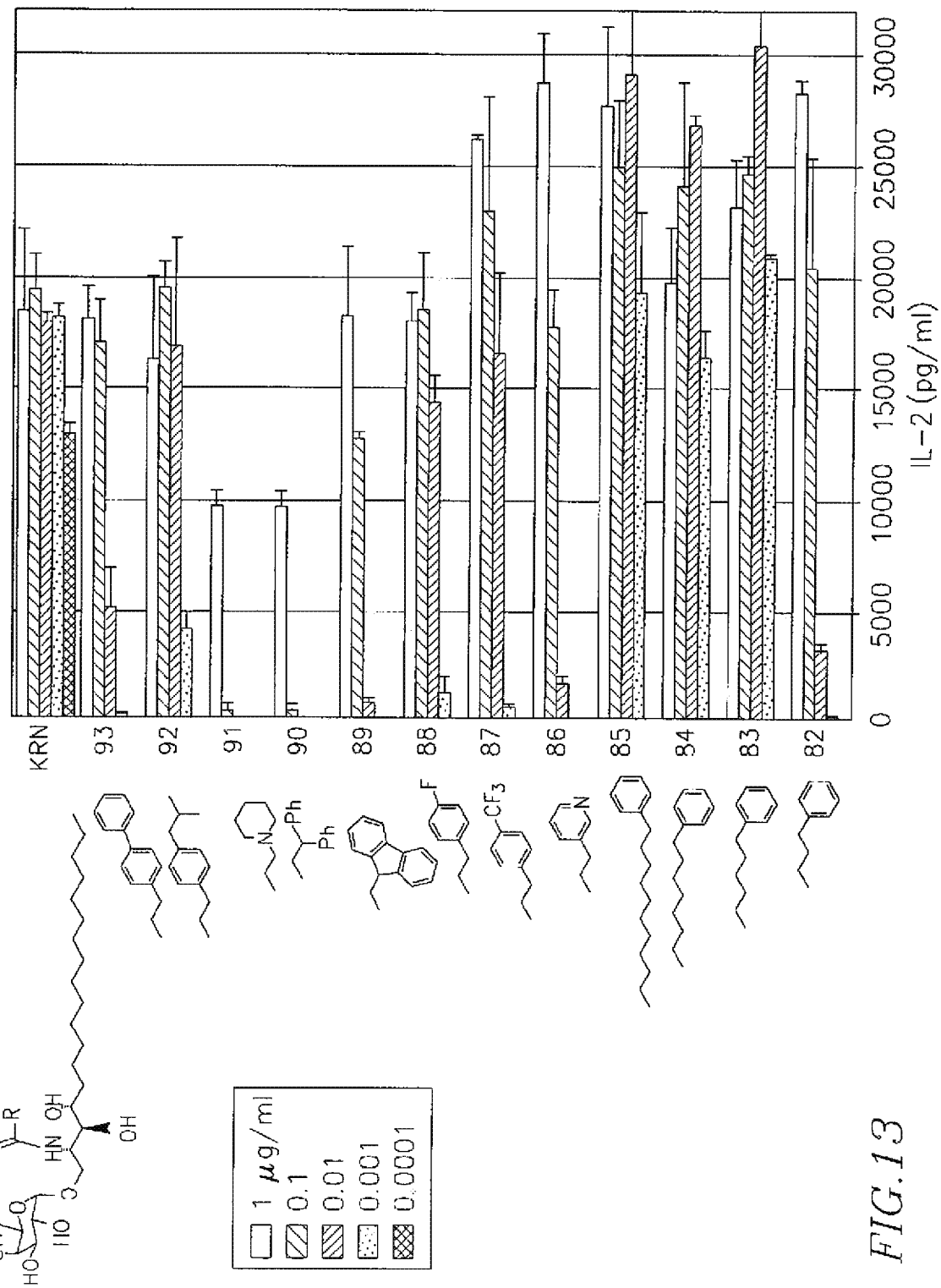
FIG. 13 demonstrates IL-2 secretion profiles obtained from murine NKT cells presented with other glycolipids as indicated, according to embodiments of the invention.

Another series of compounds were evaluated for their ability to stimulate IL-2 release, when provided at various concentrations (FIG. 13). In this case, several of these compounds stimulated greater IL-2 release, as compared to KRN7000 (α-GalCer), in particular, compounds with a terminal phenyl substituent.

The simplest benzoyl analog 58 showed only slight activity. Introduction of either electron donating groups (68; 4-OCH3, 69; 4-CH3) or withdrawing groups (70; 4-Cl, 59; 4-CF3) onto the benzene ring increased their activity. The other benzoyl analogues, 4-Pyridyl 80, 3-pyridyl 71, indole analog 81 and biphenyl analogues 72, 63 and 80 also exhibited similar trends. However, their activities still remained about half of α-GalCer.

Benzyl analogues 60, 61, 69, 73 and 74 showed improved IL-2 production compared with the benzoyl analogues. Of these compounds, smaller aromatic groups such as 60, 61 and 69 showed better activity than that of analogues 73, 74 bearing larger aromatic groups. The activities of thiophene analog 69 and benzene analog 60 were comparable.

Phenylethylene analogues 62, 77, 87 and 88 demonstrated comparable or even more potent IL-2 production compared with the benzyl analogues. The 4-CF3 analog 87 and 4-isobutyl analog 82 possessed slightly better activities compared with the 4-OCH3 analog 62 and 4-F analog 88. Substitution of the phenyl group with the 3-pyridyl group 86 diminished IL-2 production dramatically, which contradicted the trends of benzoyl analogues (58 and 71). In addition, the introduction of a trans-double bond as a spacer group significantly reduced IL-2 production compared with the saturated analog (75 and 77). The biphenyl analog 93 also showed a decreased activity. Introduction of a basic functional group, such as piperidinylethyl analog 91 demonstrated a significant reduction in cytokine production. This result may be because of repulsion between the basic amine moiety and the hydrophobic residue in the binding pocket. The 4-Fluorophenoxymethyl analog 65 gave a similar activity as the corresponding carbon analog 88. On the other hand, the 2,6-dimethyl substituted analog 66 exhibited a reduced activity, suggesting that the binding pocket was not large enough to accept bulky substituents. Similar results were observed in compounds 72, 89 and 90, bearing bulky substituent such as 4-biphenylmethyl, 2,2-diphenylmethyl and 9-fluorenyl, respectively.

Further extension of spacer chain length gave best results under these conditions. The activity of 3-phenylpropyl analog 82 was moderate. However, the 5-phenylpentyl 83, 7-phenylheptyl 84 and 10-phenyloctyl 85 all showed a significant increase of IL-2 production. Compounds 83-85 were much more potent than α-GalCer.

Example 9

Recognition of Glycolipids by Human NKT Cell Lines Results in NKT Cell IFN-γ and IL-4 Secretion Materials and Methods Generation of Vα24i Human NKT Cell Line Human NKT cell lines, expressing the Vα24i T cell receptor as well as CD161, were generated as follows: Anti-CD161 monoclonal antibodies, and anti-CD14 monoclonal antibodies, each coupled to magnetic beads (Miltenyi biotec, Auburn, Calif.), were used sequentially to isolate $CD161^+$ cells and $CD14^+$ cells from leukopaks. Immature dendritic cells were generated from the $CD14^+$ cells after a two-day incubation in the presence of 300 U/ml GM-CSF (R&D systems, Minneapolis, Minn.) and 100 U/ml IL-4 (R&D systems, Minneapolis, Minn.). Following irradiation with 2000 rads, the immature dendritic cells were co-cultured with syngeneic $CD161^+$ cells in the presence of 100-0.1 ng/ml of alpha-galactosylceramide and 10 IU/ml of IL-2 (Invitrogen, Carlsbad Calif.) for 10 to 14 days. After stimulating the $CD161^+$ cells a second time with alpha-galactosylceramide-pulsed, irradiated immature dendritic cells, NKT cell lines were shown by flow cytometry to express both $CD161^+$ and V 24i TCR (99% purity).

In some cases, Hela cells were transfected with a human CD1d construct [Xing et al. 2005. Bioorg Med Chem 13: 2907], and were used to present the glycolipids, via pulsing with the respective compounds at the indicated concentration, to NKT lines.

IFN-γ secretion by the Vα24i human NKT cell line was determined by ELISA (BD Pharmingen, San Diego, Calif.) after culture for 16 hours. For these assays, $1 \times 10^5$ Vα24i human NKT cells were co-cultured with $4 \times 10^5$ irradiated, immature $CD14^+$ dendritic cells, in the presence of the glycolipid compounds at 10 μg/ml in a 96-well flat-bottom plate.

Results

Figure 14:
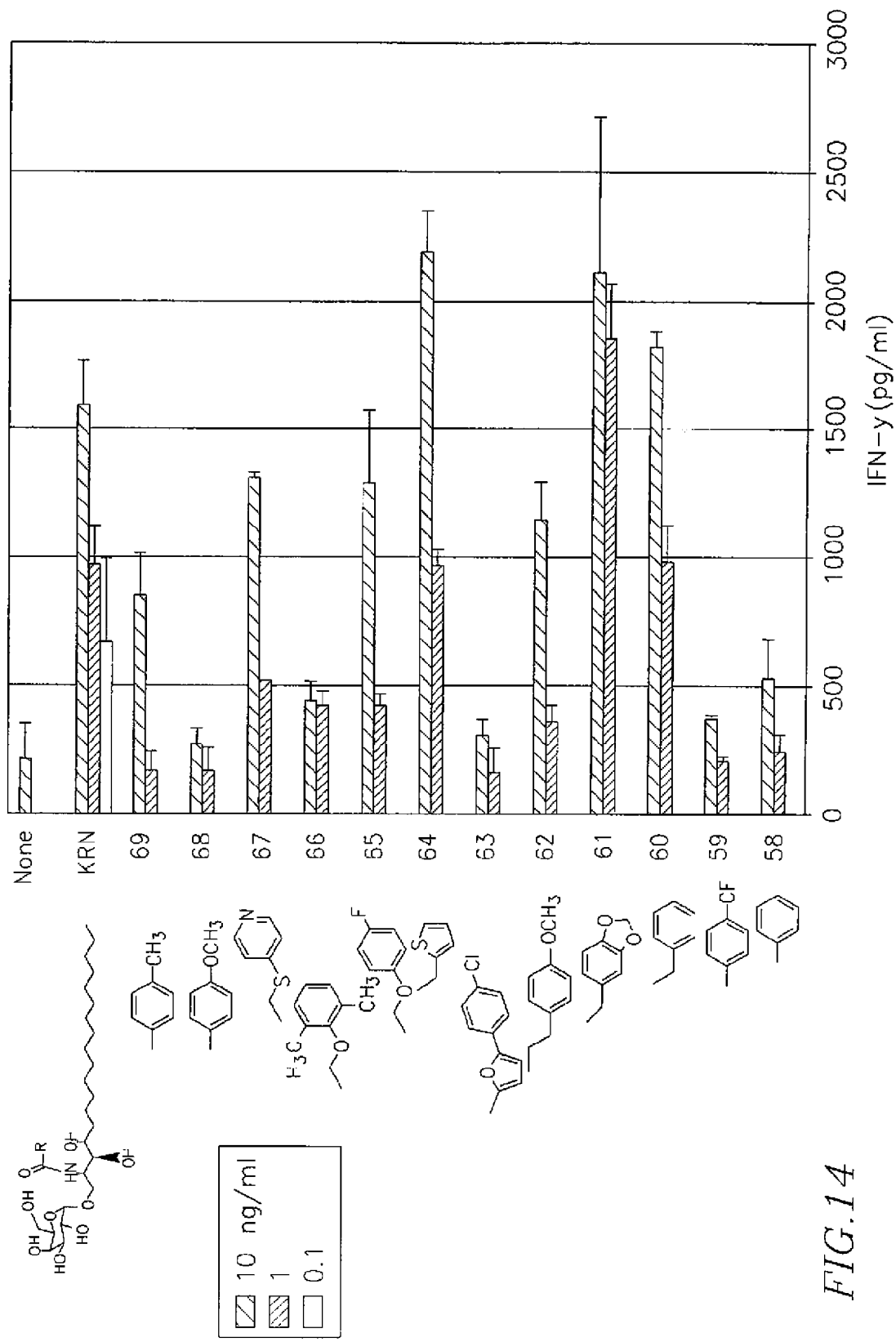
FIGS. 14, 15 and 16 demonstrate IFN-γ secretion from human NKT cells presented with the glycolipids as indicated, supplied at the indicated concentration.
Figure 15:
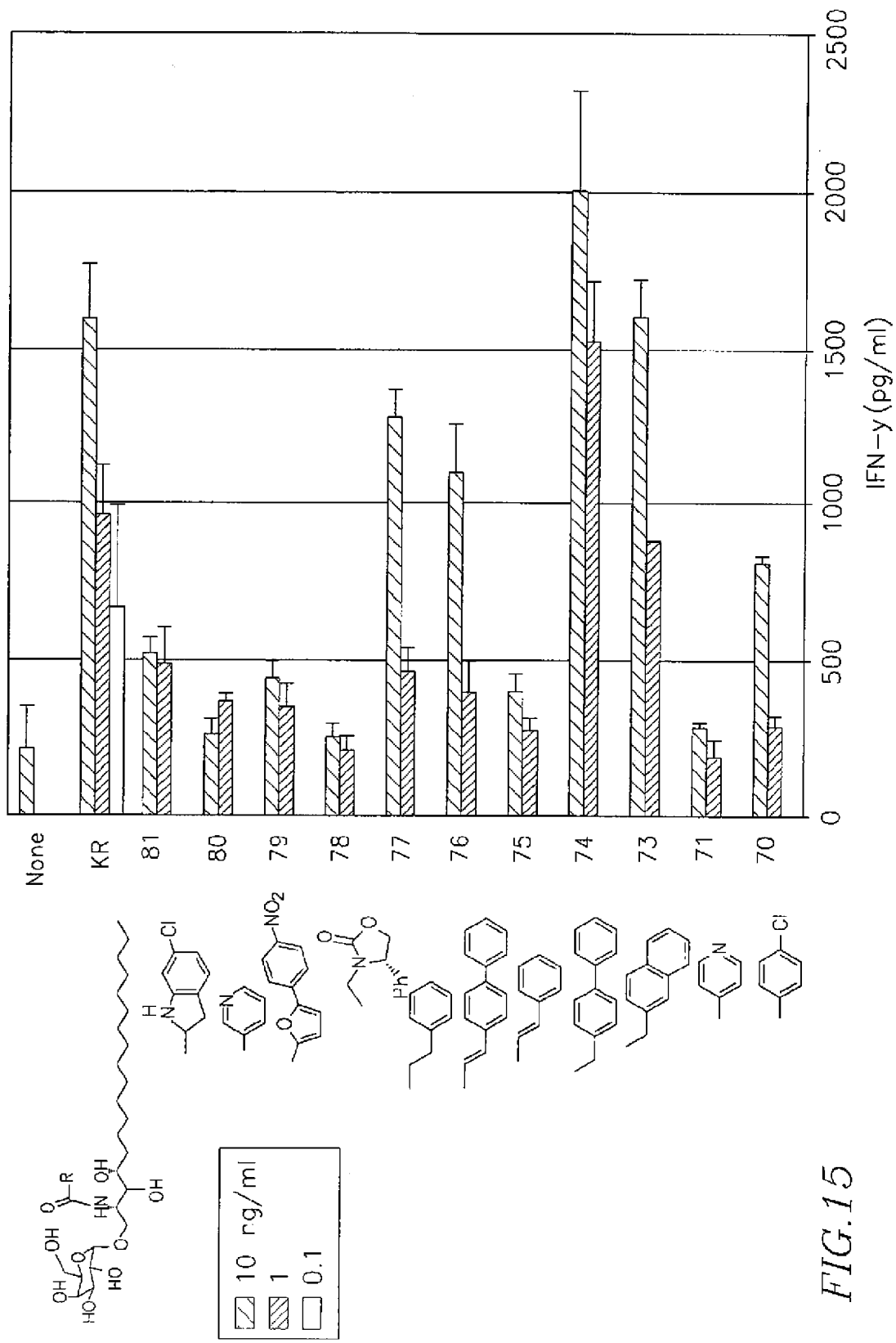
Figure 16:
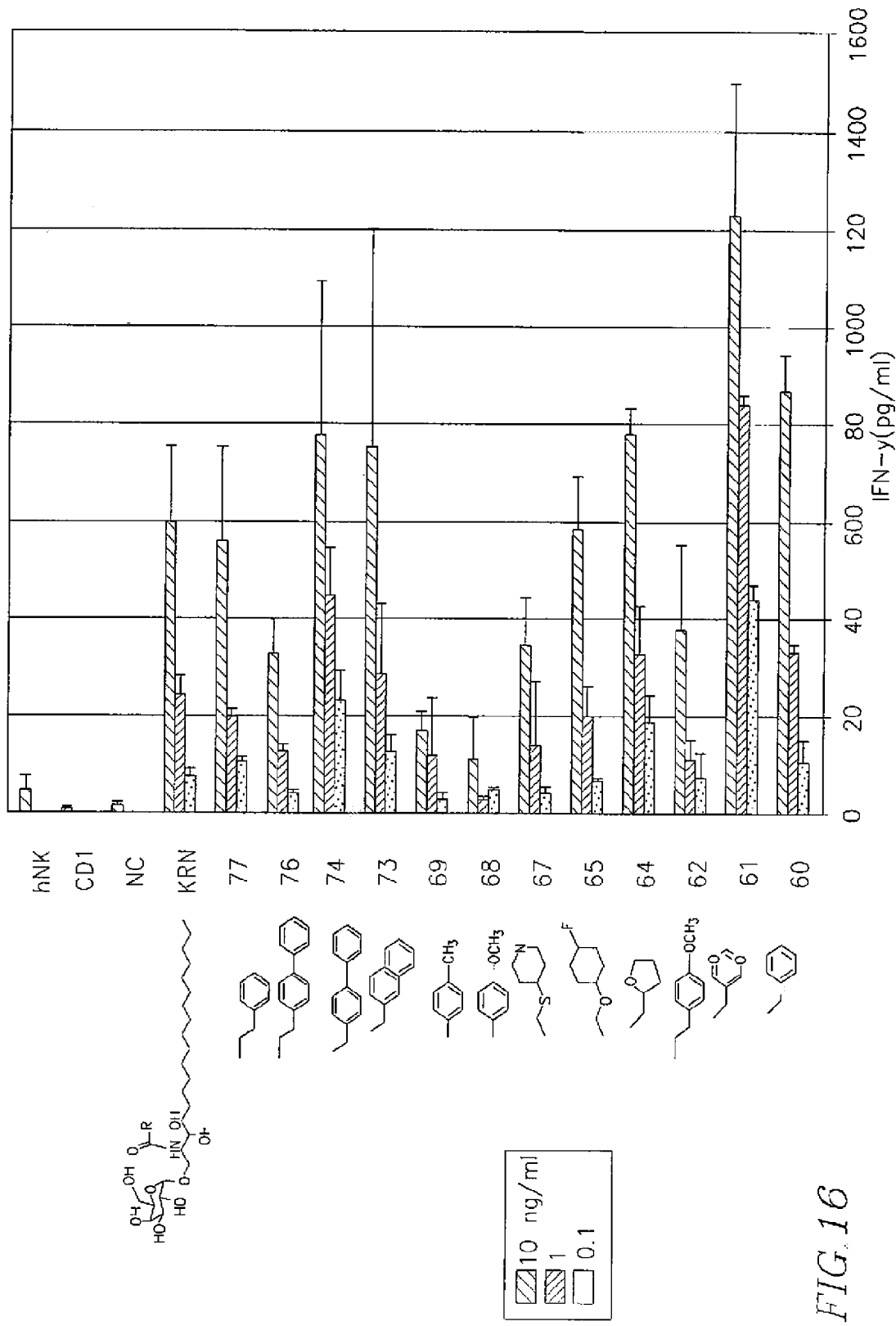

IFN-γ secretion from a Vα24i NKT cell line were assessed, after stimulation with irradiated, syngeneic $CD14^+$ immature dendritic cells in the presence of 10, 1 and 0.1 μg/ml of the respective glycolipids and 10 IU/ml of IL-2 (FIGS. 14, 15 and 16).

Stimulation of the NKT cell line by many of the glycolipid compounds resulted in significant IFN-γ secretion, when compared to the negative control, with some specific compounds providing greater greater IFN-γ secretion as compared to α-GalCer.

Figure 17:
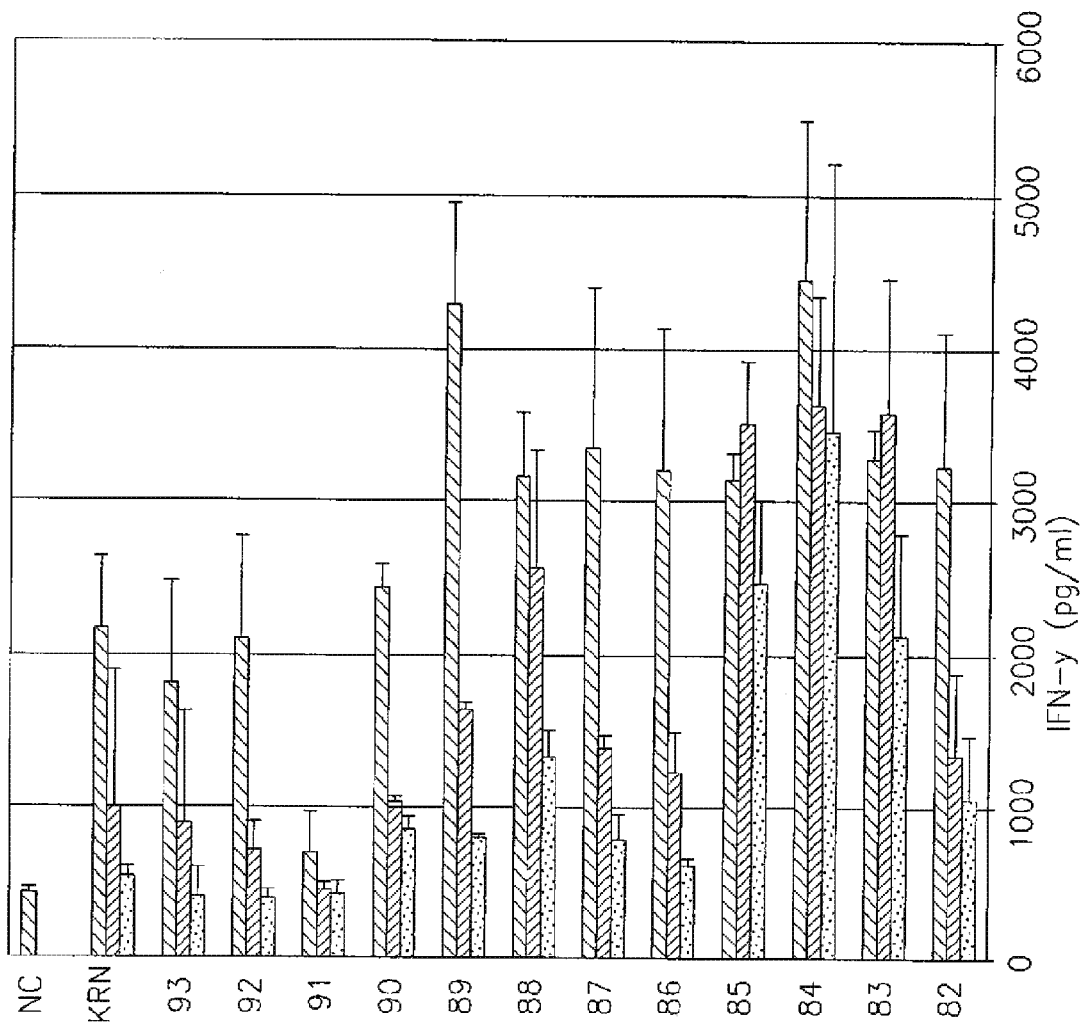
FIGS. 17 and 18 demonstrate IFN-γ secretion from human NKT cells presented with the glycolipids as indicated, supplied at higher concentration.
Figure 18:
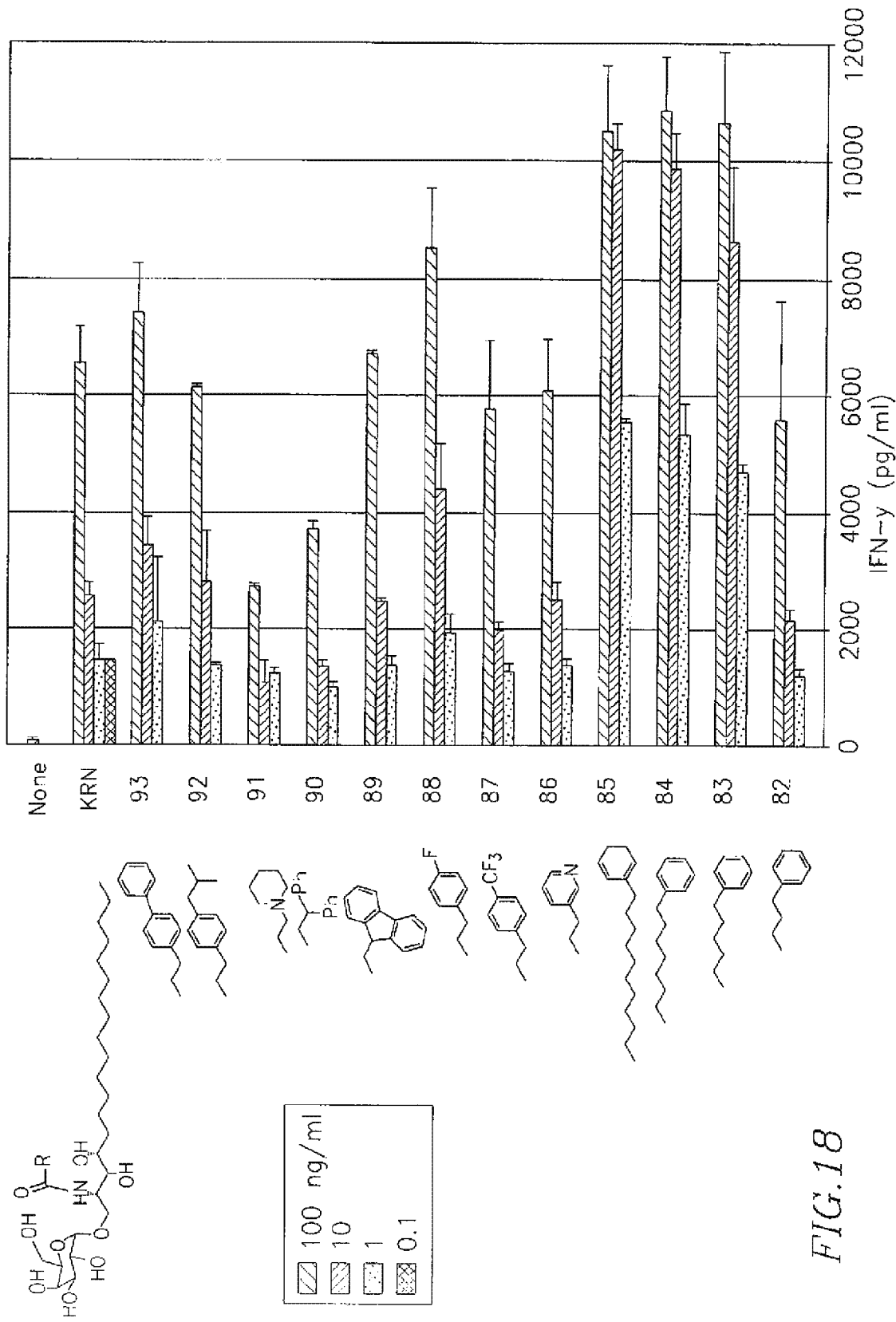

As illustrated in FIGS. 17 and 18, additional glycolipid compounds were prepared and evaluated for interferon-γ secretion by human NKT cells in response to glycolipid presentation by $CD14^+$ DCs, as compared to α-GalCer, at a concentration of 100-0.1 ng/mL. Compounds 83, 84 and 85 in these figures consistently stimulating greater IFN-γ secretion, at all doses evaluated, as compared to KRN, and other compounds.

Figure 19A:
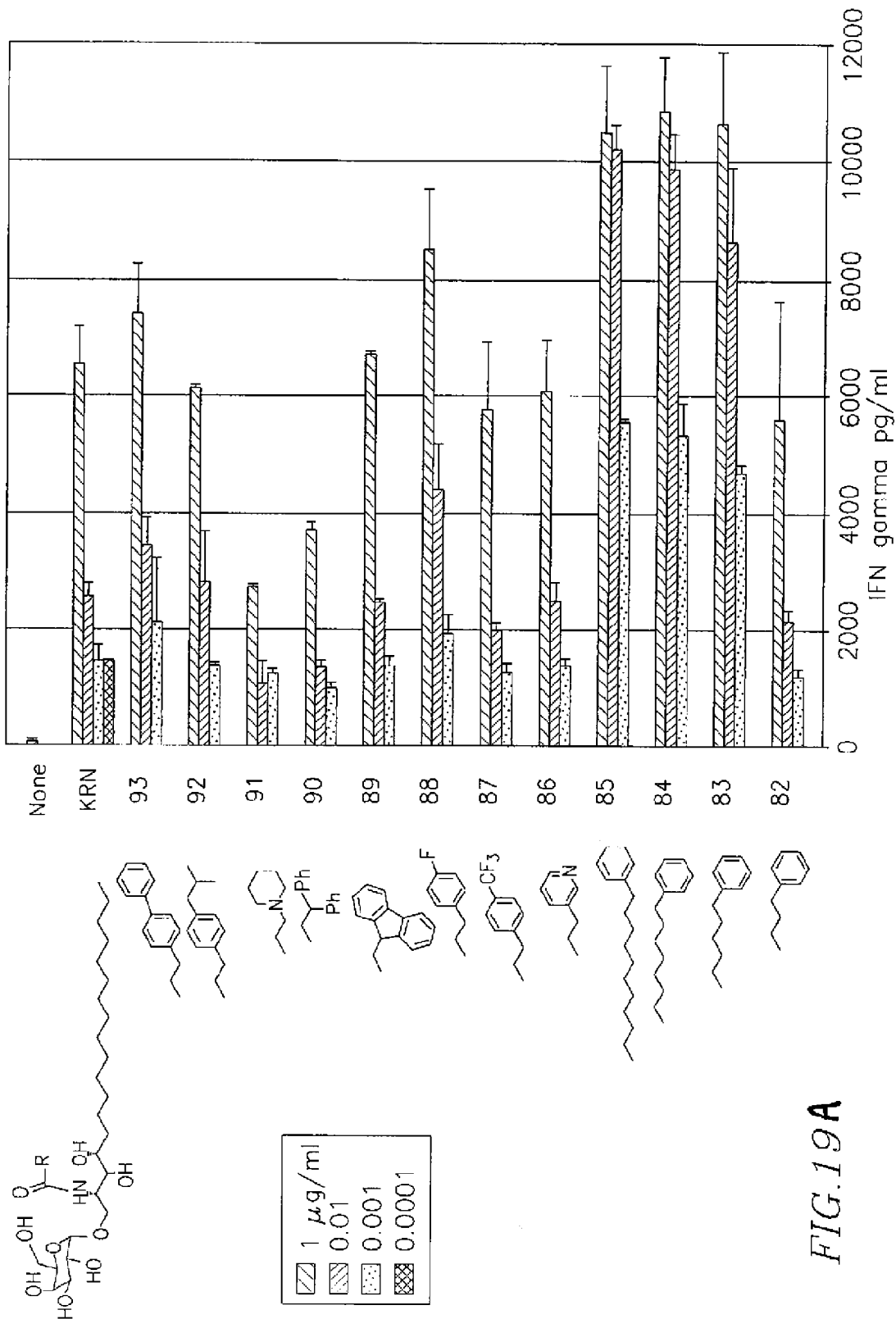
FIGS. 19A-C demonstrate similar IFN-γ secretion from human NKT cells presented with the glycolipids, at the indicated concentration, in the context of Hela cells transfected with CD1d.
Figure 19B:
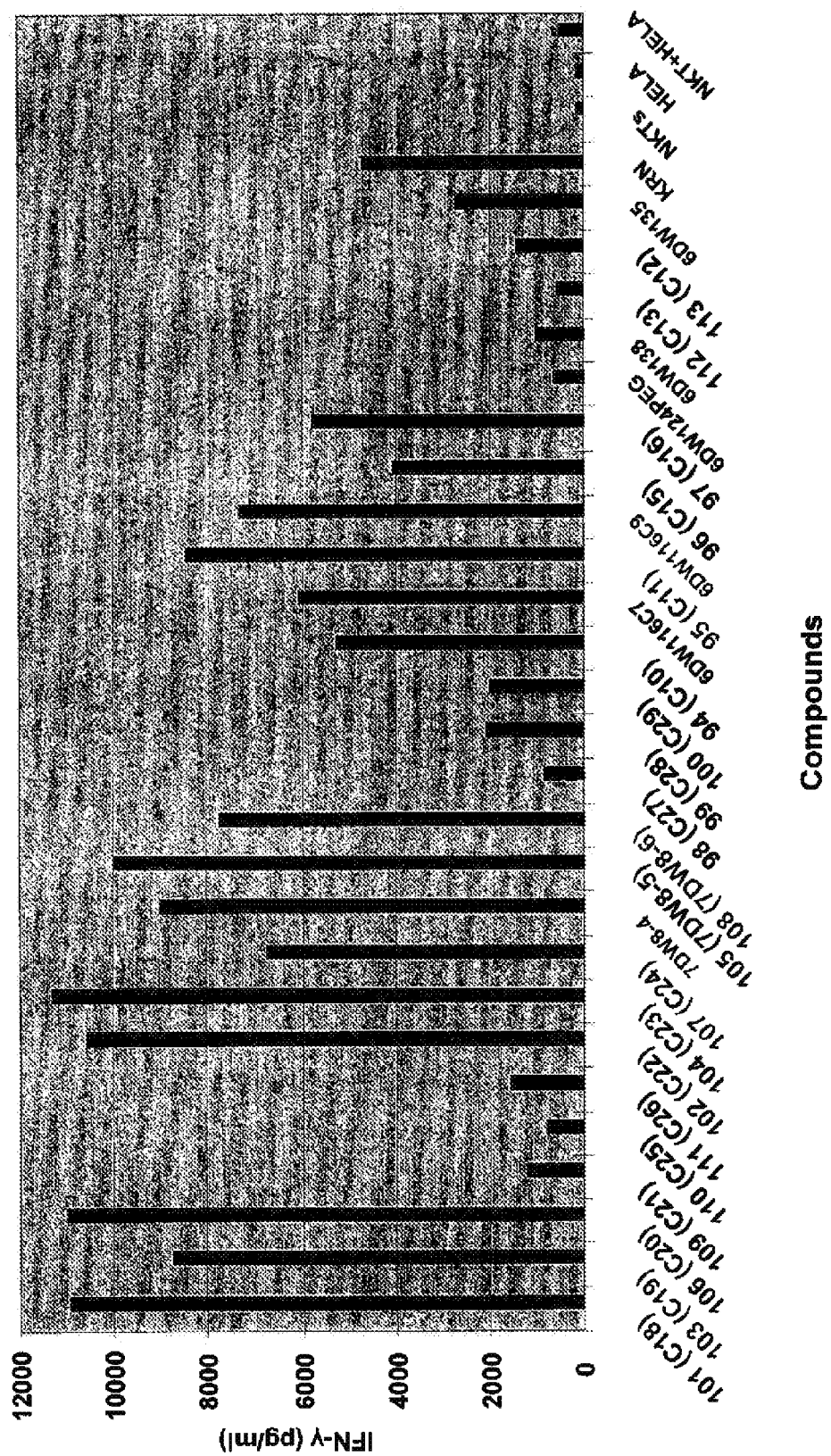
Figure 19C:
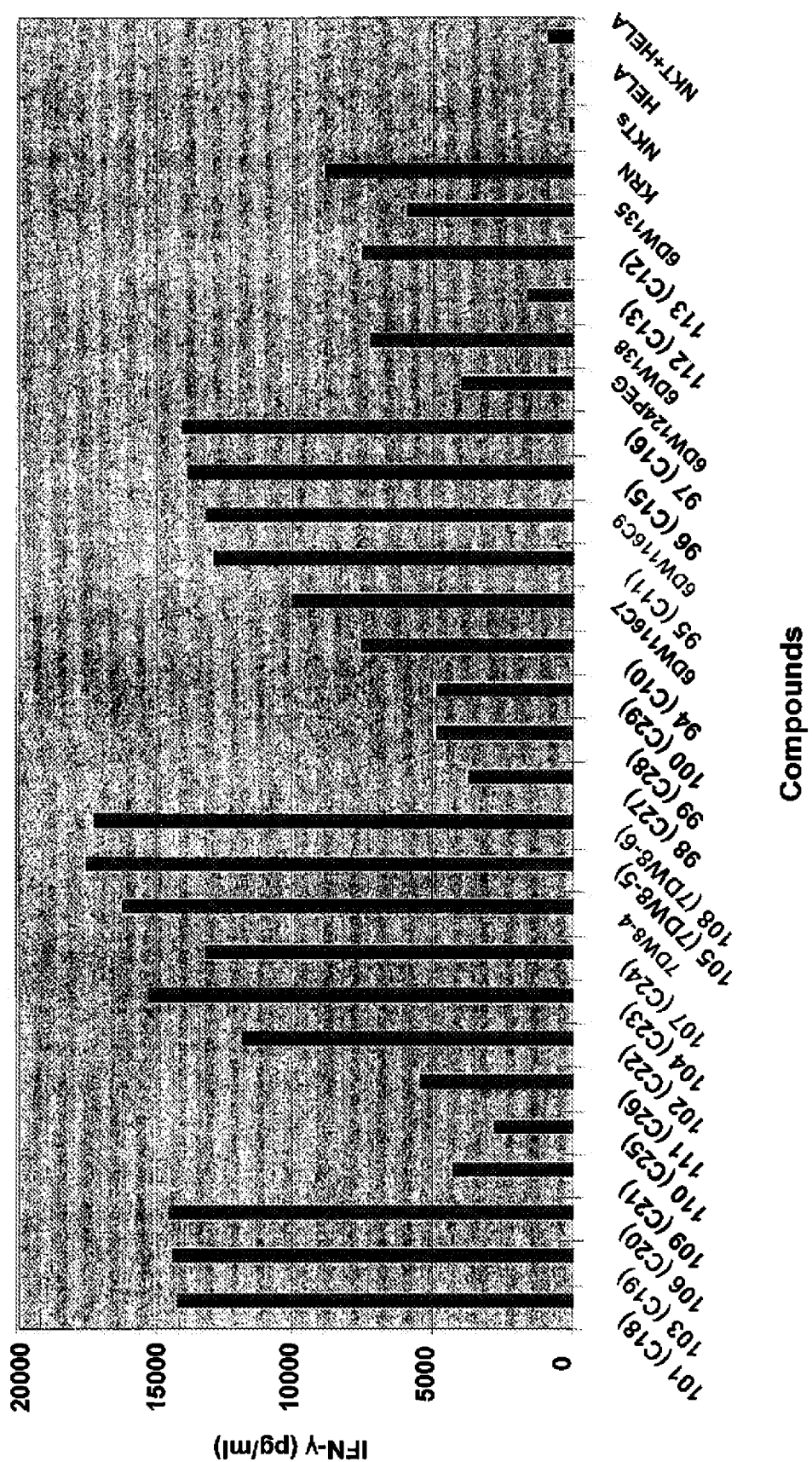

Hela cells expressing human CD1d were also effective in presenting the glycolipids to human NKT cells, with similar profiles in terms of stimulating NKT cell IFN-γ secretion (FIG. 19).

Figure 20A:
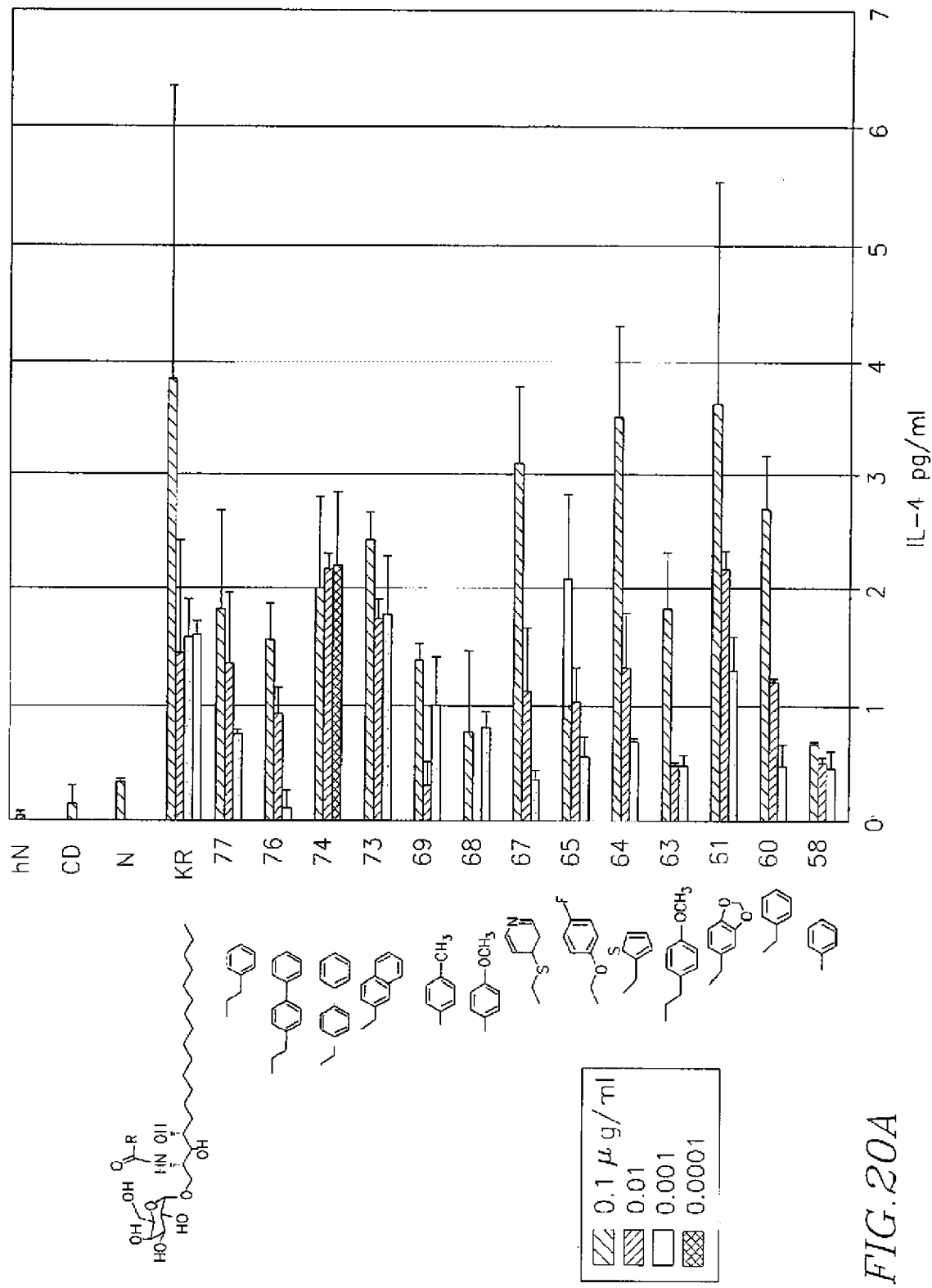
FIG. 20 demonstrates IL-4 secretion from human NKT cells presented with the glycolipids, at the indicated concentration in the context of dendritic cells (A) or transfected Hela cells (B).
Figure 20B:
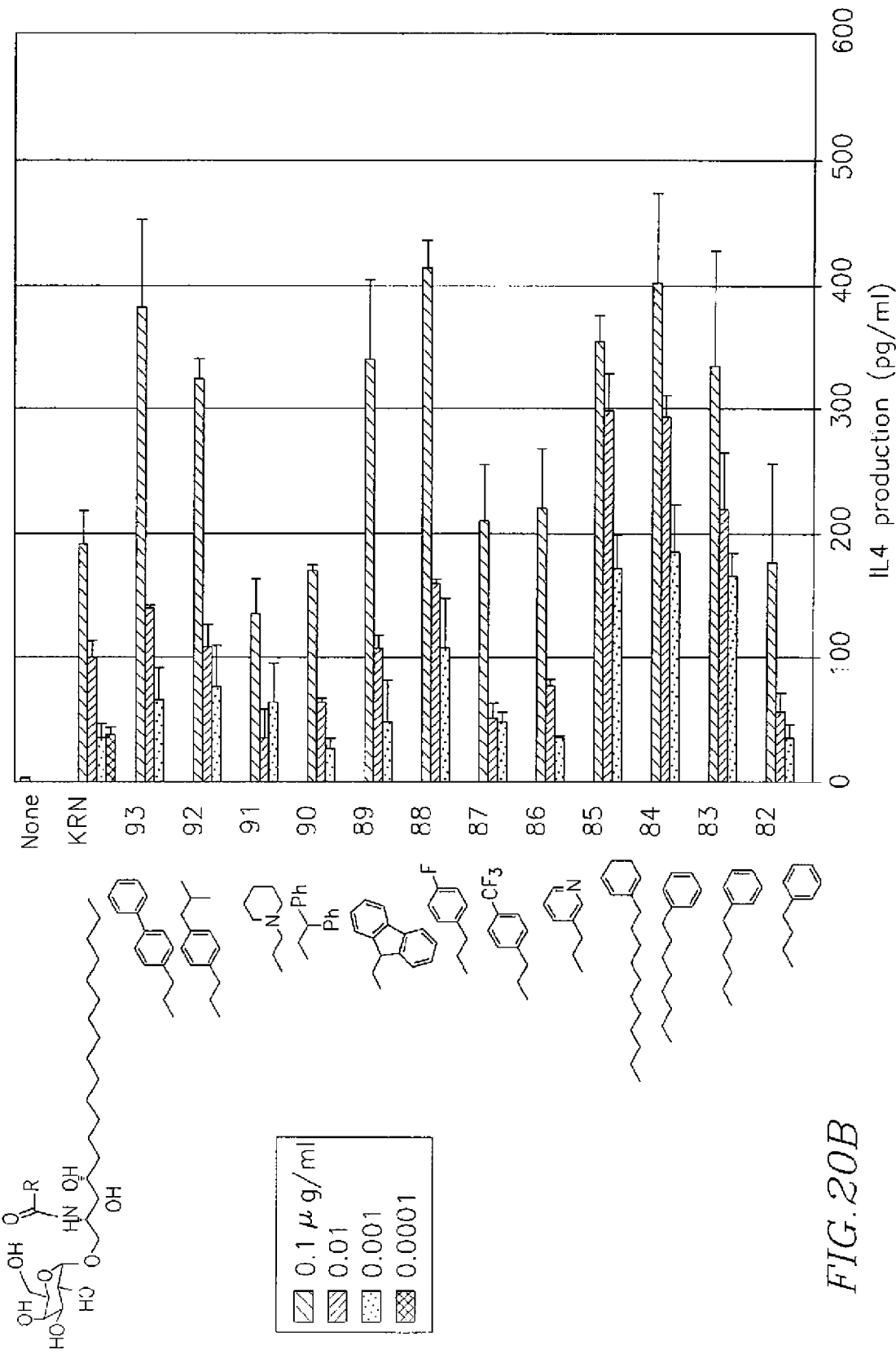
Figure 21A:
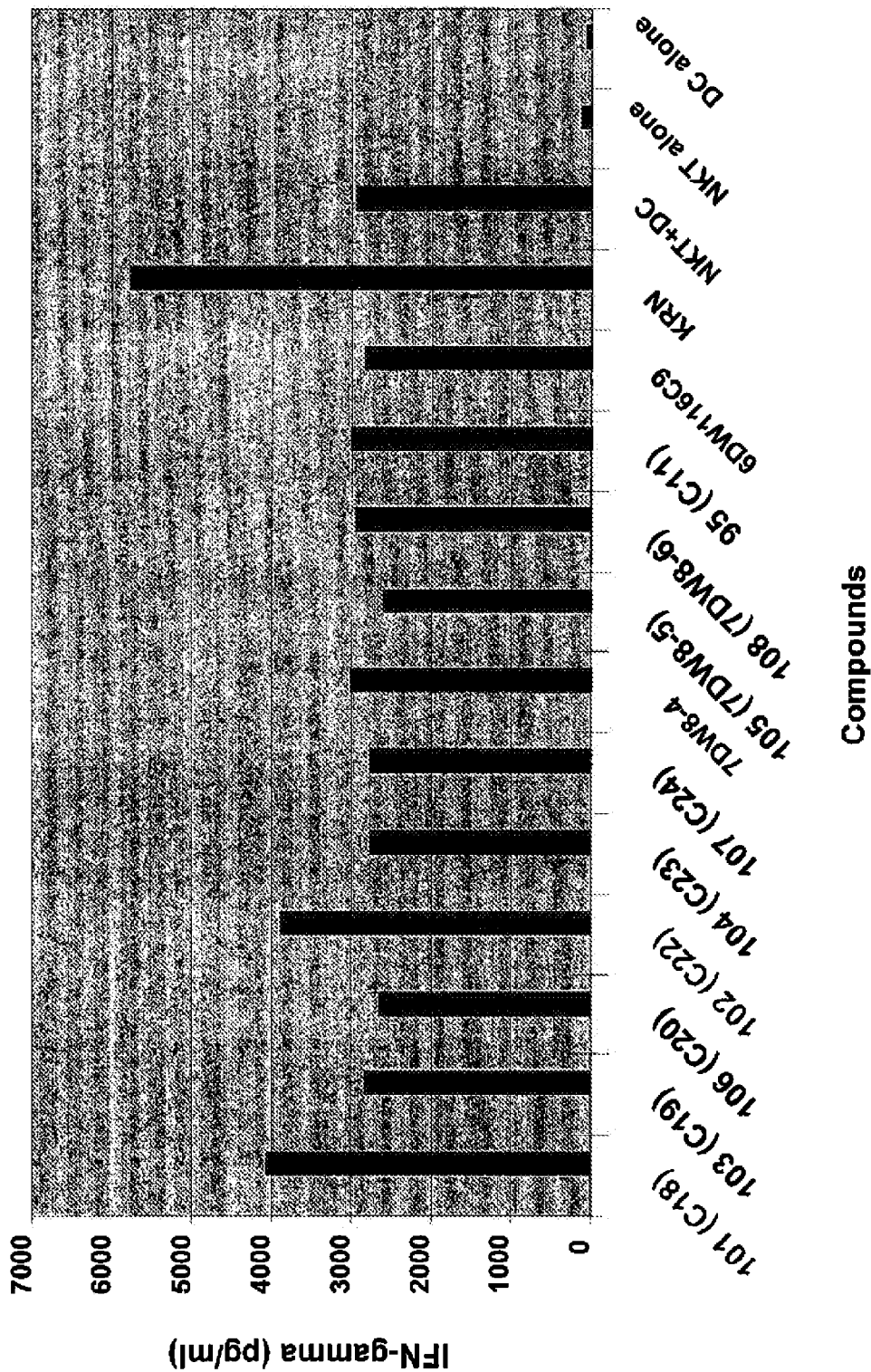
FIG. 21 demonstrates multi-cytokine secretion from human NKT cells presented with the glycolipids, at the indicated concentration in the context of dendritic cells: (A)/(B) 1010A and 1010B NKT cells—IFN-γ; (C)/(D) 1010A and 1010B NKT cells—IL-12; (E)/(F) 1010A and 1010B NKT cells—GMCSF.
Figure 21B:
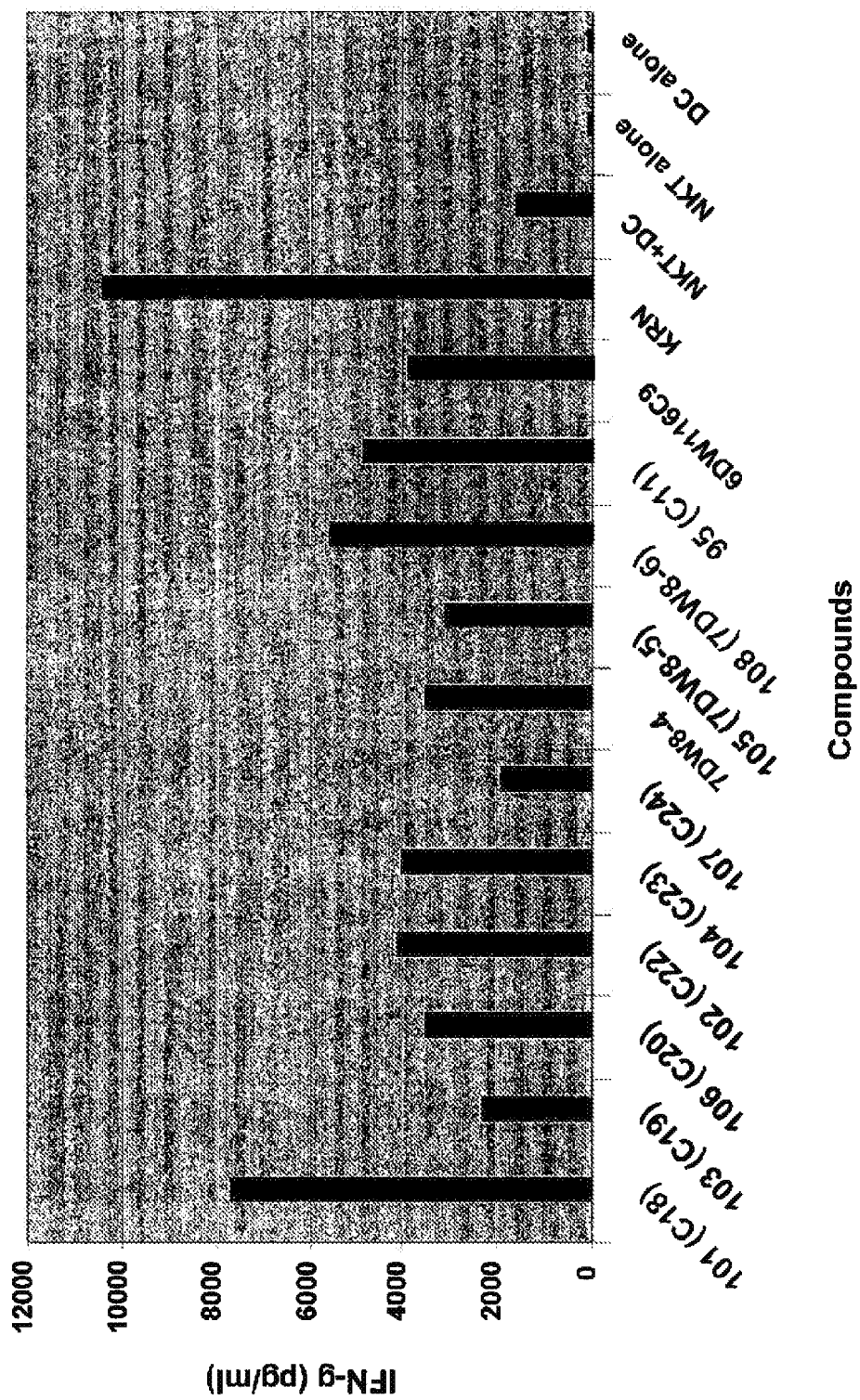
Figure 21C:
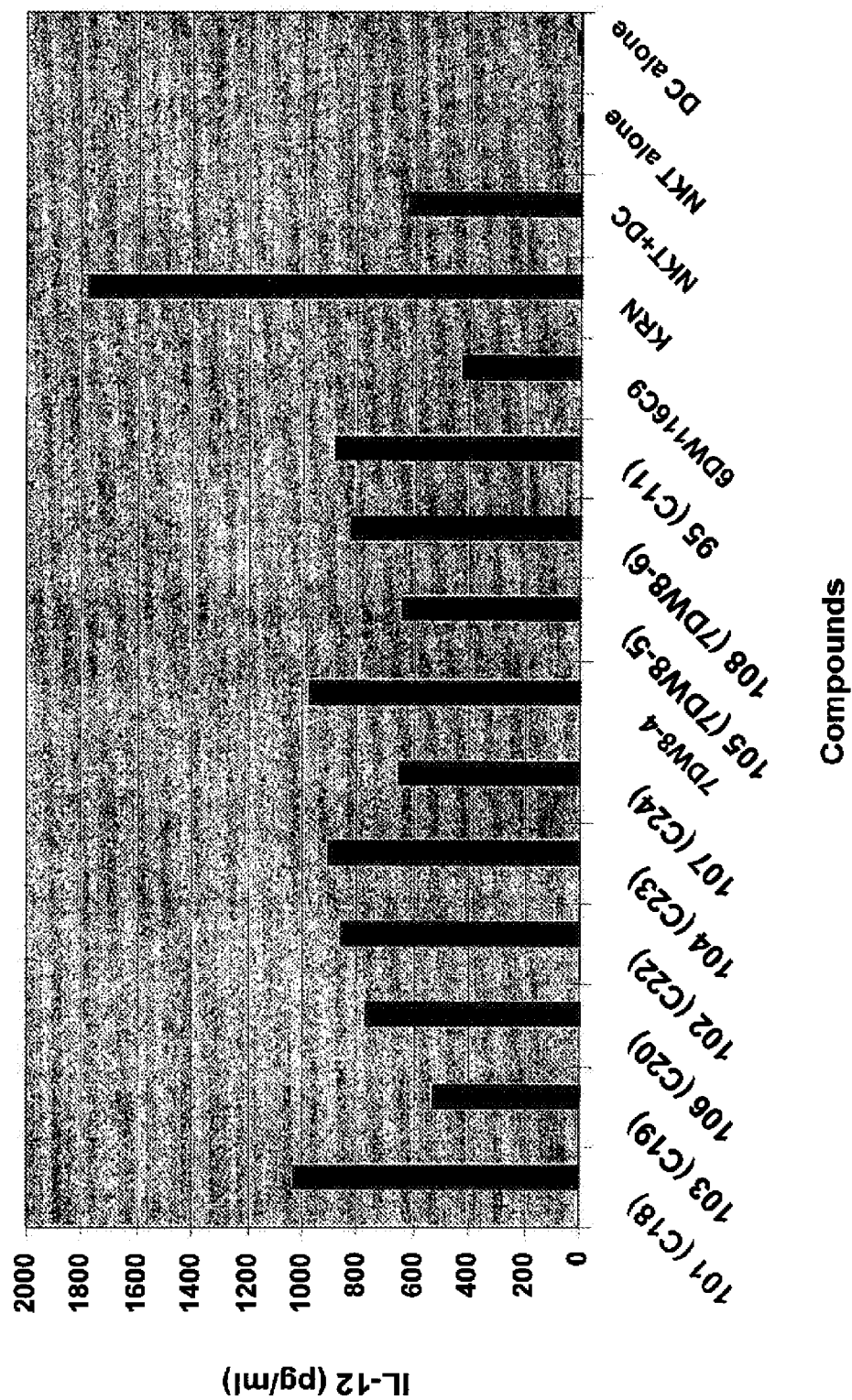
Figure 21E:
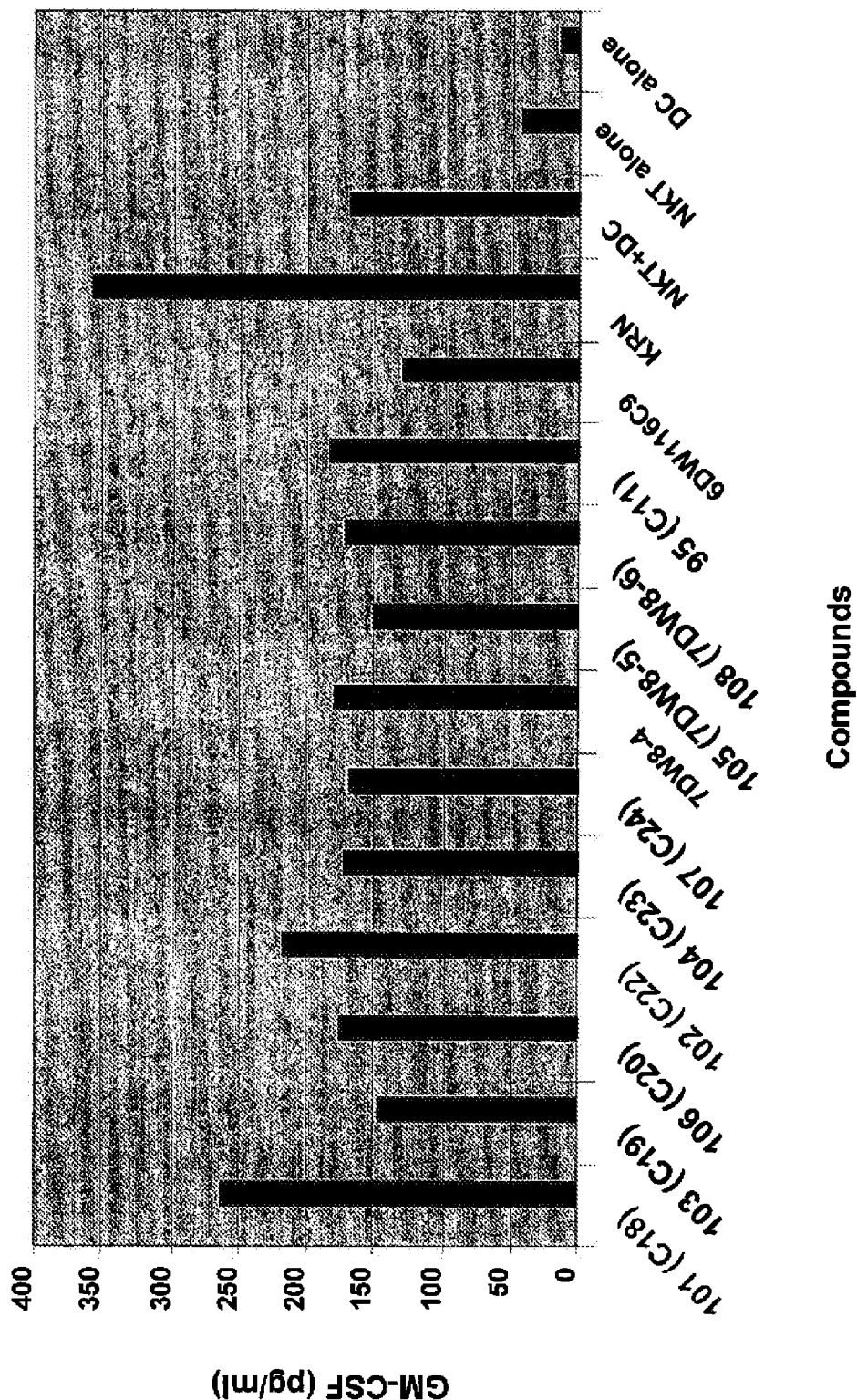
Figure 21F:
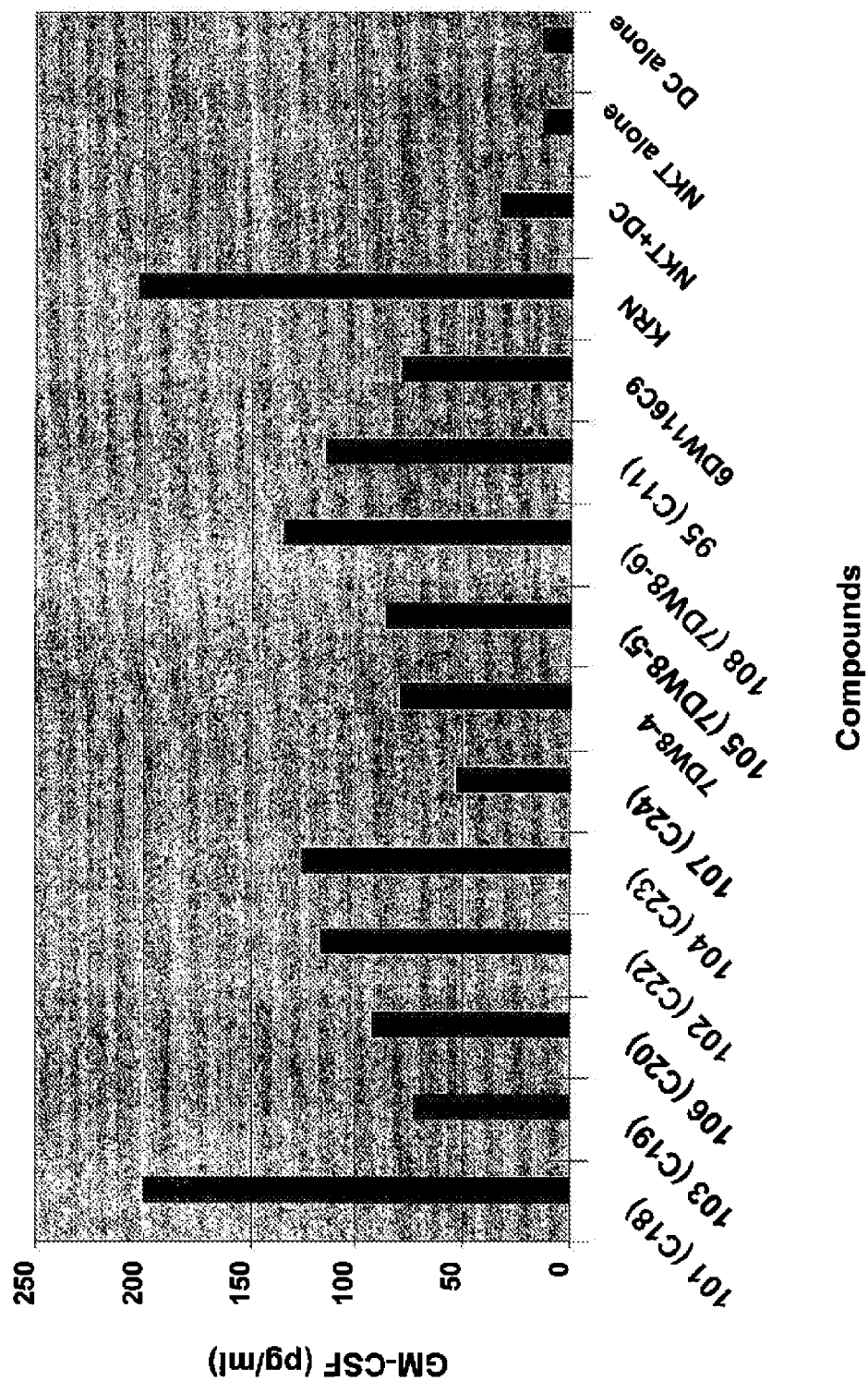

Compounds effective in stimulating IFN-g secretion were also found to stimulate IL-4 secretion (FIG. 20).

The longer alkyl chain analogues 83-85 were more potent toward both IFN-γ and IL-4 production than the shorter alkyl chain analogues. The 7-phenylheptyl analog 83 exhibited a high ratio of IFN-γ/IL-4 activity and was the best among these compounds. However, compounds 73 and 77 are more selective for IL-4 production while 82 is specific for IFN-γ production.

Example 10

Possible Structural Basis for Glycolipid Recognition

Recent glycolipid-CD1d protein crystal structures revealed the existence of various aromatic residues, Tyr73, Phe114, Phe70 and Trp114, which might be able to interact with the phenyl group of the present compounds comprising fatty acyl chain analogues. According to these crystal structures, the benzoyl analogues 8-14, which have no spacer chain, seemed to be too short to interact with these aromatic residues. To further investigate the interactions between the phenyl analogues and human CD1d, Autodock 3.0 [G. M. Morris, et al., J. Comp. Chem., 1998, 19, 1639-1662] was utilized to model the binding of these compounds in the hCD1d hydrophobic groove (FIG. 21). Compounds 40-42 were individually docked and their results did not vary significantly from the crystal structure of α-GalCer bound to hCD1d [M. Koch, et al., Nat. Immunol., 2005, 6, 819-826]. In each case, the phytosphingosine tail extended into the F' pocket and the A' pocket was occupied by the fatty acyl chain with the galactose headgroup presented in nearly all the same configuration. However, introduction of a terminal phenyl group in the α-GalCer analogues seemed to promote additional specific interactions between compounds 40, 41 and the phenol ring of Tyr73 and between 42 and Trp40.

Biphenyl analogues 16-18 and cinnamoyl analogues 30, 32, lacked a flexible fatty acyl chain and may not have been able to extend into the A' pocket deep enough to make any specific interactions. Extension of the spacer chain length, such as the benzyl analogues 19-22, the phenylethylene analogues 24-28, and the 4-fluorophenoxymethyl analog 34, allowed for tighter binding via π-π interaction, possibly with the aromatic side-chain of Tyr73. Further extension of the spacer chain length, such as pentamethylene analog 83, heptamethylene analog 84 and decamethylene analog 85, were more suitable for tighter binding. These results suggest that the introduction of π-π interaction potentiates IL-2 production, probably through the formation of a tighter ligand—CD1d protein complex.

These fatty acyl chain analogues bearing aromatic groups seemed to possess more potent activity than the corresponding simple fatty acyl chain analogues. Compounds 83-85 bearing 5, 7, 10 carbons spacer chain, respectively, demonstrated much more potent IL-2 production than that of other groups, with α-GalCer bearing a C26 fatty acyl chain. These results suggest that introduction of a terminal aromatic group on the fatty acyl chain causes an enhancement of the activity through interactions between the aromatic residues in the hydrophobic pocket of CD1d protein and the lipid tail.

Example 11

In Vivo Mouse Assay

Figure 22B:
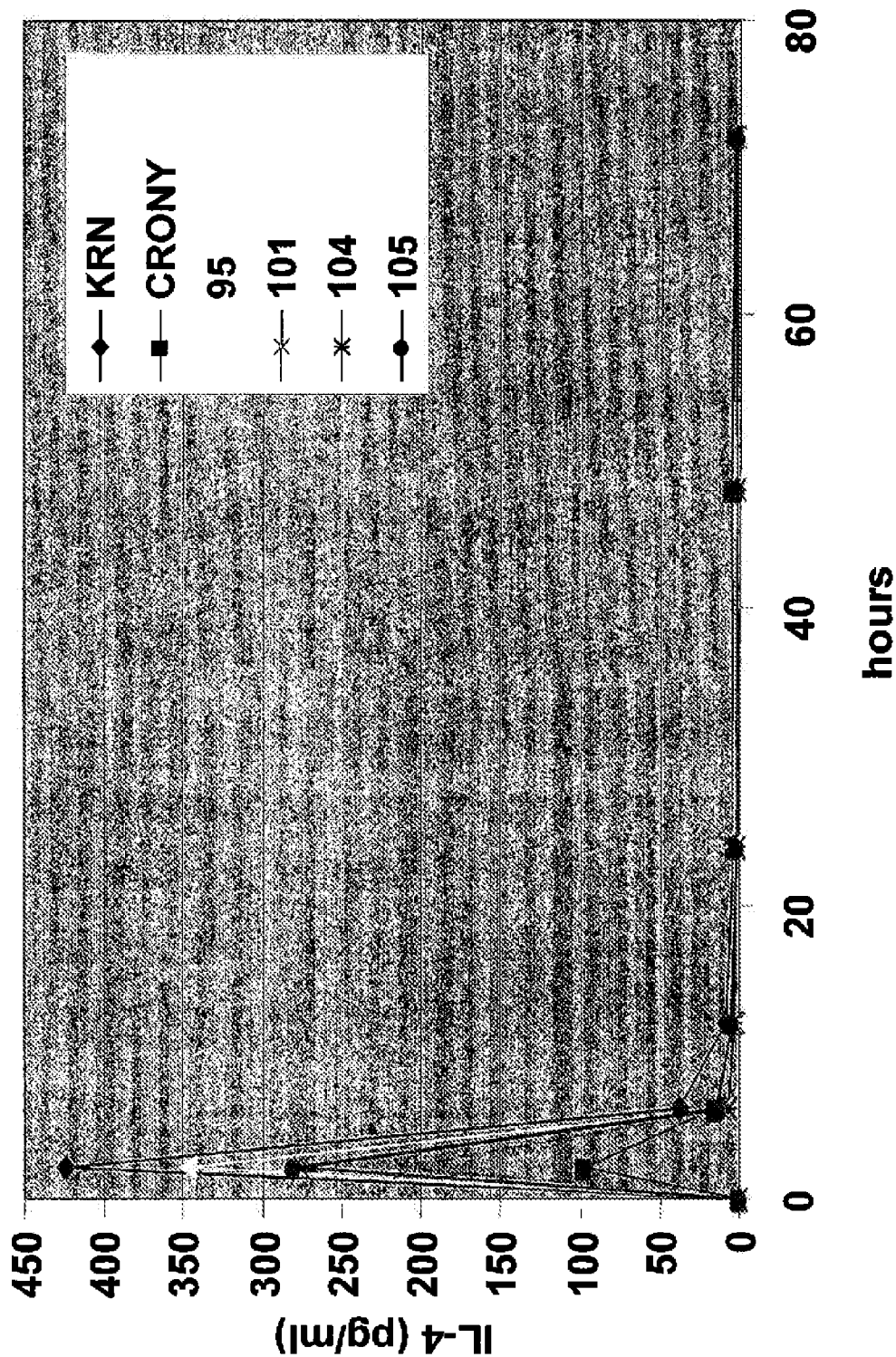
FIG. 22 demonstrates in vivo secretion from B6 mice presented with indicated glycolipids: (A) IFN-γ; (B) IL-4; (C) IL-12.
Figure 22C:
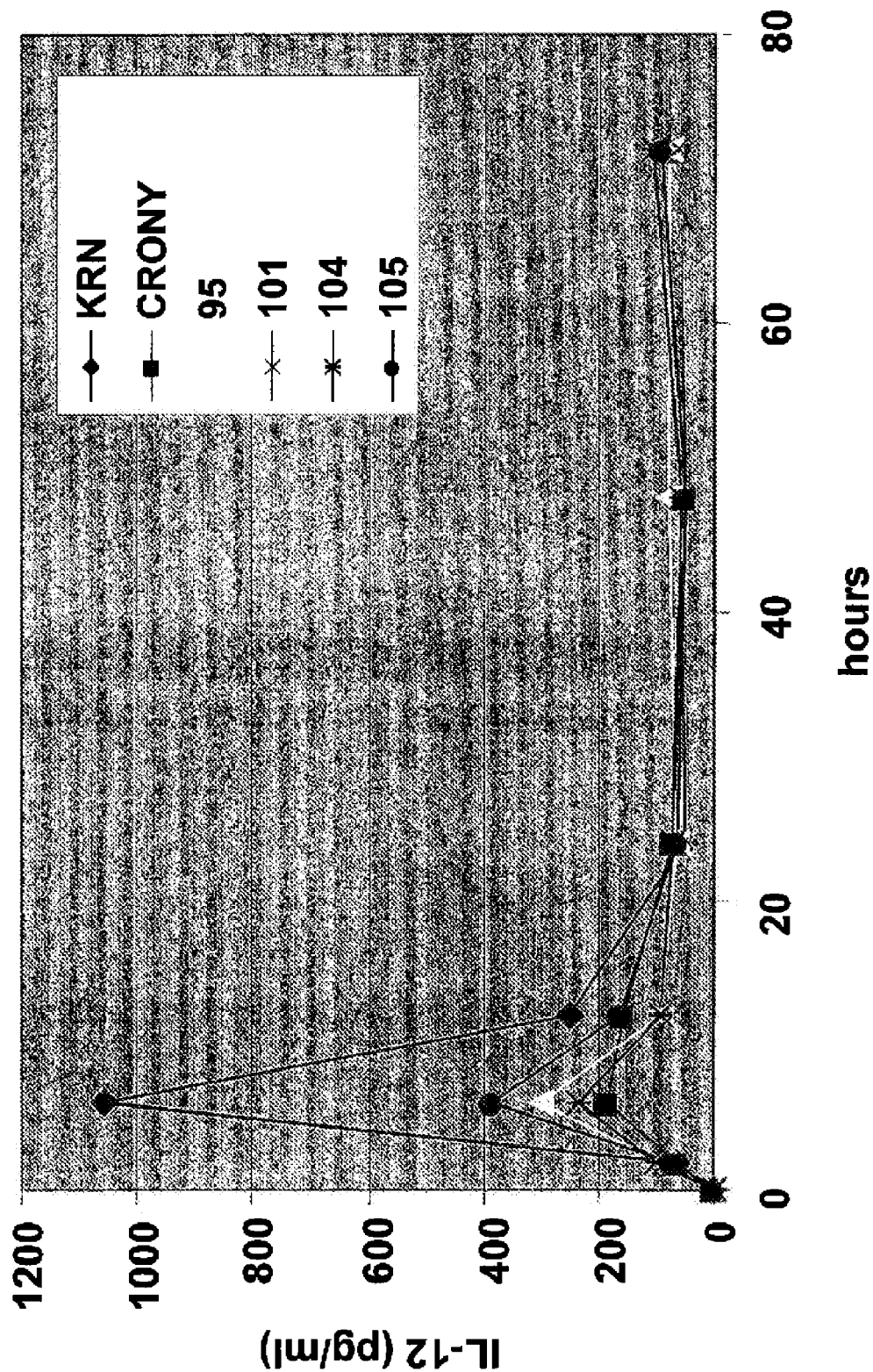
Figure 23:
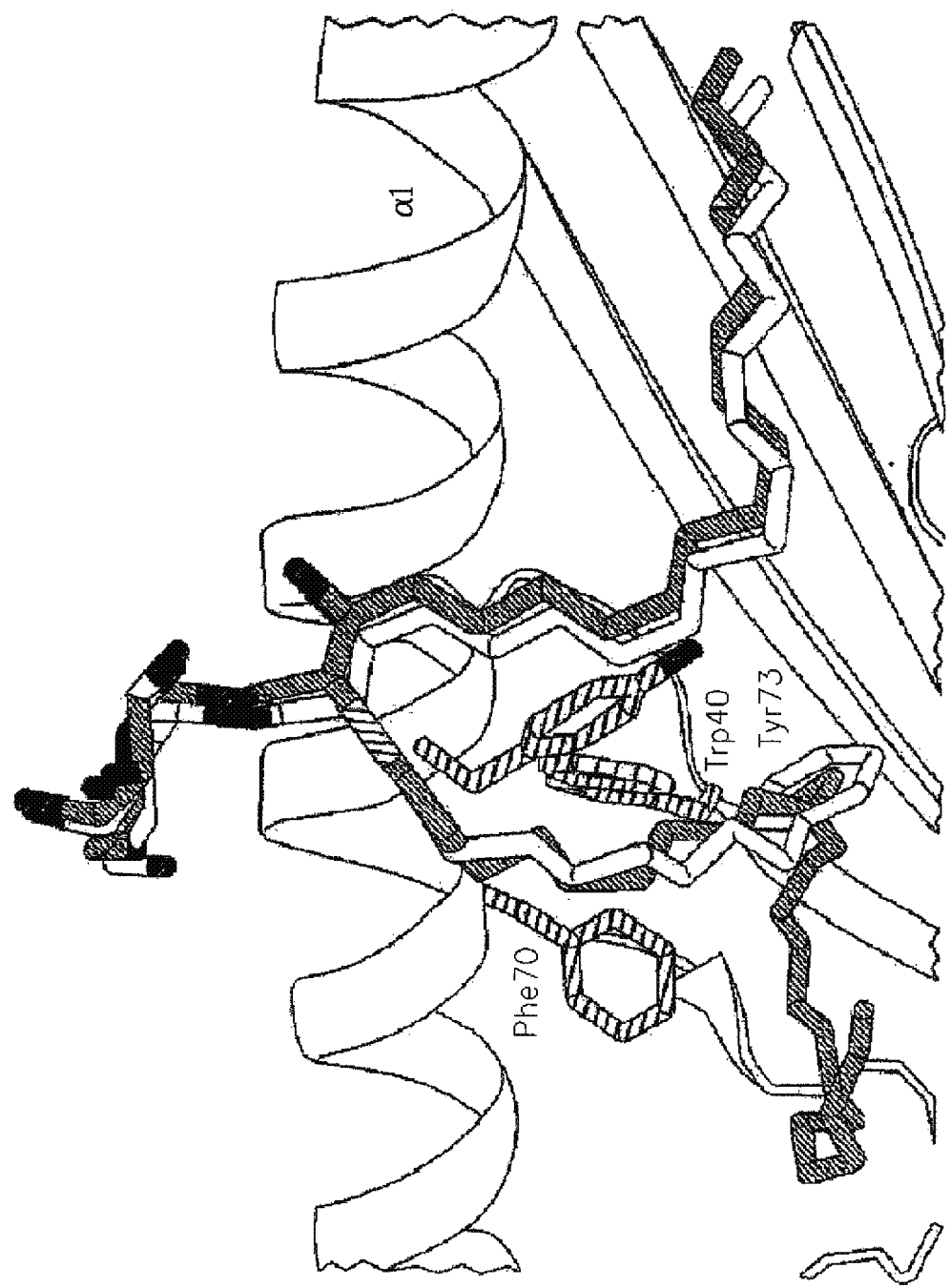
FIG. 23(A) depicts the superimposition of docking results of compound 84 from Example 10 (yellow) with the crystal structure of α-GalCer (green)/hCD1d complex. The α2 helix is removed for clarity. The overall binding motif of the docked compound did not notably deviate from the crystallized structure. The terminal phenyl group 84 is within distance to interact with the aromatic ring of Tyr73; (B) depicts the hCD1d docking model of analogue compounds 83-85.
Figure 23B:
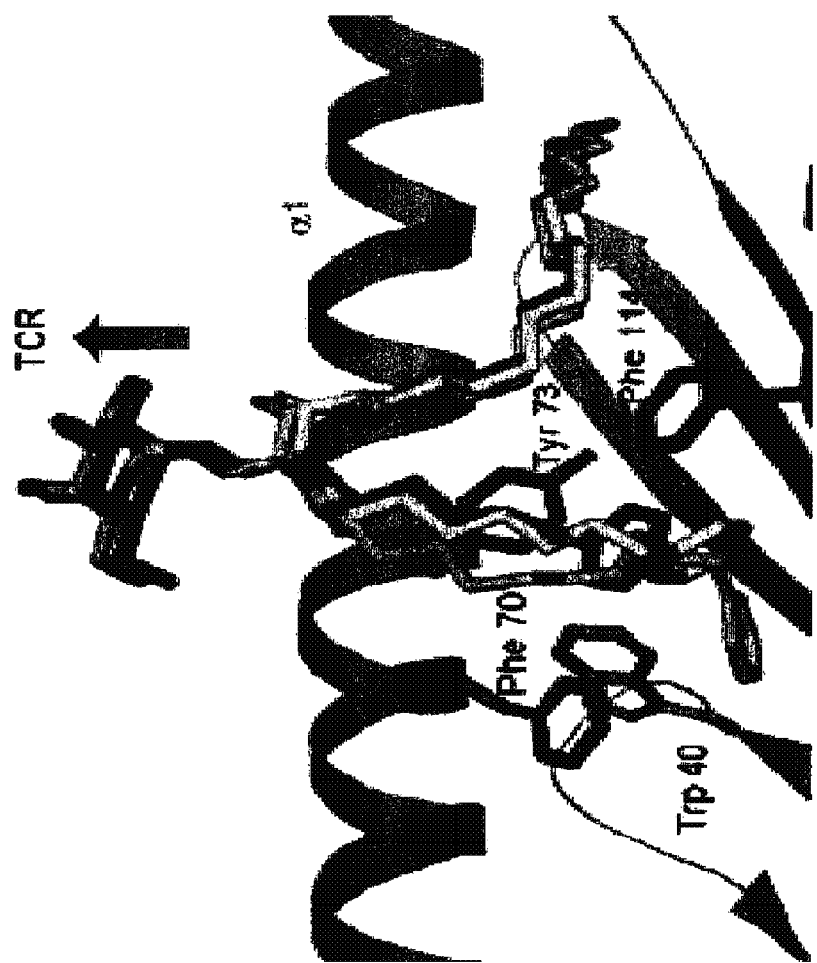
Figure 23B:
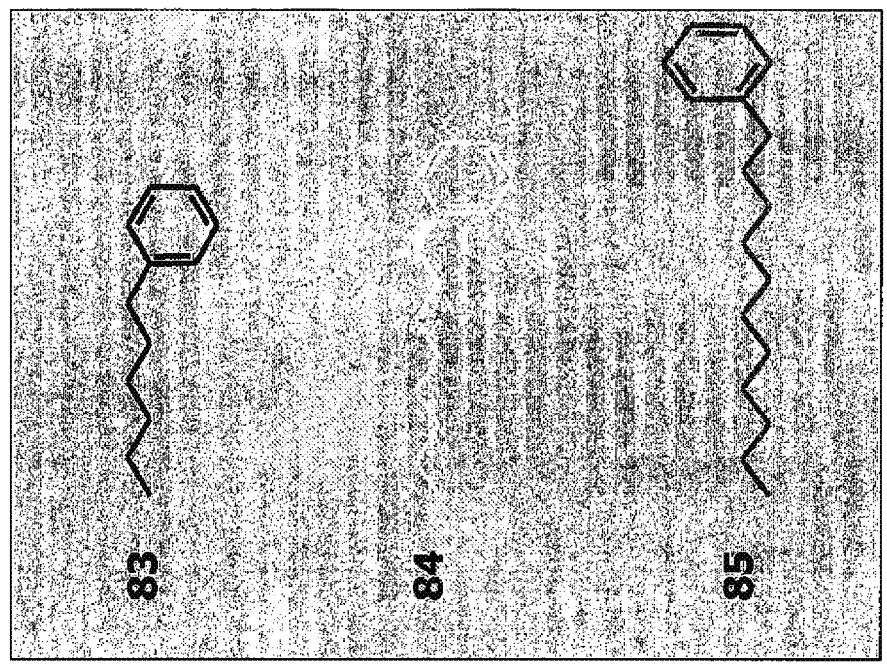

Wild-type C57BL/6 (B6) mice were administered intravenously with 1 μg of each glycolipid or with nothing, and serum samples were obtained at 2, 6, 12, 24, 48, and 72 hours after injection for ELISA analyses of IL-4, IFN-γ, and IL-12 concentrations. The serum concentrations of IFN-γ and IL-4 were measured by way of a sandwich ELISA (e-bioscience, San Diego, Calif.). The serum concentrations of IL-12p70 were also measured by way of a sandwich ELISA (PharMingen, San Diego, Calif.). Results are provided in FIG. 22.

It will be appreciated by a person skilled in the art that the present invention is not limited by what has been particularly shown and described hereinabove. Rather, the scope of the invention is defined by the claims that follow:

We claim:

1. A method for enhancing immunogenicity of a compound, composition, or vaccine in a subject, the method comprising steps: (a) administering to the subject a compound, composition, or vaccine designed to stimulate a protective immune response, wherein the compound, composition, or vaccine, comprises an adjuvant, wherein the adjuvant comprises a compound represented by the structure of formula 1:

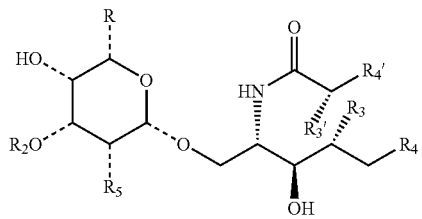

(1)

wherein, $R=COOR_1$ or $CH_2OR_1$;
$R_1$=H or an alkyl group;
$R_2$=H or $SO_3^-$;
$R_3$=H or OH;
$R_3'$=H or OH;
$R_4$ and $R_4'$ are independently chosen from
(a) H,
(b) alkyl;
(c) alkenyl; and
(d) oxaalkyl;
$R_5$=OH, acetamido or a halogen atom;
or a pharmaceutically acceptable salt thereof,
wherein if $R=CH_2OR_1$ where $R_1$ is H, then $R_2=SO_3^-$, and
wherein if $R=CH_2OR_1$, $R_2$=H, $R_3$ is OH and $R_3'$ is H, then
$R_5$=acetamido or a halogen atom.

2. A method for enhancing immunogenicity of a compound, composition, or vaccine in a subject, the method comprising steps: (a) administering to the subject a compound, composition, or vaccine designed to stimulate a protective immune response, wherein the compound, composition, or vaccine comprises an adjuvant, wherein the adjuvant comprises a compound represented by the structure of formula (17):

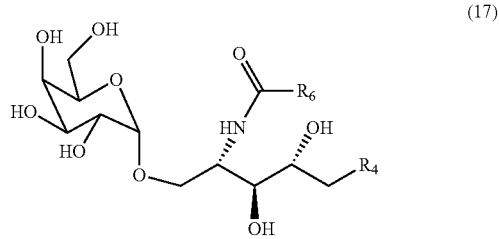

(17)

wherein
$R_4$ is selected from:
(a) alkyl,
(b) alkenyl,
(c) alkyl terminating in aryl, substituted aryl, heteroaryl or substituted heteroaryl; and
(d) alkenyl terminating in aryl, substituted aryl, heteroaryl or substituted heteroaryl, and
$R_6$ is

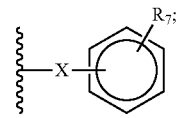

X is an alkyl chain; and
$R_7$ is chosen from halogen, H, phenyl, alkyl, alkoxy, nitro, and $CF_3$.

3. The method according to claim 2, wherein $R_4$ and X are saturated alkyl groups containing from 1 to 30 carbons.

4. The method according to claim 3, wherein $R_4$ and X are saturated alkyl groups containing from 5 to 25 carbons.

5. The method according to claim 4, wherein $R_7$ is H.

6. The method according to claim 5, wherein the compound is selected from the group consisting of:

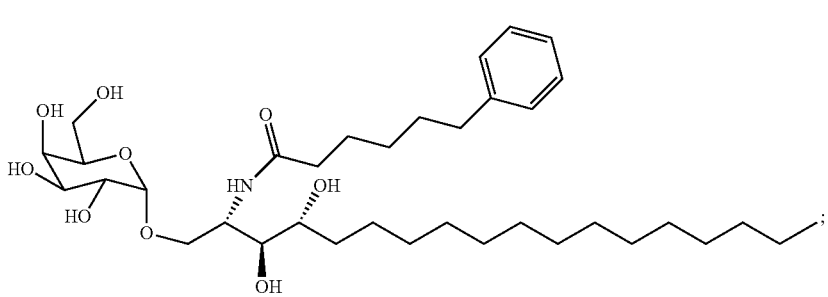

(94)

(95)
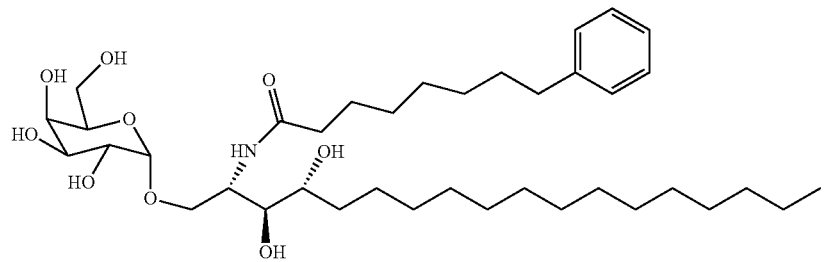
;
(96)
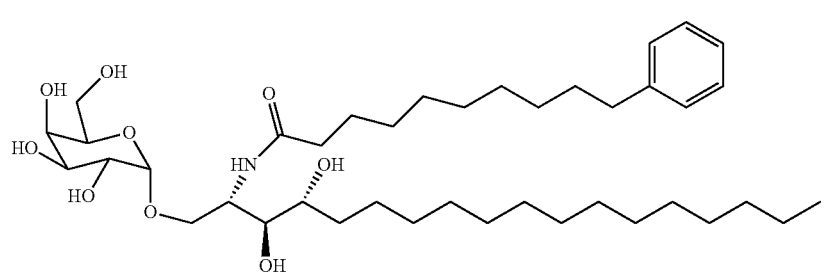
;
(97)
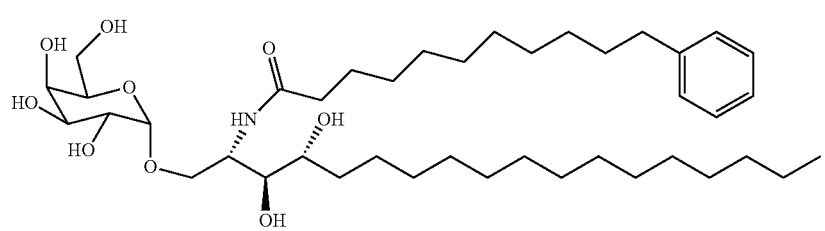
;
(98)
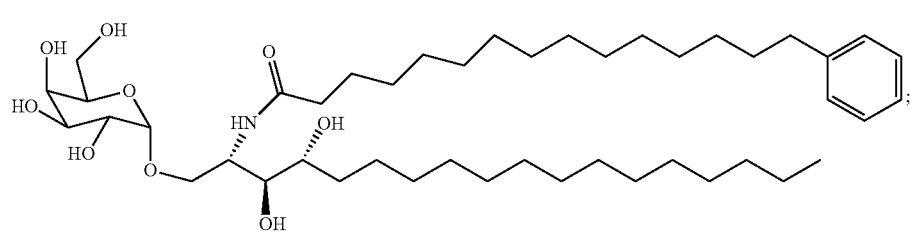
;
(99)
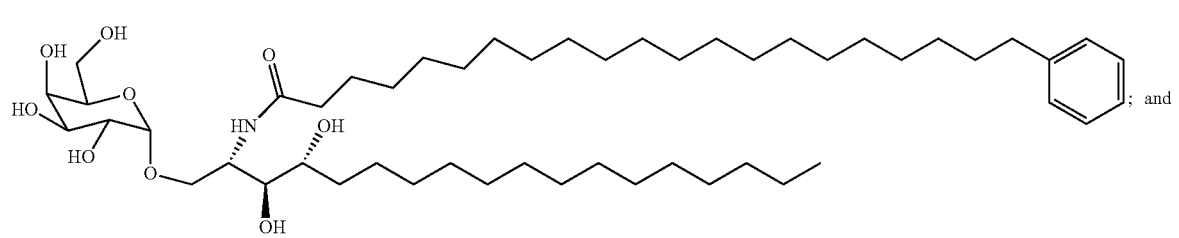
; and
(100)
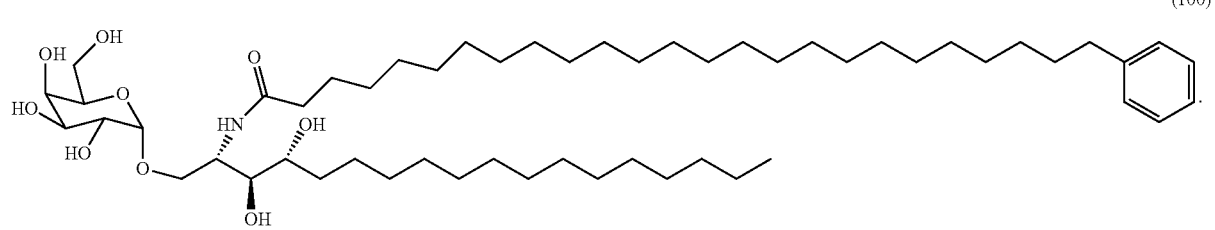
.

7. The method according to claim 4, wherein $R_7$ is halogen.
8. The method according to claim 2, wherein the compound is selected from the group consisting of:
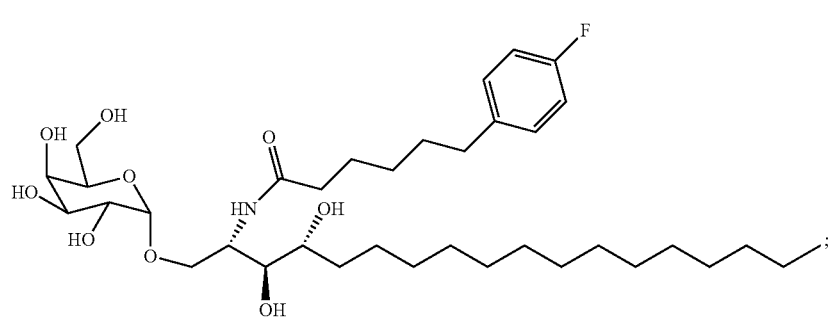
(103)
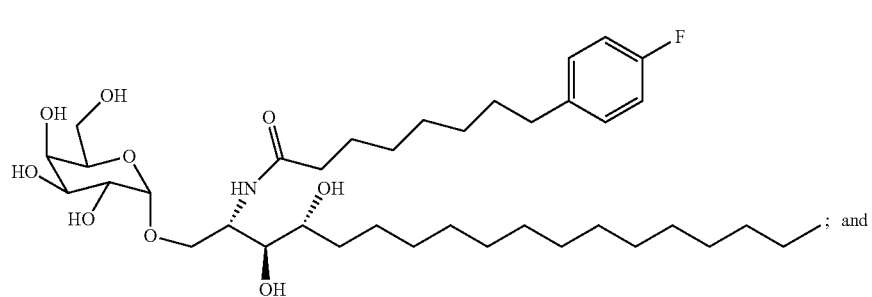
(104)
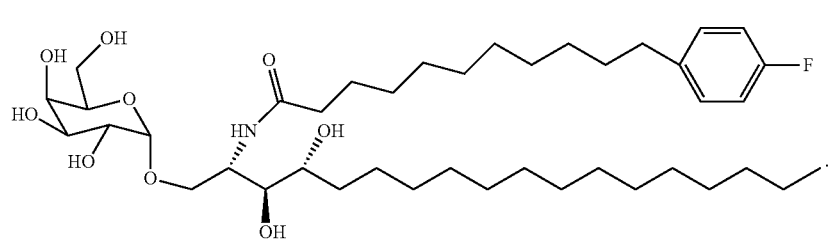
(105)
9. The method according to claim 4, wherein $R_7$ is alkoxy.
10. The method according to claim 9, wherein the compound is selected from the group consisting of:
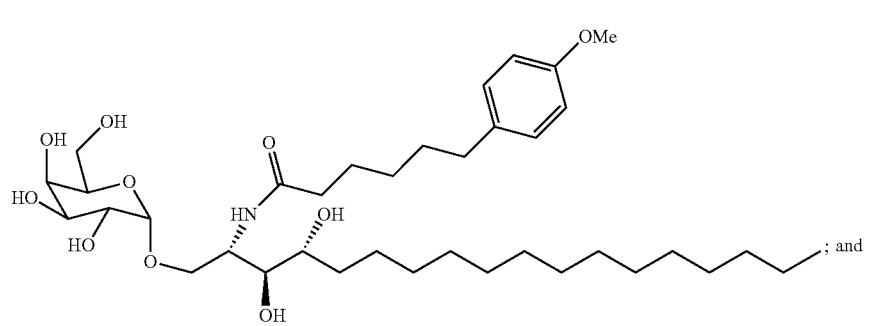
(101)

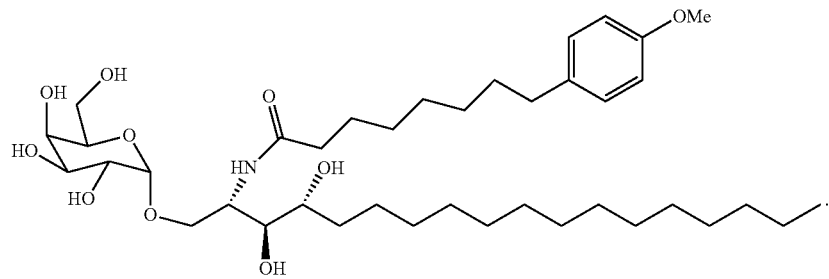
(102)
11. The method according to claim 4, wherein $R_7$ is $CF_3$.
12. The method according to claim 11, wherein the compound is selected from the group consisting of:
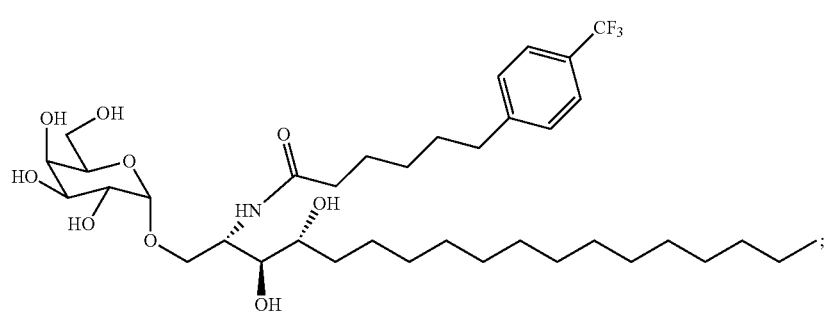
(106)
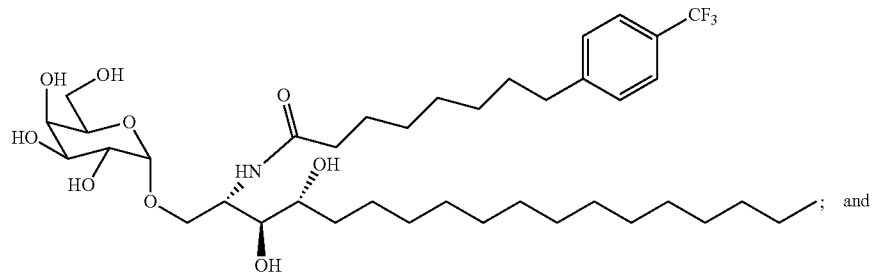
(107)
; and
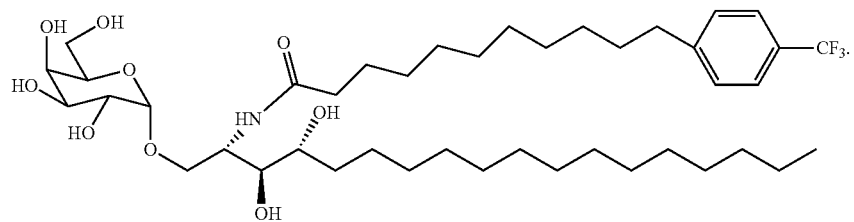
(108)

13. The method according to claim 4, wherein $R_7$ is phenyl.

14. The method according to claim 13, wherein the compound is selected from the group consisting of:

(109)
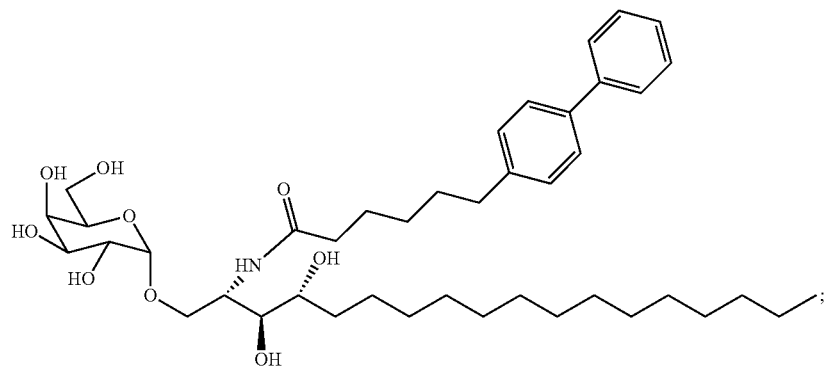

(110)
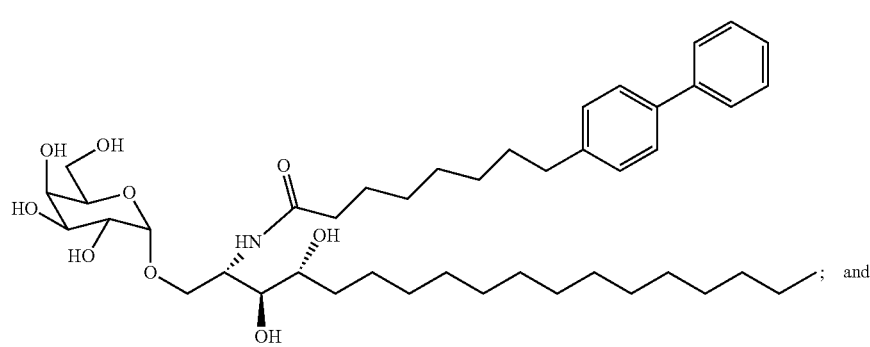
; and (111)
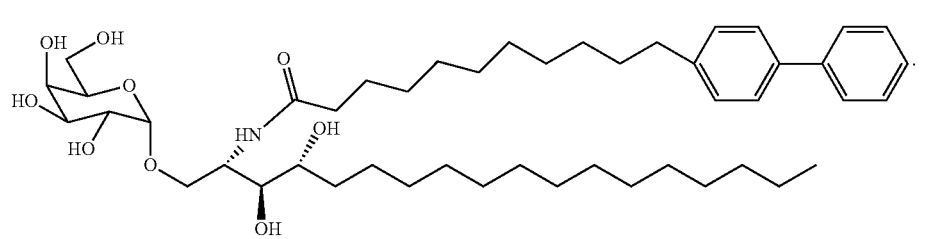
.

15. The method according to claim 2, wherein $R_4$ is

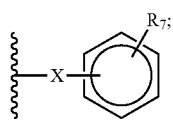

X is an alkyl chain; and
$R_7$ is chosen from halogen, H, phenyl, alkyl, alkoxy, nitro, and $CF_3$.

16. The method according to claim 15, wherein $R_6$ and X are saturated alkyl groups containing from 1 to 30 carbons.

17. The method according to claim 16, wherein $R_6$ and X are substituted alkyl groups containing from 2 to 10 carbons.

18. The method according to claim 17, wherein $R_7$ is H.

19. The method according to claim 18, wherein the compound is selected from the group consisting of:

(112)
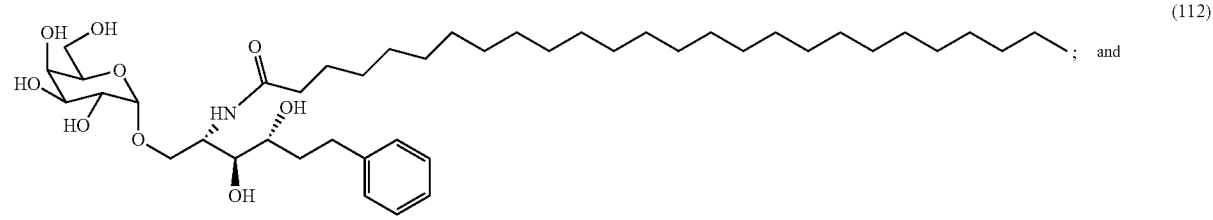
; and

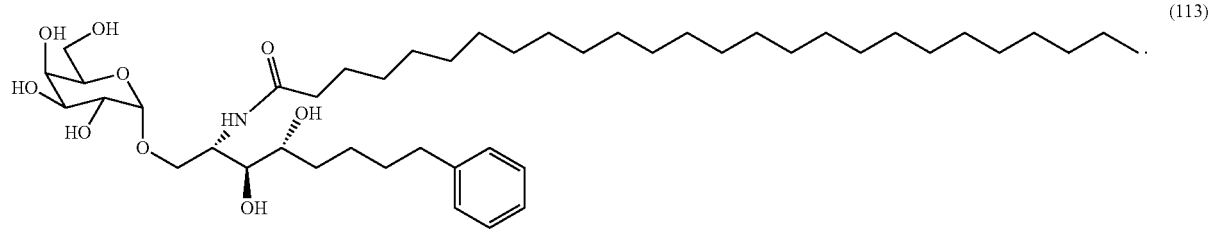
* * * * *